US006998472B1

(12) United States Patent
Robinson et al.

(10) Patent No.: US 6,998,472 B1
(45) Date of Patent: Feb. 14, 2006

(54) OBESITY GENE

(75) Inventors: Iain Clive Andrew Franklin Robinson, London (GB); Jonathan Paul Stoye, London (GB); David Flavell, London (GB); Sara Elizabeth Wells, Bristol (GB); Paul Le Tissier, London (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/484,629

(22) Filed: Jan. 18, 2000

(30) Foreign Application Priority Data

| May 6, 1999 | (GB) | ................................. 9910522 |
| Aug. 12, 1999 | (GB) | ................................. 9817566 |
| Aug. 12, 1999 | (WO) | ..................... PCT/GB99/02658 |

(51) Int. Cl.
| C12N 5/00 | (2006.01) |
| C12N 15/00 | (2006.01) |
| C07H 21/02 | (2006.01) |
| C07H 21/04 | (2006.01) |

(52) U.S. Cl. ................... 536/23.5; 536/23.1; 536/23.4; 536/24.1; 536/24.33; 435/320.1; 435/325

(58) Field of Classification Search ............... 536/23.1, 536/23.4, 23.5, 24.1, 24.33; 435/320.1, 325, 435/440

See application file for complete search history.

(56) References Cited

OTHER PUBLICATIONS

E Mohr et al., Biochimie, "A single rat genomic DNA fragment encodes both the oxytocin and vasopressin genes separated by 11 kilobases and oriented in opposite transcriptional directions," 1988, 70:649-654.*

E Schmitz et al., DNA and Cell Biology, "Rat Vasopressin and Oxytocin Genes are Linked by a long interspersed Repeated DNA element(LINE):Sequence and Transcriptional Analysis of LINE," 1991, vol. 10, No. 2,pp. 81-91.*

GenBank Accession No. H31114.*
GenBank Accession No. AA955566.*
GenBank Accession No. AA421393.*
GenBank Accession No. AA505752.*
GenBank Accession No. AA421310.*
GenBank Accession No. AA242211.*
GenBank Accession No. AA245389.*
GenBank Accession No. AA104183.*
GenBank Accession No. AA850004.*
GenBank Accession No. H31115.*

Al-Shawi, Raya, et al. (1990). Expression of a Foreign Gene in a Line of Transgenic Mice Is Modulated by a Chromosomal Position Effect. *Molecular and Cellular Biology.* 10, 1192-98.

Ang, H-L, et al. (1994). Over-expression of oxytocin in the testes of a transgenic mouse model. *Journal of Endocrinology.* 140, 53-62.

Ang, Hwee-Luan, et al. (1991). Testicular Oxytocin Gene Expression in Seminiferous Tubules of Cattle and Transgenic Mice. *Endocrinology.* 128, 2110-17.

Banerjee, Shilpi A., et al. (1994). DNA regulatory sequences of the rat tyrosine hydroxylase gene direct correct catecholaminergic cell-type specificity of a human growth hormone reporter in the CNS of transgenic mice causing a dwarf phenotype. *Molecular Brain Research.* 24, 89-106.

Bartke, A., et al (1988). Infertility in Transgenic Female Mice with Human Growth Hormone Expression: Evidence for Luteal Failure. *The Journal of Experimental Zoology.* 248, 121-124.

Bartke, A., et al. (1992). Effects of expression of human or bovine growth hormone genes on sperm production and male reproductive performance in four lines of transgenic mice. *Journal of Reproduction & Fertility. Abstract Series/ Society for the Study of Fertility.* 95, 109-118.

Bonifer, Constanze, et al. (1990). Tissue specific and position independent expression of the complete gene domain for chickent lysozyme in transgenic mice. *European Molecular Biology Organsation Journal.* 9, 2843-48.

Boss, Olivier, et al. (1997). Uncoupling protein-3: a new member of the mitochondrial carrier family with tissue-specific expression. *Febs Letters.* 408, 39-42.

Bowie, Kahle, E., et al. (1997). The Rat Corpulent (cp) Mutation Maps to the Same Interval on (Pgm1-Glut1) Rat Chromosome 5 as the Fatty (fa) Mutation. *Obesity Research.* 5, 142-5.

Bucchini, D., et al. (1986). Pancreatic expression of human insulin gen in transgenic mice. *National Academy of Sciences.* 83, 2511-15.

Chen, Hong, et al., (1996). Evidence that the Diabetes Gene Encodes the Leptin Receptor: Indentification of a Mutation in the Leptin Receptor Gene in db/db Mice. *Cell.* 84, 491-495.

Coleman, D.L. and Eicher, E. M. (1990). Fat (fat) and Tubby (tub): Two Autosomal Recessive Mutations Causing Obesity Syndromes in the Mouse. *Journal of Hereditary.* 81, 424-27.

Comuzzie, Anthongy G. and Allison, David B. (1998). The Search for Human Obesity Genes. *Science.* 280, 1374-77.

Cool, David R., et al. (1997). Carboxypeptidase E is a Regulated Secretory Pathway Sorting Receptor: Genetic Obliteration Leads to Endocrine Disorders in Cpe$^{fat}$ Mice. *Cell.* 88, 73-83.

(Continued)

*Primary Examiner*—Joseph Woitach
(74) *Attorney, Agent, or Firm*—Kathleen M. Williams; Palmer & Dodge LLP

(57) ABSTRACT

The invention describes a previously unknown gene, termed 5'OT-EST, which is responsible for inducing an obesity and/or infertility phenotype in transgenic animals, and transgenic animals comprising mutants of 5'OT-EST which are useful for assaying compounds for the treatment of obesity and/or infertility.

15 Claims, 14 Drawing Sheets

OTHER PUBLICATIONS

Fan, Wei, et al. (1997). Role of melanocortinergic neurons in feeding and the agouti obesity syndrome. *Nature.* 385, 165-8.

Flavell, D.M., et al. (1996). Dominant dwarfism in transgenic rats by targeting human growth hormone (GH) expression to hypothalamic GH-releasing factor neurons. *European Molecular Biology Organisation Journaal.* 15, 3871-79.

Fujiwara, Y., et al. (1997). Position-Independent and High-Level Expression of Human α-Lactalbumin in the Milk of Transgenic Rats Carrying a 210-kb YAC DNA. *Molecular Reproduction and Development.* 47, 157-163.

Good, Deborah J., et al. (1997). Hypogonadism and obesity in mice with a targeted deletion of the Nhlh2 gene. *Nature Genetics.* 15, 397-401.

Graham, Melissa (1997). Overexpression of Agrt leads to obesity in transgenic mice. *Nature Genetics.* 17, 273-274.

Grant, Frederick D., et al. (1993). Expression of the Rat Arginine Vasopressin Gene in Transgenic Mice. *Molecular Endocrinology.* 7, 659-67.

Grosveld, Frank, et al. (1987). Position-Independent, High-Level Expression of the Human β-Globin Gene in Transgenic Mice. *Cell.* 51, 975-85.

Habener, Joel F., et al. (1989). Metallothionein-Vasopressin Fusion Gene Expression in Trangenic Mice. *Journal of Biological Chemistry.* 264, 18844-52.

Hammer, Robert E., et al. (1985). Production of transgenic rabbits, sheep and pigs by microinjection. *Nature.* 315, 680-83.

Hanahan, Douglas, et al. (1983). Studies on Transformation of *Escherichia coli* with Plamids *Journal of Molecular Biology.* 166, 557-580.

Ho. Mei-Yin, et al. (1995). Bovine Oxytocin Transgenes in Mice. *Journal of Biological Chemistry.* 270, 27199-05.

Hollingshead, Philiip G., et al. (1989). A Dominant Phenocopy of Hypopituitarism in Transgenic Mice Resulting from Central Nervous System Synthesis of Human Growth Hormone. *Endocrinology.* 125, 1556-64.

Huber, Matthias, et al. (1994) Chromosomal position effects in chicken lysozyme gene transgenic mice are correlated with supression of Dnase I hypersensitive site formation. *Nucleic Acids Research.* 22, 4195-4201.

Huszar, Dennis, et al. (1997). Targeted Disruption of the Melanocortin-4 Receptor Results in Obesity in Mice. *Cell Press.* 88, 131-141.

Jamal, Zahirali, et al. (1997). Phosphatidate phosphohydrolases in liver, heart and adipose tissue of the JCF:LA corpulent rat and the lean genotypes: implications for glycerolipid synthesis and signal transduction. *International Journal of Obesity.* 116, 789-99.

Jones, Beverly K., et al. (1995). The Human Growth Hormone Gene is Regulated by a Multicomponent Locus Control Region. *Molecular and Cellular Biology.* 15, 7010-21.

Klebig, M.L., et al. (1995) Ectopic expression of the agouti gene in transgenic mice causes obesity, features of type II diabetes, and yellow fur. *National Academy of Sciences.* 92, 4728-32.

Kristensen, Peter, et al. (1998). Hypothalamic CART is a new anorectic peptide regulated by leptin. *Nature.* 393, 72-76.

Kleyn, Patrick W., et al. (1996). Identification and Characterization of the Mouse Obesity Gene tubby: A Member of Novel Gene Family. *Cell Press.* 85, 281-90.

Lacy, Elizabeth, et al. (1983). A Foreign β-Globin Gene in Transgenic Mice: Intergration at Abnormal Chromosomal Positions and Expression in Inappropriate Tissues. *Cell.* 34, 343-358.

Lecea, L. De, et al (1998). The hyprocretins: Hypothalamus-specific peptides with neuroexcitatory activity. *National Academy of Sciences.* 95, 322-327.

Lee, G.H., et al. (1997). Leptin receptor mutations in 129 $db^{3J}/db^{3J}$ mice and NIH $fa^{cp}/fa^{cp}$ rats. *Mammalian Genome.* 8, 445-7.

McGrane, Mary M., et al. (1988). Tissue-specific Expression and Dietary Regulation of a Chimeric Phosphoenolypruvate Carboxykinase/Bovine Growth Hormone Gene in Transgenic Mice. *Journal of Biological Chemistry.* 263, 11443-51.

Miller, Miles, W., et al. (1993). Cloning of the mouse agouti gene predicts a secreted protein ubiquitously expressed in mice carrying the lethal yellow mutation. *Genes & Development.* 7, 454-467.

Millet, Laurence, et al. (1997). Increased Uncoupling protein-2 and -3 mRNA Expression during Fasting in Obese and Lean Humans. *Journal of Clinical Investigations.* 100, 2665-70.

Moon Byoung Chon and Jeffrey M. Friedman (1997). The Molecular Basis of the Obese Mutation in $ob^{2J}$ Mice. *GENOMICS.* 42, 152-6.

Morello, D., et al. (1986). Studies on the expression of an H-2K/human growth hormone fusion gene in giant transgenic mice. *European Molecular Biology Organisation Journal.* 5, 11877-83.

Murphy D. and Ho, M. Y. (1995). Oxytocin Transgenic Mice. *Oxytocin.* 395, 67-78.

Naggert, Jürgen K., et al. (1995). Hyperproinsulinaemia in obese fat/fat mice associated with a carboxypeptidase E mutation which reduces enzyme activity. *Nature Genetics.* 10, 135-142.

North, Michael A., et al (1997). Molecular characterization of TUB, TULP1, and TULP2, members of the novel tubby gene family and their possible relation to ocular diseases. *National Academy of Sciences..* , 94, 128-33.

Ohki-Hamazaki, Hiroko, et al (1997). Mice lacking bombesin receptor subtype-3 develop metabolic defects and obesity. *Nature.* 390, 165-169.

Ollmann, Michael M. (1997). Antagonism of Central Melanocortin Receptors in Vitro and in Vivo by Agouti-Related Protein. *Science.* 278, 135-138.

Ornitz, David M. et al. (1985). Specific expression of an elastase-human growth hormone fusion gene in pancreatic acinar cells of transgenic mice. *Nature.* 313, 600-02.

Palmiter, Richard D., et al. (1982). Dramatic growth of mice that develop from eggs microinjected with metallothionein-growth hormone fusion genes. *Nature.* 300, 611-615.

Pursel, Vernon G., et al. (1989). Genetic Engineering of Livestock. *Science.* 244, 1281-87.

Qu, Daqing, et al. (1996). A role for melanin-concentrating hormone in the central regulation of feeding behaviour. *Nature.* 380, 243-247.

Richard, Denis, et al. (1996). Expression of Corticotropin-Releasing Factor and Its Receptors in the Brain of Lean and Obese Zucker Rats. *Endocrinology.* 137, 4786-95.

Quaife, Carol., et al. (1989). Histopathology Associated with Elevated Levels of Growth Hormone and Insulin-Like Growth Factor I in Transgenic Mice. *Endocrinology.* 124, 40-48.

Russo, Andrew F., et al. (1988). Neuronal Expression of Chimeric Genes in Transgenic Mice. *Neuron.* 1, 311-320.

Sakurai, Takeshi, et al. (1998). Orexins and Orexin Receptors: A family of Hypothalamic Neuropeptides and G Protein-Coupled Receptors that Regulate Feeding Behavior. *Cell.* 92, 573-85.

Sausville, Edward, et al. (1985). The Human Vasopresin Gene is Linked t the Oxytocin Gene and Is Selectively Expressed in a Cultrured Lung Cancer Cell Line. *Journal of Biological Chemistry.* 260, 10236-41.

Shanahan, Catherine M., et al. (1989). Regulation of Expression of a Sheep Metallothionein la-Sheep Growth Hormone Fusion Gene in Transgenic Mice. *Molecular and Cellular Biology.* 9, 5473-79.

Short, Mary K., et al. (1992). Tissue-Specific, Developmental, Hormonal, and Dietary Regulation of Rat Phosphoenolpyruvate Carboxykinase-Human Growth Hormone Fusion Genes in Transgenic Mice. *Molecular and Cellular Biology.* 12, 1007-20.

Soichi, Takiguchi, et al. (1998). A disrupted cholecystokinin A receptor gene induces diabetes in obese rats synergistically with ODB1 gene. *American Journal of Physiology.* 274, E265-70.

Stewart, Timothy, et al. (1992). An Evaluation of the Functions of the 22-Kilodalton (kDa), the 20-kDa, and the N-Terminal Polypeptide Forms of Human Growth Hormone Using Transgenic Mice. *Endocrinology.* 130, 405-414.

Szabo, Marta, et al. (1995). Autofeedback Suppression of Growth Hormone (GH) Secretion in Transgenic Mice Expressing a Human GH Reporter Targeted by Tyrosine Hydroxylase 5' -Flanking Sequences to the Hypothalamus. *Endocrinology.* 136, 4044-48.

Takaya, Kazuhiko, et al. (1996). Molecular Cloning of Rat Leptin Receptor Isoform Complementary DNAs—Identification of a Missense Mutation in Zucker Fatty (fa/fa) Rats. *Bichemical and Biophysical Research Communications.* 225, 75-83.

Tartaglia, Louis A., et al. (1995). Identification and Expression Cloning of a Leptin Receptor, OB-R. *Cell.* 83, 1263-71.

Vidal-Puig, Antonio (1997). UCP3: An Uncoupling Protein Homologue Expressed Preferentially and Abundantly in Skeletal Muscle and Brown Adipose Tissue. *Biochemical and Biophysical Research Communications.* 235, 79-82.

Zeng, Q., et al. (1994). Expression of a rat vasopressin transgene in rat testes. *Journal of Reproduction & Fertility. Abstract series/Society for the Study of Fertility.* 102, 471-81.

* cited by examiner

Figure 6    5'OT-EST PROTEIN OF DIFFERENT SPECIES

Mouse
MLRALNRLAQRPGDRPPTPLLLPVRGRKTRHDPPAKSKVGRVQTPPAVDPAEFFVLTERY
GQYRETVRALRLEFTLDVRRKLHEARAGVLAERKAQQAITEHRELMAWNRDENRRMQELR
IARLQLEAQAQEVQKAEAQRQRAQEEQAWVQLKEQEVLKLQEEAKNFITRENLEARIEEA
LDSPKSYNWAVTKEGQVVRN Rat
MLRALNRLAARPGGQPPTLLLLPVRGRKTRHDPPAKSKVGRVKMPPAVDPAELFVLTERY
RQYRETVRALRREFTLEVRGKLHEARAGVLAERKAQEAIREHQELMAWNREENRRLQELR
IARLQLEAQAQELRQAEVQAQRAQEEQAWVQLKEQEVLKLQEEAKNFITRENLEARIEEA
LDSPKSYNWAVTKEGQVVRN Human
MLRALSRLGAGTPCRPRAPLVLPARGRKTRHDPLAKSKIERVNMPPAVDPAEFFVLMERY
QHYRQTVRALRMEFVSEVQRKVHEARAGVLAERKALKDAAEHRELMAWNQAENRRLHELR
IARLRQEEREQEQRQALEQARKAEEVQAWAQRKEREVLQLQEEVKNFITRENLEARVEAA
LDSRKNYNWAITREGLVVRPQRRDS Alignment
Mouse    MLRALNRLAQRPGDRPPTPLLLPVRGRKTRHDPPAKSKVGRVQTPPAVDPAEFFVLTERY
Rat      MLRALNRLAARPGGQPPTLLLLPVRGRKTRHDPPAKSKVGRVKMPPAVDPAELFVLTERY
Human    MLRALSRLGAGTPCRPRAPLVLPARGRKTRHDPLAKSKIERVNMPPAVDPAEFFVLMERY Mouse    GQYRETVRALRLEFTLDVRRKLHEARAGVLAERKAQQAITEHRELMAWNRDENRRMQELR
Rat      RQYRETVRALRREFTLEVRGKLHEARAGVLAERKAQEAIREHQELMAWNREENRRLQELR
Human    QHYRQTVRALRMEFVSEVQRKVHEARAGVLAERKALKDAAEHRELMAWNQAENRRLHELR Mouse    IARLQLEAQAQEVQKAEAQRQRAQEEQAWVQLKEQEVLKLQEEAKNFITRENLEARIEEA
Rat      IARLQLEAQAQELRQAEVQAQRAQEEQAWVQLKEQEVLKLQEEAKNFITRENLEARIEEA
Human    IARLRQEEREQEQRQALEQARKAEEVQAWAQRKEREVLQLQEEVKNFITRENLEARVEAA Mouse    LDSPKSYNWAVTKEGQVVRN
Rat      LDSPKSYNWAVTKEGQVVRN
Human    LDSRKNYNWAITREGLVVRPQRRDS Predicted deleted form in JP17
MLRALNRLAARPGGQPPTLLLLPVRGprprsfsapfssqds
                                ↑

|   | 20 weeks | |
|---|---|---|
|   | non-transgenic | JP17 transgenic |
| a | 260.33 ± 0.28 | 243.34 ± 0.13 *** |
| b | 92.67 ± 0.29 | 115.14 ± 0.24*** |

|   | 52 weeks | |
|---|---|---|
|   | non-transgenic | JP17 transgenic |
| a | 273.83 ± 0.28 | 261.0 ± 0.45 ns |
| b | 113.83 ± 0.10 | 157.83 ± 0.61 *** |

|  | Cholesterol mg/dl | Triglyceride mg/dl | Glucose mg/dl | Insulin ng/ml | Leptin ng/ml | Corticosterone ng/ml |
|---|---|---|---|---|---|---|
| MALE TRANSGENIC | 122.3 +/- 6.4 | *295.6 +/- 28.7 | 114.7 +/- 4.2 | 1.94 +/- 0.89 | *24.4 +/- 1.49 | 168.9 +/- 23.5 |
| MALE NON-TRANSGENIC | 129.9 +/- 9.3 | 178.9 +/- 23.5 | 121.0 +/- 3.9 | 2.8 +/- 1.93 | 9.51 +/- 2.14 | 113.9 +/- 20.3 |
| FEMALE TRANSGENIC | 94.9 +/- 5.9 | 224.2 +/- 52.3 | 126.3 +/- 3.3 | 2.51 +/- 0.64 | *14.74 +/- 1.38 | 256.3 +/- 104.1 |
| FEMALE NON-TRANSGENIC | 100.2 +/- 8.0 | 195.5 +/- 34.5 | 135.4 +/- 6.7 | 2.54 +/- 2.32 | 4.58 +/- 0.47 | 349.3 +/- 123.7 |

FIG. 12

SEQUENCE LISTING

```
<160> NUMBER OF SEQ ID NOS: 37

<210> SEQ ID NO 1
<211> LENGTH: 924
<212> TYPE: DNA
<213> ORGANISM: Rattus sp.

<400> SEQUENCE: 1
tgtcatgttg cgggctttga accgcctggc cgcgcggccc gggggccagc ccccaaccct     60
gctccttctg cccgtgcgcg gccgcaagac ccgccacgat ccgcctgcca agtccaaggt    120
cgggcgcgtg aaaatgcctc ctgcagtgga ccctgcggaa ttgttcgtgt tgaccgagcg    180
ctaccgacag taccgggaga cggtgcgcgc tctcaggcga gagttcacat tggaggtgcg    240
agggaaattg cacgaggccc gagccggggt tctggctgag cgcaaggcgc aagaggccat    300
cagagagcac caggagctga tggcctggaa ccgggaggag aaccggagac tgcaggaact    360
acggatagct aggttgcagc tcgaagcaca ggcccaggag ctgcggcagg ctgaggtcca    420
ggcccagagg gcccaggagg agcaggcttg ggtgcaactg aaagaacaag aagttctcaa    480
```

```
actgcaggag gaggccaaaa acttcatcac tcgggagaac ctggaggcac ggatagaaga    540
ggccttggac tctccgaaga gttataactg ggcggtcacc aaagaagggc aggtggtcag    600
gaactgagaa cagaggcctc tcaggcccaa ataaggacag tgcttgccta gggactggat    660
attggggtag aaattggtgc atcccaggag ggtggcacag ccttgtccag agcagccccc    720
attcattcta gatttggcac caggtatagt acctgttctg acaccacata caaactccgg    780
acagcattaa actctgggaa gttcctatca cacagaagat cagactggac tgtcccctct    840
agaagccaag agctgtctcc tgagtttctt ggaatagtgt gagcccaatg tttcctgctt    900
ttataaataa actattggaa agca                                          924

<210> SEQ ID NO 2
<211> LENGTH: 200
<212> TYPE: PRT
<213> ORGANISM: Rattus sp.

<400> SEQUENCE: 2

Met Leu Arg Ala Leu Asn Arg Leu Ala Ala Arg Pro Gly Gly Gln Pro
1               5                   10                  15

Pro Thr Leu Leu Leu Pro Val Arg Gly Arg Leu Thr Arg His Asp
            20                  25                  30

Pro Pro Ala Leu Ser Leu Val Gly Arg Val Leu Met Pro Pro Ala Val
        35                  40                  45

Asp Pro Ala Glu Leu Phe Val Leu Thr Glu Arg Tyr Arg Gln Tyr Arg
    50                  55                  60

Glu Thr Val Arg Ala Leu Arg Arg Glu Phe Thr Leu Glu Val Arg Gly
65                  70                  75                  80

Lys Leu His Glu Ala Arg Ala Gly Val Leu Ala Glu Arg Lys Ala Gln
                85                  90                  95

Glu Ala Ile Arg Glu His Gln Glu Leu Met Ala Trp Asn Arg Glu Glu
            100                 105                 110

Asn Arg Arg Leu Gln Glu Leu Arg Ile Ala Arg Leu Gln Leu Glu Ala
        115                 120                 125

Gln Ala Gln Glu Leu Arg Gln Ala Glu Val Gln Ala Gln Arg Ala Gln
    130                 135                 140

Glu Glu Gln Ala Trp Val Gln Leu Lys Glu Gln Glu Val Leu Lys Leu
145                 150                 155                 160

Gln Glu Glu Ala Lys Asn Phe Ile Thr Arg Glu Asn Leu Glu Ala Arg
                165                 170                 175

Ile Glu Glu Ala Leu Asp Ser Pro Lys Ser Tyr Asn Trp Ala Val Thr
            180                 185                 190

Lys Glu Gly Gln Val Val Arg Asn
        195                 200

<210> SEQ ID NO 3
<211> LENGTH: 998
<212> TYPE: DNA
<213> ORGANISM: Homo sapiens

<400> SEQUENCE: 3
atgctacgcg cgctgagccg cctgggcgcg gggaccccgt gcaggccccg ggcccctctg     60
gtgctgccag cgcgcggccg caagacccgc cacgacccgc tggccaaatc caagatcgag    120
cgagtgaaca tgccgcccgc ggtggaccct gcggagttct tcgtgctgat ggagcgttac    180
cagcactacc gccagaccgt gcgcgccctc aggatggagt tcgtgtccga ggtgcagagg    240
```

-continued

```
aaggtgcacg aggcccgagc cggggttctg gcggagcgca aggccctgaa ggacgccgcc      300
gagcaccgcg agctgatggc ctggaaccag gcggagaacc ggcggctgca cgagctgcgg      360
atagcgaggc tgcggcagga ggagcgggag caggagcagc ggcaggcgtt ggagcaggcc      420
cgcaaggccg aagaggtgca ggcctgggcg cagcgcaagg agcgggaagt gctgcagctg      480
caggaagagg tgaaaaactt catcacccga gagaacctgg aggcacgggt ggaagcagca      540
ttggactccc ggaagaacta caactgggcc atcaccagag aggggctggt ggtcaggcca      600
caacgcaggg actcctaggg gcccagtaag gacagtgccc gccagggacc atgtatgtat      660
catggcggaa gagttggccc tgacctggaa taaagcagtt ggtgttgctt atgaggaagg      720
ttcagcctta tccagcacag ccttcacgtt ttgccctctg ctgtcaccac ttggtcagaa      780
acttccaaac gcagtgccct gttctgccgg tgtgtaaagc ctcagcgcac aggagaccc      840 tagagtggtt tccatctcac agagaatcag acaggccaca gcccctcag gcagccaggt       900 catctgagta tcattaagag tagtgatggg aagattacag tctgagggcc aaacgtgcct       960
gcttcctgtt tttgtaaata aagttttgtt ggaacaca                              998
```

```
<210> SEQ ID NO 4
<211> LENGTH: 205
<212> TYPE: PRT
<213> ORGANISM: Homo sapiens

<400> SEQUENCE: 4
```

Met Leu Arg Ala Leu Ser Arg Leu Gly Ala Gly Thr Pro Cys Arg Pro
1               5                   10                  15

Arg Ala Pro Leu Val Leu Pro Ala Arg Gly Arg Lys Thr Arg His Asp
                20                  25                  30

Pro Leu Ala Lys Ser Lys Ile Glu Arg Val Asn Met Pro Ala Val
            35                  40                  45

Asp Pro Ala Glu Phe Phe Val Leu Met Glu Arg Tyr Gln His Tyr Arg
        50                  55                  60

Gln Thr Val Arg Ala Leu Arg Met Glu Phe Val Ser Glu Val Gln Arg
65                  70                  75                  80

Lys Val His Glu Ala Arg Ala Gly Val Leu Ala Glu Arg Lys Ala Leu
                85                  90                  95

Lys Asp Ala Ala Glu His Arg Glu Leu Met Ala Trp Asn Gln Ala Glu
            100                 105                 110

Asn Arg Arg Leu His Glu Leu Arg Ile Ala Arg Leu Arg Gln Glu Glu
        115                 120                 125

Arg Glu Gln Glu Gln Arg Gln Ala Leu Glu Gln Ala Arg Lys Ala Glu
    130                 135                 140

Glu Val Gln Ala Trp Ala Gln Arg Lys Glu Arg Glu Val Leu Gln Leu
145                 150                 155                 160

Gln Glu Glu Val Lys Asn Phe Ile Thr Arg Glu Asn Leu Glu Ala Arg
                165                 170                 175

Val Glu Ala Ala Leu Asp Ser Arg Lys Asn Tyr Asn Trp Ala Ile Thr
            180                 185                 190

Arg Glu Gly Leu Val Val Arg Pro Gln Arg Arg Asp Ser
        195                 200                 205

```
<210> SEQ ID NO 5
<211> LENGTH: 943
<212> TYPE: DNA
<213> ORGANISM: Mus musculus
```

-continued

```
<400> SEQUENCE: 5
tgtcatgttg cgcgctctga accgcctggc gcagcggccg ggagaccggc ccccgacccc      60
gctgctcctg cccgtgcgcg ccgcaagac ccgccatgac ccgcctgcca aatccaaggt     120
cggacgggtg cagacgcctc ccgccgtgga ccctgcggaa ttcttcgtgt tgaccgagcg     180
ctacggacag taccgggaga ccgtgcgcgc tctcaggcta gagttcacgt tggatgtgcg     240
aaggaaattg cacgaggccc gagccggggt tctggccgag cgcaaggcgc agcaggccat     300
cacggagcac cggagctga tggcctggaa ccgggacgaa aaccggcgaa tgcaggagct     360
acggatagcg aggttgcagc tggaagcaca ggcccaggag gtgcagaagg ctgaggccca     420
gcgccagagg gctcaggagg agcaggcttg ggtgcaactg aaagagcaag aagtgctcaa     480
gctgcaggag gaggcaaaaa acttcatcac tcgggagaac ctggaggcac ggatagaaga     540
agcgttggac tctccgaaga gttacaactg ggccgtcacc aaagaagggc aggtggtcag     600
gaactgagca cagagacttc tgggggccca ataagcaca gtgcttgcct agggtctgtg     660
tactgggata ggaattggta catcccagga ggatggctca gccgtttcca gagcaacctc     720
agtcactcca ggctcggcac tcaccacctg actgggaact cccagatgtc cctgttctgg     780
caccacagtc aaactgaggg cagcattaaa ctctgggaag ttcctatcgc acagaggatc     840
ggactggact gtgtccctct agaagccaag cttgtcttgt aagtctcttg gagtcctgtg     900
agccaaatgt ttcctgcttt tataaataaa gtattggagc cca                      943

<210> SEQ ID NO 6
<211> LENGTH: 200
<212> TYPE: PRT
<213> ORGANISM: Mus musculus

<400> SEQUENCE: 6

Met Leu Arg Ala Leu Asn Arg Leu Ala Gln Arg Pro Gly Asp Arg Pro
 1               5                  10                  15

Pro Thr Pro Leu Leu Pro Val Arg Gly Arg Lys Thr Arg His Asp
             20                  25                  30

Pro Pro Ala Lys Ser Lys Val Gly Arg Val Gln Thr Pro Pro Ala Val
             35                  40                  45

Asp Pro Ala Glu Phe Phe Val Leu Thr Glu Arg Tyr Gly Gln Tyr Arg
         50                  55                  60

Glu Thr Val Arg Ala Leu Arg Leu Glu Phe Thr Leu Asp Val Arg Arg
65                  70                  75                  80

Lys Leu His Glu Ala Arg Ala Gly Val Leu Ala Glu Arg Lys Ala Gln
                 85                  90                  95

Gln Ala Ile Thr Glu His Arg Glu Leu Met Ala Trp Asn Arg Asp Glu
                100                 105                 110

Asn Arg Arg Met Gln Glu Leu Arg Ile Ala Arg Leu Gln Leu Glu Ala
            115                 120                 125

Gln Ala Gln Glu Val Gln Lys Ala Glu Ala Gln Arg Gln Arg Ala Gln
        130                 135                 140

Glu Glu Gln Ala Trp Val Gln Leu Lys Glu Gln Glu Val Leu Lys Leu
145                 150                 155                 160

Gln Glu Glu Ala Lys Asn Phe Ile Thr Arg Glu Asn Leu Glu Ala Arg
                165                 170                 175
```

```
Ile Glu Glu Ala Leu Asp Ser Pro Lys Ser Tyr Asn Trp Ala Val Thr
            180                 185                 190

Lys Glu Gly Gln Val Val Arg Asn
            195                 200

<210> SEQ ID NO 7
<211> LENGTH: 2852
<212> TYPE: DNA
<213> ORGANISM: Homo sapiens

<400> SEQUENCE: 7
tgacctctgt ggatctgata tacatgtaag tgacagacca tccgagctat atagtgagac     60
ctgtgcaagg aaggatggag tgcacgttcc ctgatgttca gagcaaccct gtgtcactcc    120
aggtaggtga gatgagagga agagggtggc cttggcctgg gcctcctacg ggcctggaag    180
ttgggagaag gatgtaagca gactctgttc tcttctgaga aatatcaggt attgcagtca    240
gcccaggctc ctcagaccct cctaagtgca gattctctgc agaatctggt gttgacaaca    300
ctaatgagta ggatgagact tcagttccct agccctcacc gtcagcttct gattaccaac    360
aactctccca gaggagagcc atctaccttt gggacagatg ctctctgccc tgcactgcct    420
cctgtttctc ttcattgtag aggaagatag tactttaaaa gcttcataaa tggtctcaag    480
gtgggaagac cccggctcag gtgaaagagg acaagcgtca cctcacacag gccacccagt    540
agaaaacaag tgatcactga tactgagaac tctggcaatt gcagagctgc ccaagaccac    600
aacagggcag tgcaatgcaa ggaaaaggtt tgttgctcga ttgcaaacct aaagtttaaa    660
gtgcatcagg agaacgctta ctcaaagagg aagtgtaagc ctaacttaag tagctagaag    720
ctcagaattt cttgcatcag ccctggaagg gtacacaggc caccggtggg ccagagaacc    780
acacgctttg gggcggtgtc caagcttgtg aacaagtagg caagagcgcc tggtgttgta    840
gctgtcattg gcgggcaata cagcccagcg aactgtggtc tccaaggtgc ccctcgaccc    900
tcccactcta cccgagactc cagggacgcg atgggccaga cagcaagagc tccgcctacg    960
ggggcgggga caggagattc ccgtgatgct cctcgaccac ttccggacag ggcgcaggcg   1020
ctagctgtca tgttgcgggc tttgaaccgc ctggccgcgc ggcccggggg ccagccccca   1080
accctgctcc ttctgcccgt gcgcggccca cggccccgct cattctcggc tccttttttcc  1140 tcgcaggata gctaggttgc agctcgaagc acaggcccag gagctgcggc aggctgaggt   1200
ccaggcccag agggcccagg aggagcaggc ttgggtgcaa ctgaaagaac aagaagttct   1260
caaactgcag gtgggccgag gtcgtgagga atgtgggtat tggagattcc ggtgagggag   1320
gctctgggga gagcagcaca gggtgtcaag tgaccagtct tcaggaggct tctctctctg   1380
ctctgcacac acagagtgcc tcccagacaa tggtcaatga aaggttacag gctagtattg   1440
ccgtgtgaaa cttgaaggtc agggaaacca taaatgagaa tggagctgtt tttattgtgt   1500
aagggagagt gacaaggttg agagagtcca ccaccccgca cctcccccg ccccaatca    1560 ggttgtcacg attcgattcg ttcttgggtt gtggctgaga gatctgatgg gtaattgtcc   1620
gaggaagagg gatataatgg ttgaggtcac ctagtacagt tgtgctggcc tattggtggg   1680
acactcaaag gggccctggg ctcttttgac acccttctta aggtgggcta gagacagtaa   1740
gttatgcagg cagccagctc tgagagatcc cacgtagcta acctttctct tcccgtagga   1800
ggaggccaaa aacttcatca ctcgggagaa cctggaggca cggatagaag aggccttgga   1860
ctctccgaag agttataact gggcggtcac caaagaaggg caggtggtca ggaactgaga   1920
acagaggcct ctcaggccca ataaggaca gtgcttgcct agggactgga tattggggta    1980
```

```
gaaattggtg catcccagga gggtggcaca gccttgtcca gagcagcccc cattcattct    2040
agatttggca ccaggtatag tacctgttct gacaccacat acaaactccg gacagcatta    2100
aactctggga agttcctatc acacagaaga tcagactgga ctgtcccctc tagaagccaa    2160
gagctgtctc ctgagtttct tggaatagtg tgagcccaat gtttcctgct tttataaata    2220
aactattgga agcaaagcc ttttgttatg tggcttgctt tttcttgttg tagaataagt     2280
ttatttgtcc cagttatttg ggtcttaagg ttattagcca aaagccagtt cacctaactg    2340
agccaggagt tagttatctg ctttgctcaa tcctgggctt tgctgggtag ggtcaggtgt    2400
gtccaaggtc cagaaagcaa aaagggtgcc ccgtttctcc tgggaaggct tccccgtcag    2460
tgatttctgt aaccggaccc tgccctgaca cagcgtcatt ggactaccca gcagacagta    2520
gactccactc taaacccgct tcttgcggtc agttgctgtc cttcagtgtg tgtaagcagt    2580
ggccagacag caccctggg tgtcatttca agactctctc accttggtct gctttacgtt     2640
tggtttgatt tggtttgttc tggttttga gacgaggcct ttcactggaa cctggcactc      2700
agtatttaga ctgcccagcc agctagcctc agagaatgca tctgcgtatg cttgcctggc    2760
gctggaattc ggtgcacatg gctttgatgt gtaccgggga tcagacacag atgtttcatg    2820
agtgcagtgc atgcctgtta gtggtagagc tc                                  2852
```

<210> SEQ ID NO 8
<211> LENGTH: 41
<212> TYPE: PRT
<213> ORGANISM: Homo sapiens

<400> SEQUENCE: 8

```
Met Leu Arg Ala Leu Asn Arg Leu Ala Ala Arg Pro Gly Gly Gln Pro
 1               5                   10                  15

Pro Thr Leu Leu Leu Leu Pro Val Arg Gly Pro Arg Pro Arg Ser Phe
                20                  25                  30

Ser Ala Pro Phe Ser Ser Gln Asp Ser
            35                  40
```

<210> SEQ ID NO 9
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 9
ttcacaccac tctgtcgaac                                                 20

<210> SEQ ID NO 10
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 10
aggaggaaga caggtgaaag                                                 20

```
<210> SEQ ID NO 11
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 11
tcatgttgcg ggctttgaac                                              20

<210> SEQ ID NO 12
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 12
tctttcagtt gcacccaagc                                              20

<210> SEQ ID NO 13
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 13
gtgataggaa cttcccagag                                              20

<210> SEQ ID NO 14
<211> LENGTH: 42
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(42)
<223> OTHER INFORMATION: SYNTHETIC PRIMER

<400> SEQUENCE: 14
gcctcgtgca atttccctcg cacctccaat gtgaactctc gc                     42

<210> SEQ ID NO 15
<211> LENGTH: 42
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(42)
<223> OTHER INFORMATION: SYNTHETIC PRIMER

<400> SEQUENCE: 15
tcctgcgagg aaaaaggagc cgagaatgag cggggccgtg gg                     42
```

<210> SEQ ID NO 16
<211> LENGTH: 3264
<212> TYPE: DNA
<213> ORGANISM: Rattus sp.

<400> SEQUENCE: 16

| | | | | | |
|---|---|---|---|---|---|
| tgacctctgt | ggatctgata | tacatgtaag | tgacagacca | tccgagctat | atagtgagac | 60 |
| ctgtgcaagg | aaggatggag | tgcacgttcc | ctgatgttca | gagcaaccct | gtgtcactcc | 120 |
| aggtaggtga | gatgagagga | agagggtggc | cttggcctgg | gcctcctacg | ggcctggaag | 180 |
| ttgggagaag | gatgtaagca | gactctgttc | tcttctgaga | aatatcaggt | attgcagtca | 240 |
| gcccaggctc | ctcagaccct | cctaagtgca | gattctctgc | agaatctggt | gttgacaaca | 300 |
| ctaatgagta | ggatgagact | tcagttccct | agccctcacc | gtcagcttct | gattaccaac | 360 |
| aactctccca | gaggagagcc | atctaccttt | gggacagatg | ctctctgccc | tgcactgcct | 420 |
| cctgtttctc | ttcattgtag | aggaagatag | tactttaaaa | gcttcataaa | tggtctcaag | 480 |
| gtgggaagac | cccggctcag | gtgaaagagg | acaagcgtca | cctcacacag | gccacccagt | 540 |
| agaaaacaag | tgatcactga | tactgagaac | tctggcaatt | gcagagctgc | ccaagaccac | 600 |
| aacagggcag | tgcaatgcaa | ggaaaaggtt | tgttgctcga | ttgcaaacct | aaagtttaaa | 660 |
| gtgcatcagg | agaacgctta | ctcaaagagg | aagtgtaagc | ctaacttaag | tagctagaag | 720 |
| ctcagaattt | cttgcatcag | ccctggaagg | gtacacaggc | caccggtggg | ccagagaacc | 780 |
| acacgctttg | gggcggtgtc | caagcttgtg | aacaagtagg | caagagcgcc | tggtgttgta | 840 |
| gctgtcattg | gcgggcaata | cagcccagcg | aactgtggtc | tccaaggtgc | ccctcgaccc | 900 |
| tcccactcta | cccgagactc | cagggacgcg | atgggccaga | cagcaagagc | tccgcctacg | 960 |
| ggggcgggga | caggagattc | ccgtgatgct | cctcgaccac | ttccggacag | ggcgcaggcg | 1020 |
| ctagctgtca | tgttgcgggc | tttgaaccgc | ctggccgcgc | ggcccggggg | ccagccccca | 1080 |
| accctgctcc | ttctgcccgt | gcgcggccgc | aagacccgcc | acgatccgcc | tgccaagtcc | 1140 |
| aaggtcgggc | gcgtgaaaat | gcctcctgca | gtggaccctg | cggaattgtt | cgtgttgacc | 1200 |
| gagcgctacc | gacagtaccg | ggagacggtg | cgcgctctca | ggtgtgtgta | aagggcaggc | 1260 |
| ggccttcggc | gcccctggg | aagtgctggg | gctggaggat | gggtgctcac | ttgaagcccg | 1320 |
| tcctcaccca | ggcgagagtt | cacattggag | gtgcgaggga | aattgcacga | ggcccgagcc | 1380 |
| ggggttctgg | ctgagcgcaa | ggcgcaagag | gccatcagag | agcaccagga | gctgatggcc | 1440 |
| tggaaccggg | aggagaaccg | gagactgcag | gaactacggt | gcgagaggcg | cggggctggg | 1500 |
| tgggctgggc | taggctcacc | cacggccccg | ctcattctcg | gctccttttt | cctcgcagga | 1560 |
| tagctaggtt | gcagctcgaa | gcacaggccc | aggagctgcg | gcaggctgag | gtccaggccc | 1620 |
| agagggccca | ggaggagcag | gcttgggtgc | aactgaaaga | acaagaagtt | ctcaaactgc | 1680 |
| aggtgggccg | aggtcgtgag | gaatgtgggt | attggagatt | ccggtgaggg | aggctctggg | 1740 |
| gagagcagca | cagggtgtca | agtgaccagt | cttcaggagg | cttctctctc | tgctctgcac | 1800 |
| acacagagtg | cctcccagac | aatggtcaat | gaaaggttac | aggctagtat | tgccgtgtga | 1860 |
| aacttgaagg | tcagggaaac | cataaatgag | aatggagctg | tttttattgt | gtaagggaga | 1920 |
| gtgacaaggt | tgagagagtc | caccaccccg | cacctccccc | cgcccccaat | caggttgtca | 1980 |
| cgattcgatt | cgttcttggg | ttgtggctga | gagatctgat | gggtaattgt | ccgaggaaga | 2040 |
| gggatataat | ggttgaggtc | acctagtaca | gttgtgctgg | cctattggtg | ggacactcaa | 2100 |
| agggccctg | ggctcttttg | acacccttct | taaggtgggc | tagagacagt | aagttatgca | 2160 |

-continued

```
ggcagccagc tctgagagat cccacgtagc taacctttct cttcccgtag gaggaggcca      2220
aaaacttcat cactcgggag aacctggagg cacggataga agaggccttg gactctccga      2280
agagttataa ctggcggtc accaaagaag ggcaggtggt caggaactga aacagaggc        2340 ctctcaggcc caaataagga cagtgcttgc ctagggactg gatattgggg tagaaattgg      2400
tgcatcccag gagggtggca cagccttgtc cagagcagcc cccattcatt ctagatttgg      2460
caccaggtat agtacctgtt ctgacaccac atacaaactc cggacagcat aaactctgg       2520 gaagttccta tcacacagaa gatcagactg gactgtcccc tctagaagcc aagagctgtc     2580
tcctgagttt cttggaatag tgtgagccca atgtttcctg cttttataaa taaactattg      2640
gaaagcaaag ccttttgtta tgtggcttgc ttttttcttgt tgtagaataa gtttatttgt    2700
cccagttatt tgggtcttaa ggttattagc caaaagccag ttcacctaac tgagccagga     2760
gttagttatc tgctttgctc aatcctgggc tttgctgggt agggtcaggt gtgtccaagg    2820
tccagaaagc aaaaagggtg ccccgttcct cctgggaagg cttccccgtc agtgatttct    2880
gtaaccggac cctgccctga cacagcgtca ttggactacc cagcagacag tagactccac    2940
tctaaacccg cttcttgcgg tcagttgctg tccttcagtg tgtgtaagca gtggccagac    3000
agcacccttg ggtgtcattt caagactctc tcaccttggt ctgctttacg tttggtttga    3060
tttggtttgt tctggttttt gagacgaggc ctttcactgg aacctggcac tcagtattta    3120
gactgcccag ccagctagcc tcagagaatg catctgcgta tgcttgcctg gcgctggaat   3180
tcggtgcaca tggctttgat gtgtaccggg gatcagacac agatgtttca tgagtgcagt   3240
gcatgcctgt tagtggtaga gctc                                              3264
```

<210> SEQ ID NO 17
<211> LENGTH: 44576
<212> TYPE: DNA
<213> ORGANISM: Artificial
<220> FEATURE:
<223> OTHER INFORMATION: COSMID DNA
<220> FEATURE:
<221> NAME/KEY: misc_feature
<222> LOCATION: (1)..(44576)
<223> OTHER INFORMATION: COSMID DNA

<400> SEQUENCE: 17

```
gcggccgcat aatacgactc actataggga tctggtggag gacctatggc ccgcgagcta       60
gagaagtggt tctcaacctt cctagtgctg agaccctta acacagttcc tcgtgttgtg      120
gggaaacccc ctcctgcaac cataaaataa tttttgttac tacttcataa caagtgttgc      180
tactctattg ctatgaattg taaaataaat gtgtcttcca atggtcttag atgactcccg      240
tgaaagggtc attctacccc taagaggtca tgatctacag gttgagaacc actgatctcc      300
agtaaccttc acttgagtcc atatcctcca tgaaggtatg gaagtcaata aaactgagct      360
tcaagcctca tcaaaatggg tccatcccct ggtacagtgt gagtggaaga atacccacca      420
tacggtcact ggaaggagga tgtctgaagg gtcttagatt gtgtcaaggg gtcctgggtg     480
tcaggatctg acgaagcagg ctcgtcatgt ttcatgaaga ctacaggtat gtgataaaac    540
tgcaagctgg aaaagtaccc actgagcccg tgtggctctg ctgggatttg gaggcatgag    600
gagcagaggg tctggaggac agcagtccca gaaataatct atgactaaga aggctgaact    660
ggggtgactc tctggtggaa agagttgcct tttaagaagg aagacatacc aggcatagca    720
acaactgcct ttagtactag cactctgaag gcagaggaag tccgatttct ctgagttcca    780
agccagcttg gtttacacag caagttctag gccaactagg gttacatagt ggactctcct   840
```

-continued

```
caaacggggt tgagaaagga ctcagcagtt agctcagtta actccagttc taggaaatat      900
gatcccttag tctgacctct tggcatgtaa gtggtgcaca tacatatatg cacacaaaat      960
acatcaatct gcaaaggggg agggaggaag ggctggagtc tgaagaaata gttcagtggt     1020
taagagaatt cactgctctt cccaatagcc aaattcagct cctagcatcc atgtcagatg     1080
gcccacgaac acctgtaatt ctagccccta aactcagtgc cccttcacaa gacggggaca     1140
cacgtacaca tatacctaaa aaattaggtg gttttttttt atttataagg tcaaatgcag     1200
aatatcaaat gggttagaca gcagctccaa gctggcctct tcctcccagg gctcttcttg     1260
actcttggca ccctctttgg gtccagaacc cagacattag ccatgactca gctgataaaa     1320
tgcaacccat ggctcattaa ttaggaagtc tgtaattagc ctgtctggta gcctccagag     1380
agaacccctt tcacctgtct tcctcctctc acccagggga agagctcagt tttgcccctg     1440
agacagaaga agggaacgag accatgagca acgggaaatg agatgctggc gcacacacac     1500
tttatgtgtg tgaagtctca gagaggtcac caataatgag gcaatggaaa tgagctgagc     1560
tgcctgaacc tccaagtttc ctccaagaaa accccacagg ggagatgggg catggcccag     1620
gccagctgcc ccagcctctg ctggcagaaa gtgagcccgc tgccatttta atttttgata     1680
cagggtctca ctctacagct ctgggggcct aaaactcact atgtagactt caaactcaac     1740
caaaccaaca acaaaaacaa acaaaacccc tgcactgact ggagagatgg ctcggttgag     1800
aacaatggct gctaggagtc aaacccaggt cctgtggaag agcatgctgg taactgctgg     1860
gtcatcgctg ggtcactctc ttcacacaca cacacacaca cacacacaca cacggcaatg     1920
aactcttcag tgtcttgatt tacggtttct tccgataaat cctcaggagg gcagtcaagt     1980
ggctcatttg gcaaatgctt gcctgagacc tgagtttggt tcccagaacc catggaggca     2040
gaaggaaagg gctccacaaa gctctcttct gaactccata tgtgcacaca cacccacttc     2100
gcacacattc ataatagtga tgaatgaaaa tgaagacaga taaaaaaaac caatttcgtg     2160
aaactgttag cacgttcagt caatggcttt gggggtaacc tgtttcagag ccatggtact     2220
cagtcactag gctcatactg gtcagacgct gaggtcagca atggagagct gctacaccta     2280
aaggtagcag aggtcatttg gctctgactc agaatattcc agctctccac attcacagaa     2340
gttctacttg gtcgtagaaa aaagctgagc ctttttttttt ttttggaact ttatttttttt   2400
aaagatatat ttattttatg tatatgagtg cactgtagct gtcttcagac acaccagaag     2460
ggggcatcgg atcccattac agatggctgt gagccaacat gtggtcgctg gggattgaac     2520
ttaggacctc tggaagagca gtcagtgctc ttaaccgctg agccatctct ccagccctgg     2580
aactttattt tgaacatgca acccaccta ccactatggg ttcagtcacc agcgccttag      2640
gaataaaatt ggagaaaata agctttatgg ttagtcagct gtcagctgtg gggttgggga     2700
cagaagaatg gttatgtttt gttttcccat caaggcctca ctctgtgacc tggttggtct     2760
gccacttgct ctgtagatca ggtttcaatt acagagatcc acctgctccg tgtcgctatg     2820
ctgggataag aactaagtca ccctgcctac cttattactt tgtattcttg ggcatggaac     2880
tcaattcctt gtcagcgaga gaataacttc ctcgatcgga gtgtttttat gtgaattggg     2940
ccaaaaagac tgcgatgctc tgagacctat ttgtgaagcc aagagtagtg ggtagcacaa     3000
gtcagaaatc caaggacttg gtaagctgag acagtaggat gtgtgcgctc atgcacacac     3060
acacacacag acacacacac agacacatac atgcatggac gcacagaggc acccacgcac     3120
atgtgcctgg atgaggcttc agttcttcat aaagctgcct ttgagtttgt gccctcccac     3180
tcttcctgag gactggagtc ctcacacctt gggctgatag tgcaccacta cctttttttag    3240
```

```
tgacctcctc tttgcagtca caggctgaag gtacagggag gactctagcg gccgtctgcc    3300
tctgtttaac atgaacctgc aaggcagtgg gcagcctcac ccctagcgat ggcactgagt    3360
gatgccagga acgctgtcct catgtgccct tggctgttgg ggcacagtgt gcctctgcag    3420
ggccagcctg accgtgtgtg ccagccagaa tgcacaattt ctgcccgacc ttggaagctt    3480
tttgtctttc cttgtgagtt tcttgtcacc cagcagtgtt tcttgcctct ttgcttgacg    3540
cctctatggg aagatggaca agacttttttt ttttctacat cccctgcaaa caggtttgtc    3600
atacctctca ggggcagggg tcttgtccct gtcaagcgca gcaggccacc agacccagaa    3660
ctatgaaatc tacccaactt gtctctgtac aaagttaaac aacaaaaaga aacttggttt    3720 tgttttttgtt ttttttttttg ttttgtttttg ttttgttttt tgagacaggg tttctctatg    3780
tagtcctggc tattctggaa cttgttctat agaccaggct atcctggaac tcaaagaacg    3840
gcctgactct gtctcccggg tgctggtcac tctgaagatc tgtgccacca tcatcaggct    3900
gggttttaaa agattatggt ttatatttaa tgtgtatgac tgttttgttt gcatgtatat    3960
ctgtacatga caggtgtgcc tggtgtttac agaggccaga agaacatacc agatcccccct    4020 ggaactgaag ttacagacag tcgtgagcca tctcggggtt gctggggaca gaatccgagg    4080
gctcttcttg agtagcaagt gcttctaacc gcttaggcct ctctgcagcc cccacttaca    4140
ggatttaaag gtagaacaag gtttgtcacc tgtcctggag accctggcct ttaattccag    4200
aactctggag gtagagacag atgattctct atgaagttca ggcgagcctg gtctacacag    4260
agtgccgcat gatagcaaga agaagatcct gtctttaaaa gagacgagag gggttgggga    4320
tttagctcag tggtagagcg cttgcctagc aagcacaagg ccctgggttc ggtccccagc    4380
tccgaagaaa aaaagagac gagagccagt ggttggtgca cgtctttgat cccagtactc    4440
tggaggcaga ggtagtggat ctctcttgag ttcaaggaca gcgtggtcta caaagtgagt    4500
tttaggacat ccaggattac acgcacagaa accttgtctc ataaaacaac aaacaagaca    4560
agacagaaac tctcctaacg tagaccgcca cacctgattt ttaaaagctc tcagtgaaac    4620
tgagcatggt agcacatgtt tgtaatccca gcagacatgt ggggagacaa aggaatggac    4680
tcagactcag ccggagagca agttcacggc tagactggac cattcctaca atgaggtagg    4740
aattggggtt agcacatcaa gtaagtaacc ctggaaacaa gtttgacttg tccaaggtca    4800
cacagcaatg tctggaaagc taagtctggt tccaaggccc cccttcctc cctctctccc    4860 tctctataat tgaaaagtcc actgcttggc aaaaactccc aggactatat taaacacaaa    4920
tgctggtgtt ctccatgtct tagggctttt atcctagaag gaattcaaac acacaacacg    4980 aatacccccac agaaaggagg gcagggtgga gggggtaaggg agagaggagg aacttcaggc    5040 tactggggt attaaccagc tctgtacccc atccacacag acccaagtta gaaaagagca    5100 ggagagggggg tctggagagg ttgttaactg gcccagcagt ttggcctgct cttgcagggg    5160
cccagctctg ttcccagcac ccatttcagt ggctcacaac ttttaactcc agccccaagg    5220
actctgcttc cctctgagag ctctgtactt aacagggaca cacagacaca tacaattaaa    5280 aaaatgttttt aaagtgagag acgctctaga caggctagca agtattgagt tgtggcaggt    5340
acagctattt taatagtgat ttcaggttag aaccctgggg agggggaacc aggagttaaa    5400
ctatgttaaa tcgaaagac ccaaagccaa tctggtggaa gctgccattg gaggttctaa    5460
caagtctggc ttgtcaggga aaggctcaga atgaaggttt gagctggggc atcattagtg    5520
tataaaaagt atgaaaacac tctaggaaga agacaagagg aggaacacca cggagagcga    5580
gccttacgat gttccagcac gtagacgcca aagtgaagcc aggaaaccaa gcacagggac    5640
```

-continued

```
caggaaagcc caaagttcat tgtgaaaagg acaaaggctt catcctggga aactaggctg   5700
ggagaggccg tgttaaataa agacagacac acccatcaaa atgacccaca gagggcttca   5760
tgattacaat agtatttcat aggcggattt gggcagaaat ctgaatgcag gggattacag   5820
agtaaatgct gacttttgga taagaatggc agatcacagg acaggtgtgt gactcacatc   5880
tttaaagcac actcccaggg cagaggtagt gagtttgagt ttagggctta gtctggtctg   5940
gactggaaat tctatgagac cctgttctca aaaactaaag tatttgggaa aaagaacttt   6000
ctgagggaaa tggaggccgt gtaggtctct ctgggagccc gtgcggcagg tggcgaggga   6060
ggatctgaaa tggggagagt cagcagactg ctggaccttt cctagccagc agagatgcta   6120
aggcaggtga agattaggtc tcatggacct gacacccgtg cacacaggca gcatggcgcc   6180
ttcaaagctc tagtggatgt gattgcccca gacaagtctg ccccaaagct catcttcgtc   6240
cattaataga aaaaggtttt cttctgacca aggaagctgt tctctctgga aaacaatcac   6300
ttaacaagga cattactaac acgaagctgc tgtccgatca catcaccatg acgcaagcac   6360
ttcccttggg gttcatacgc agtgactcag tgctcacgac cctgtgctag gcttggccct   6420
cactcctttt ccgctggaat taagtgggga gtcagacacc ccagaggacc tgcccaagcc   6480
agaaagcttc aagccacagg agccagtgtg tccttggctt ccctacacat gagctgtctc   6540
ttatcctcga tcgagggcct cacagtcatt cctgaaaaga tctggccccc agccctgagt   6600
atggaaggct aacttggcta ccagtcccca ctgtccttat taggaagagg caaaaccgtc   6660
ctctggcact ctcttgaagc atactggtat atccgagaga ggtaacagga gccgatggga   6720
gctgggaggg tcctggccta ggcatagtct agaagacttg ggctaagtag tctgggtccc   6780
caaaccataa cattttttctg gtgactaaag aaaaggagtc tgtaagccta aagcagaatg   6840
tggtgataca cgcctacagt cctagcactg gagaggtgga gatagaaaga tcaagagttc   6900
aatgccagct ttctgctatg tagtaaggtc aaggtcagcc tggactaaac gactgcctta   6960
gaaacaacca aatgacttac cgtctaaagt caggaactac acttgctttc tcagactgtg   7020
tctgtctgtc tggggctcct cccatttcct ctcctaacaa catccacttc cactcctgcc   7080
ttagatctga gatagtacca gcctcagggc atggggtctc cccatagctt ttcctctgca   7140
gtactgtggg ctcacctagg actgtttctg aactatatcc tacccagct ctctacccta   7200
gaaggcctga aactcacaga aattctcctg cctctgcttt ccaatggctg gggttaaaag   7260
catgtgtcac aactgtcctt tttattcttt taatatcgag acagggtctc accaagttgc   7320
cccaagacgc cagccacacc tgggacaggg caggcctttg gctctatgtt cagtcttgac   7380
tccatgactg tggccgctag cccatgaggc tgcgcgtggg aatttccttc tgaaagctca   7440
cctggtatcg atgcttcctc ttatcctaca ccacaactaa caaacctgcc ccacctcctg   7500
gtcctgaccc tgctgcagac ctgctagtcc ttggtgaatg agacctgggg accccctctag  7560
tctgttgaga gctgctgaaa tgctcaacta tgatttccag gtgaccctca agtcggctca   7620
cctccctgat tgcacagcac caatcactgt ggcggtggct cccgtcacac ggtggccagt   7680
gacagcctga tggctggctc ccctcctcca ccaccctctg cattgacagg cccacgtgtg   7740
tccccagatg cctgaatcac tgctgacagc ttgggacctg tcagctgtgg gctcctgggg   7800
agccactggg gaggggtta gcagccacgc tgtcgcctcc tagccaacac ctgcagacat   7860
aaatagacag cccagcccgc tcaggcagca gagcagagct gcacgacgcg tcgatcccaa   7920
ggcccaactc cccgaaccac tcagggtcct gtggacagct cacctagctg caatggctac   7980
aggtaagcgc ccctaaaatc cctttggcac aatgtgtcct gagggagag gcagcgacct   8040
```

```
gtagatggga cggggcact aaccctcagg gtttggggtt ctgaatgtga gtatcgccat   8100
ctaagcccag tatttggcca atctcagaaa gctcctggcc ccctggagga tggagagaga   8160
aaaacaaaca gctcctggag cagggagagt gttggcctct tgctctccgg ctccctctgt   8220
tgccctctgg tttctcccca ggctcccgga cgtccctgct cctggctttt ggcctgctct   8280
gcctgccctg gcttcaagag ggcagtgcct tcccaaccat tcccttatcc aggcttttg    8340 acaacgctat gctccgcgcc catcgtctgc accagctggc ctttgacacc taccaggagt   8400
ttgtaagctc ttgggaatg ggtgcgcatc aggggtggca ggaaggggtg acttcccccc    8460
gctggaaata agaggaggag actaaggagc tcagggtttt tcccgaccgc gaaaatgcag   8520
gcagatgagc acacgctgag ctaggttccc agaaaagtaa aatgggagca ggtctcagct   8580
cagaccttgg tgggcggtcc ttctcctagg aagaagccta tatcccaaag gaacagaagt   8640
attcattcct gcagaacccc cagacctccc tctgtttctc agagtctatt ccgacaccct   8700
ccaacaggga ggaaacacaa cagaaatccg tgagtggatg ccttctcccc aggcggggat   8760
gggggagacc tgtagtcaga gccccgggc agcacagcca atgcccgtcc ttgcccctgc    8820
agaacctaga gctgctccgc atctccctgc tgctcatcca gtcgtggctg gagcccgtgc   8880
agttcctcag gagtgtcttc gccaacagcc tggtgtacgg cgcctctgac agcaacgtct   8940
atgacctcct aaaggaccta gaggaaggca tccaaacgct gatgggggtg agggtggcgc   9000
caggggtccc caatcctgga gccccactga ctttgagaga ctgtgttaga gaaacactgg   9060
ctgccctctt tttagcagtc aggccctgac ccaagagaac tcaccttatt cttcatttcc   9120
cctcgtgaat cctccaggcc tttctctaca ctgaagggga gggaggaaaa tgaatgaatg   9180
agaaagggag ggaacagtac ccaagcgctt ggcctctcct tctcttcctt cactttgcag   9240
aggctggaag atggcagccc ccggactggg cagatcttca agcagaccta cagcaagttc   9300
gacacaaact cacacaacga tgacgcacta ctcaagaact acgggctgct ctactgcttc   9360
aggaaggaca tggacaaggt cgagacattc ctgcgcatcg tgcagtgccg ctctgtggag   9420
ggcagctgtg gcttctagct gcccgggtgg catccctgtg accctccccc agtgcctctc   9480
ctggccctgg aagttgccac tccagtgccc accagccttg tcctaataaa attaagttgc   9540 atcatttgt ctgactaggt gtccttctat aatgacgcgt cgtgcccacc tatgctcgcc    9600
atgatgctca acactacgct ctctgcttgc ttcctgagcc tgctggccct cacctctgcc   9660
tgctacttcc agaactgccc aagaggaggc aagagggcca catccgacat ggagctgaga   9720
caggtaccac tgtggtccgt tcagggctgc tgacagtgcc gtaggaaggg tcatgggcta   9780
ggagagaggg aaaccttgtc tgagcagtca gactttaggg gaggttcctg aaggaagca    9840 gttatcttat atggagtaga tgggtttccc agaacggtaa gagggacca ggtgccagag    9900 aagcccacata aaggacagtg tccccaggca ggggatatgc cagaaaatga gagatactta  9960
tcactgggct tgggatgaga acgggttaaa ctgggtaccc tggcctcctc tgcacagctg  10020
gaggtggccg gtggtatgtt ggctcaccag gactgggtag atggtacgaa actgttctcg  10080
cctgagtaca aagcctttcc cacccagctc aaactctctt agctcctttt ttagccagct  10140
gcaccggttt cttcctgtcc acggaagacg gccattgccc tgtgtctgag cggagtatgt  10200
cccacatcta gcctcagcct cgtgcccaga tctgctgtac tgtatgttca gctctgagtc  10260
tgcccttccg gcagggctga agggaatcca gtcactaggc tcaaatctgg tcaggtcaca  10320
ggtggctcag ttttgaacaa gctcgatggg cagtaggcag ttcaccgagt ctgccttccg  10380
tttgctgagt tcctttggag acttccgagg cactaggtgt gtcttgcacc catcagccta  10440
```

-continued

```
attcggtcct tgccaccttc ctactagggc ataataggtt ggcgggaggt aaaagcccac    10500
cagcgtgggg cagggtaag agtgagcgag ccgtaggtac aggaaagagg atcttggaat    10560
gtgtagggcc atctgaatgt cggagaggta agtctctgag agactgctgc acaccggtga    10620
cacatcagag ctgaggaggt cccccaagtg ttgtctcccc cgccccccgc cccatacgac    10680
tctgtcaaag caggagaggg ttttgagacc tcatgagaac tgatcctcct gataacctag    10740
ccggttagat ttccactctc gccctttacg gctgcttcgt cctagataga gccagagcat    10800
ctggccggtg aagctggat agcagcaggg tgaccttagg ttcccaacgc ccctcttggc    10860
ctggctccag ctgacccgcg tccttccccg cagtgtctcc cctgcggccc tggcggcaaa    10920
gggcgctgct tcgggccgag catctgctgc gcggacgagc tgggctgctt cctgggcacc    10980
gccgaggcgc tgcgctgcca ggaggagaac tacctgccct cgccctgcca gtctggccag    11040
aagccttgcg gaagcggagg ccgctgcgct gccgcgggca tctgctgcag cgatggtgcg    11100
cacaaagcca ggcgggctga gcatgggaa tggatgggt gggtgggagg taaagggggg    11160
ctaagtgggg gactgaggaa tcaggaccgg agatggaggg tgagtagtat aaggggggtc    11220
gagagttgga acgtagcagg gtaggataaa ggggattgtg gggatggcgc ccctataggt    11280
gcgcccaccc caggacgcct gacctcacac agcccttcct tcagagagct gcgtggccga    11340
gcccgagtgt cgagagggtt ttttccgcct caccgcgct cggagcaga gcaacgccac    11400 gcagctggac gggccagccc gggagctgct gcttaggctg gtacagctgg ctgggacaca    11460
agagtccgtg gattctgcca gccccgggt ctactgagcc atcgcccccc acgcctcccc    11520
cctacagcat ggaaaataaa cttttaaaaa atgcaccctg gtgtctgtct ctctttctgg    11580
ggtggggaga aaagggggga gaggaattgg agtgggaact ttctactctg ctctgactga    11640
tccccacatc caaagtcgtg cataagatac gcccccaccg ccagaagggg cagaacctat    11700
aagtcttaga gtataaagga agcttctgct gctcctggat acccacataa tactcagaaa    11760
aaaaggcaag tcagaagaag ggaaagatct gagatccaga ggagcctgaa gggtcaggt    11820 gacttagcaa gtttctatct gagaccgaaa taaaaggaca ttgtggacaa gagaaacaga    11880
gcaggacatg aggagagaca ggatcagcaa gagtgacaga gaaagagggg acaggccagg    11940
ggtggccatc tcagccctga tttcacccag actaaggcaa aaacaacgtg aaggactctt    12000
aaccaaggct gtgcttggat gggaggagaa ggtacagaga cattaccca gacctaaaga    12060 agacaatgcc acccgccttc tctccaggtg ctccaccatc aagacccagc cactgagagg    12120
cagactccag taagagtcca gctacaagtc ctctacaggc acatgttcaa accgtcacac    12180
ccacactcag gcagggaaat agacaagata ggctggagtt gtggctcagg agcagaagtc    12240
ttccctagct atggttccag caccatggag acggaagggg gactgagcgg ggggggggc    12300 gggggggagg aaaaagtagc agctactagg ggcatttcta tgacccttgt cctcaaccat    12360
agctagagac ccagaggaac acagaagtcc agcagcaagg cgcacatgct tgcaatagct    12420
cccagacgta aatacttcat tccgttcggc acatccgggt catcagcact tgactccccc    12480
ccccacactt cttattacct cctcttttt ctaaaatttt agatttattc acttatgtag    12540
atgggtgttt ttggttttgt atgaatgtct gagcaccatg tgtgtgcctg gcgcctcaga    12600
ggtcaggaga gggcatcggg tcccctggaa ctagttacag gtggttacag cctaccgtgt    12660
gggcactagg aactgaatcc cagtcctctt aactgacccg cacatccaaa cccaggcttc    12720
agcccctcat cagcctgtcc ctcctccagg ccctcaggtg tctcccgtct ccggctgctc    12780
tcccagacat ccttccatcc tctggtctcc ctgctcctcg ccctcctgtt aacatccttt    12840
```

```
ctctctgccc catctgtcct gggcatcctc tcctgcgagc tgcagcaagg tcaggatggt    12900
ttacctcatt tgggatggcc tgcaggttct gaggtcaggg gcaactacag agaagagaga    12960
gattagtctg attgacttaa ggtggttcag caaggtcagc tctgcccaga ctcacggtct    13020
tttacccaga tgccagctct cttcccatct cctcggtgcc tatacacctc tctgcatgcc    13080
ccggtttaga caggtagcac aggggccagg cagactccta tcccagcctc ctccttctgt    13140
ggccctctta gggtctgacc tccaatagggg cagggccagg gaagggccag accaaaaagg    13200
gacagaaaga agcgtggcag gcggcatggg cacacttgat tcaacccta cggctggtgt    13260 atgggcagct ttagaatgaa ggtcagattc tcacttcgag cctctgcgca ggtggagtgt    13320
tgtaagcgtc tcgctttcct ccacctgttt ctggaagaat caggctcctc ttcctcgagg    13380
agagaattat acctgctcac cctacttctg cctactggca ataatatata ttttttttcct   13440 ttcagggagt cctttcctca gctacagagc catttaaggg cactcccaga gttcacagca    13500
gatgcttgcc tcctctcttc agcctccaga agcagagagc cttgtgagca aatgccagga    13560
cctctgacct ccacacagac gctgtgctgt gtgcacagcc ctcaagcaca cagcgaagca    13620
atagtgaaaa gtaacttaga ccattttcag gctggggaga tggctcagga gataagagat    13680
cactgctcaa cttgagcctc gggaccacag gtaagaccaa cttgtctgct gcaagagagc    13740
tgcctggtga gattgggaca cacagaggca gagttcatct aggaccgggc acgtcctgtg    13800
tttgccgagg tcccacaccc gcggatcccg gcccgcagca gctctctgct cccagaaccc    13860
gtgagaaaga gacctcaccg cctggtcagg tgggcactcc tgaggctgca gagcggaaga    13920
gaccaccaac actgcccacc cctgcccaca tccctggccc aagaggaaac tgtataaggc    13980
ctctgggttc cgtgggggag ggcccaggag cgtcaggacc cctgcctgag acaccgccgg    14040
aacctgaggg aaacagaccg gataaacagt tctctgcacc caaatcccat gggagggaga    14100
gctgaacctt cagagaggca cacaagcctt ggaaaccaga agagactgct ctctgtacat    14160
acatctcgga cgccagagga aaacaccaaa ggccatctgg aaccctggtg cactgaagct    14220
cctggaaggg gcggcacagg tcttcctggt tgctgccgcc acagagagcc cttgggcagc    14280
accccgcctg gtgaactcaa gacacaggcc cacaggaaca gctgaagacc tgcagagagg    14340
aaaaactaca cgcccgaaag cagaacactc tgtccccata acggactgaa agagaggaaa    14400
acaggtctac agcactcctg acacacaggc ttataggaca gtctaaccac tgtcagaaat    14460
agcagaacaa agtaacacta gagataatct gatggtgaga ggcaagcgca ggaacccaag    14520
caacagaaac caagactaca tggcatcatc ggagcccaat tctcccacca aaacaaacat    14580
ggaatatcca aacacaccag aaaagcaaga tctagtttca aaatcatatt tgatcatgat    14640
gctgcaggac ttcaagaaag acgtgaagaa ctcccttaga gaacaagtag aagcctacag    14700
agaggaatcg caaaaatccc tgaaagaatt ccaggaaaac acaatcaaac agttgaagga    14760
attaaaaatg gaaatagaag caatcaagaa agaacacatg gaaacaaccc tggatataga    14820
aaaccaaagg aagagacaag gagccgtaga tacaagcatc accaacagaa tacaagagat    14880
ggaagagaga atctcaagag cagaagattc catagaaatc attgactcaa ctgtcaaaga    14940
taatgtaaag cggaaaaagc tactggtcca aaacatacag gaaatccagg actcaatgag    15000
aagatcaaac ctaaggataa taggtataga agagagtgaa gactcccagc tcaaaggacc    15060
agtaaatgtc ttcaacaaaa tcatagaaga aaacttccct aacctaaaaa aagagatacc    15120
cataggcata caagaagcct acagaactcc aaatagattg gaccagaaaa gaaacacctc    15180
ccgtcacata atagtcaaaa caccaaacgc acaaaataaa gaaagaatat taaaagcagt    15240
```

```
aagggaaaaa ggtcaagtaa catataaagg cagacctatc agaatcacac cagacttctc    15300
gccagaaact atgaaggcca gaagatcctg gacagatgtc atacagaccc taagagaaca    15360
caaatgccag cccaggttac tgtatcctgc aaaactctca attaacatag atggagaaac    15420
caagatattc catgacaaaa ccaaatttac acaatatctt tctacaaatc cagcactaca    15480
aaggataata aatggtaaag cccaacataa ggaggcaagc tataccctag aagaagcaag    15540
aaactaatcg tcttggcaac aaaacaaagc gaatgaaagc acacaaacat aacctcacat    15600
ccaaatatga atataacggg aagcaataat cactattcct taatatctct caacataaat    15660
ggccttaact ccccaataaa aagacataga ttaacaaact ggatacgcaa cgaggaccct    15720
gcattctgct gcctacagga aacacacctc agagacaaag acagacatta cctcagagtg    15780
aaaggctgga aaacaatttt ccaagcaaat ggtcagaaga agcaagctgg agtagccatt    15840
ctaatatcaa ataaaatcaa tttttaacta aaagtcatca aaaagataa ggaaggacac     15900 ttcatattca tcaaggaaa aatccaccaa gatgaactct caatcctaaa tatctatgcc     15960
ccaaatacaa gggcacctac atatgtaaaa gaaaccttac taaagctcaa aacacacatt    16020
gcacctcaca caataatagt gggagatttc aacacccac tctcatcaat ggacagatca    16080
tggaaacaga aattaaacag agatgtagac agactaagag aagtcatgag ccaaagggac    16140
ttaacggata tttatagaac attctatcct aaagcaaaag gatataccttt cttctcagct   16200 cctcatggta ctttctccaa aattgaccat ataattggtc aaaaaacggg cctcaacagg    16260
tacagaaaga tagaaataat cccatgcatg ctatcggacc accacggcct aaaactggtc    16320
ttcaataaca atcaaggaag aatgcccata tacttgga aactgaacaa tgctctactc      16380
aatgataacc tggtcaagga agaaataaag aaagaaatta aaacttttt agaatttaat     16440 gaaaatgaag gtacaacata cccaaactta tgggacacaa tgaaagctgt gctaagagga    16500
aaactcatag cgctgagtgc ctgcagaaag aaacaggaaa gagcatatgt cagcagcttg    16560
acagcacacc taaaagctct agaacaaaaa gaagcaaata cacccaggag gagtagaagg    16620
caggaaataa tcaaactcag agctgaaatc aaccaagtag aaacaaaagg accatagaaa    16680
gaatcaacag aaccaaaagt tggttctttg agaaaatcaa caagatagat aaacccttag    16740
ccagactaat gagaggacac agagagtgtg tccaaattaa caaaatcaga atgaaaagg     16800 gagacataac aacagattca gaggaaattc aaaaaatcat cagatcttac tataaaaacc    16860
tatattcaac aaaacttgaa aatcttcagg aaatggacaa ttttctagac agataccagg    16920
taccgaagtt aaatcaggaa cagataaacc agttaaacaa ccccataact cctaaggaaa    16980
tagaagcagt cattaaaggt ctcccaacca aaaagagccc aggtccagac gggtttagtg    17040
cagaattcta tcaaaccttc atagaagacc tcataccaat attatccaaa ctattccaca    17100
aaattgaaac agatggatca ctaccgaata ccttctacga agccacaatt actcttatac    17160
ctaaaaaaca caaagacaca acaaagaaag agaacttcag accaatttcc cttatgaata    17220
tcgacgcaaa aatactcaac aaaattctgg caaaccgaat ccaagagcac atcaaaacaa    17280
tcatccacca tgaccaagta ggcttcatcc caggcatgca gggatggttt aatatacgga    17340 aaccatcaa cgtgatccat tatataaaca aactgaaaga acaaaaccac atgatcattt    17400
cattagacgc tgagaaagca tttgacaaaa ttcaacaccc cttcatgata aaagtcctgg    17460
aaagaattgg aattcaaggc ccataccctga acatagtaaa agccatatac agcaaaccag    17520
ttgctaacat taaactaaat ggagagaaac ttgaagcaat cccactaaaa tcagggacta    17580
gacaaggctg cccactctct ccctacttat tcaatatagt tcttgaagtt ctggccagag    17640
```

```
caatcagaca acaaaaggag gtcaagggga tacagatcgg aaaagaagaa gtcaaaatat   17700
cactatttgc agatgatatg atagtatatt taagtgatcc caaacattcc accagagaac   17760
tactaaagct gatagacaac ttcagcaaag tggctaggta taaaattaac tcaaataaat   17820
cagttgcctt cctctataca aaagagaaac aagccgagaa agaaattagg gaaacgacac   17880
ccttcataat agacccaaat aatataaagt acctcggtgt gactttaaca aagcaagtaa   17940
aagatctgta caataagaac ttcaagacac tgaagaagga aattgaagaa gacctcagaa   18000
gatggaaaga tctcccgtgc tcatggattg gcaggattaa tatagtaaaa atggccattt   18060
taccaaaagc aatctacaga ttcaatgcaa tccccatcaa aataccaatc caattcttca   18120
aagagttaga cagaacaatt tgcaaattca tctggaataa caaaaaaccc aggatagcta   18180
aagctatcct caacaataaa aggacttcag ggggaatcac tatccctgaa ctcaagcatg   18240
attacagagc aatagtgata aaaactgcat ggtattggta cagagacaga cagatagacc   18300
aatgaaatag aattgaagac ccagaaatga acccacacac ctatggtcac ttgatttttg   18360
acaaaggagc caaaccatc aaatggaaaa aagatagcat tttcagcaaa tggtgctagt   18420
tcaactggag gtcaacatgt agaagaatga agatcgatcc atgcttgtca ccctgtacaa   18480
gcttaagtcc aagtggatca aggacctcca catcaaacca gacacactca aactaataga   18540
agaaaaacta gggaagcatc tggaacacat gggcactgga aaaaatttcc taaacaaaac   18600
accatggctt acgctctaag atcaagaatc gacaaatggg atctcataaa actgcaaagc   18660
aactgtaagg caaaggacac tgtggttagg acaaaacggc aaccaacaga ttgggaaaat   18720
atctttacca atcctacaac agatagaggc cttatatcca aaatatacaa agaactcaag   18780
aagttagacc gcagggaaac aaataaccct attaaaaaat ggggttcaga gctaaacaaa   18840
gaattcacag ctgaggaatg ccaaatggct gagaaacacc taaagaaatg ttcaacatct   18900
ttagtcataa gggaaatgca aatcaaaaca accgtgagat ttcacctcac accagtgaga   18960
atggctatga tcaaaaactc aggggacaac agatgctggc gaggatgtgg agaaagagga   19020
acactcctcc attgttggtg ggattgcaaa ctggtacaac cattctggaa atcagtctgg   19080
aggttcctca gaaaattgga cattgaactg cctgaggatc cagctatacc tctcttgggc   19140
atatacccaa aagatgcccc aacatataaa aagacacgt gctccactat gttcattgca   19200
gccttattta taatagccag aagctggaaa gaacccagat gcccttcaac agaggaatgg   19260
atacagaaaa tgtggtacat gtacacaatg gaatattact cagctatcaa aaacaacgag   19320
tttatgaaat tcgtaggcaa atggttggaa ctggaaaata tcatcctgag taagctaacc   19380
caatcacaga aagacataca tggtatgcac tcattgataa gtggctatta gcccaaatgc   19440
ttgaattacc ctagatacct agaacaaatg aaactcaaga cggatgatca aaatgtgaat   19500
gcttcactcc ttctttaaaa ggggaacaag aatacccttc gcagggaaga gagaggcaaa   19560
gattaaaaca gagaatgaag gaacacccat tcagagcctg ccccacatgt ggcccataca   19620
tatacagcca cccaattaga caagatggat gaagcaaaga agtgcagacc gacaggagcc   19680
ggatgtagat cgctcctgag agacacagcc agaatacagc aaatacagag gcgaatgcca   19740
gcagcaaacc actgaactga gaataggacc cccgttgaag gaatcagaga aagaactgga   19800
agatcttgaa ggggctcgag accccatatg tacaacaatg ctaagcaacc agagcttcca   19860
gggactaagc cactacctaa agactataca tggactgacc ctggactctg acctcatagg   19920
tagcaatgaa tatcctagta agagcaccag tggaaggaga agccctgggt cctgctaaga   19980
ctgaaccccc agtgaactag actggtgggg ggagggcggc aatgggggga gggttgggag   20040
```

-continued

```
gggaacacca taaggaaggg gagggggag ggggatgttt gcccggatac cgaaagggaa   20100
taacatcgaa atgtatataa gaatactcaa gttaataaaa aaaaaaaaaa aaaaagagat   20160
cactgctctt gcagaggccc ccagttctgt tccccacaac ctcttaggat gactcacaac   20220
cacctgtaac cccatttcag gggatctgat gccctcttct ggtccccatg ggcactgcac   20280
tcatttacaa atactttcac acagagacac atgcacagaa atggaaattt aacagaataa   20340
acatcggaac attaaaaaca aaacaaaaca aaacaaaaaa caaaaaaaac cccataggac   20400
tggagagatg actcagtggt taagagcact gactgctctt ccagaggtcc tgagtttaaa   20460
tcccagcaac tacatggtgg ctcacaacca tctgtaatgg tctcttctgg tgtgcctgaa   20520
gacagtgaca gtgtacccac atacatgaaa taaataaatc tttaaaaaaa aaagcccag   20580 aaagtgatga actctattac caccaaaaag aaaaaaaaga aaaagaaaaa ctcaaatcaa   20640
tcttgaagtc tctttcgcat atctctttgg cctccaccct gtctgtggat cccacatgtg   20700
ggggcggtgg ggcatctgtg ttcatttgct gagtgtgaga gccacataaa gtgctggttt   20760
acgtgtttac ttgttttcta gatgggatgg agcccaggac cttaaccttg tggggcaaga   20820
cttgctctcc tgagctctac ccaagcagtc tggattgcgg gtttcctgtt tgtctgtgag   20880
ctctctgctt tgtggtcatt tgtgcccact ggctcttaga tcccatgact tcccagagaa   20940
cgctgtcctg cagaggcaga cacagggccc ctgagctcag gcccgccct ggagacagaa   21000 acggagaggc cagttgattc ttgatatttt ccgttgtggc ttccttgggg cctgtgtgag   21060
aattcagctc tgtagaaacc ttatggttct gcaactaccc tcccctggcc aagcccttt   21120 cttctagccc gggattaccc cctcaacctc tgaggtcgcc gccaaggtct ccttccagat   21180
atggaagtga ctggatgagt cccttgcggc ctcgcctgcc ttcccatcac ccaggcccct   21240
gtttggcttt gcccttcc acagaagtcc accattgctg tttggacttc caaatggtgc   21300
tcctaagtct gtctgccgca ggccttaccc cagtcgggag tgggaaacgg gcctaactgg   21360
agatgacaac ctgtagagac ccctcggtcc tcctagcagc ctgctgggct gttctccctc   21420
tgaattgcca atgtccatgg cgttcccggt gcctttcctc cctcccgttt ctgacaatta   21480
gacgccagtc aagtttgaaa aggaaatctg ctttatttat ttatttatgt ttttttttta   21540
atttttttct ggtagtggcc atggggaacg aaggaagcgc cctaaaggta tcatcacaaa   21600
gcagggctca gcggccggtc tcagtgctgg gagaaggcgg cctcagggtc gcaggcgggg   21660
tcctcgtggc agccgtctgc acagagagac gccgagtcag ggccgccctg gcccagcccg   21720
cctggtcctg gagccccggt cccgtctcga cccctgcccg actcacccgg gctgcagcag   21780
atgccggcgg cggcgcagcg gccccgctc ccgcagggct tctggccgga ctggcagggc   21840
gacggcaggt agttctcctc ttggcagcgc agcgcctcgg ccgtgcccac gaagcagccc   21900
agctcgtccc cgcagcagat gctgggcccg aagcagcggc ctttgccccc ggggccgcag   21960
gggagacact ggtgggaggg aagggatgag ccggggcgg gaggggagcg gccggggagg   22020
gagaccctgt ggggcggggg gctgagccgg gcgggcgagg gcggccggag gagcgcggga   22080
ggtggcgggt ctccctggct ctctctttgg gctcaaaagc ggtcgaagga gggcagtcaa   22140
aagctcctcc gctccctcga ttcccaggct aggtgggcc ggtacgcggt cagcgcggga   22200
aaggggcgcg cggggcgac cctgtggcag cgggccgggc agcccggaga gccacgggtc   22260
gagggcgggg ctctcaccgt gcgcacgtcg aggtccagca ccgcgcgttt gccgcccagg   22320
gggcagttct gaatgtagca ggcggaggtc aacgccagga ggccgagcag gcagcaggcg   22380
aggctggaac ctgccatggc gttggtgttc agtccgagat cggtcgaccg atccaccgtc   22440
```

```
ggtgatggtt tctccagccc agaccgacct ttttatgcct tgtccactgc catggtgggg    22500
cccagtctaa gagggtgact gcatgactgg tcacagccag gtctcttggg tcaaactgtt    22560
ccacactgtt tagaagcagg cccttcattt gcagggtctg ggctgggtc aaggtcaccg     22620 cctcagctaa tgacctgagc tcaaaaggga cacagcctag aaggggaggc ctaagctaca    22680
agaggataaa gagacttgga gggggtagag gtgcagccta gccaagagct gttttttcat    22740
agaaatccaa tacctcagaa tgaggttgga tagcgcaagt gggtgaggaa gcccttacgt    22800
ggatctaaag cttagatggg gaaaggatc ttgttcaatc tctgagtgca gctcagccct     22860
tcttctaact agcccgtaaa acaaaatatc agtagaaatc aaacccaaaa acacaacaaa    22920
cagaccaaaa taaagtaaaa agaaagaaaa atcacaataa aaggaaaaat cacacttgca    22980
cttacaactc tgtattaggg ctggagagat ggctcagtgg ttaggagcac tgactgctct    23040
accaaaggcc ctgagttcaa atcccagcaa ccatatggtg gctcacaacc atctgtaatg    23100
ggatctgatg ccctcttctg gtgtgtctga agagagctac aatgtgctta tatataataa    23160
ataactttaa aactctttaa aactctgtat tagaacttgc tatgaggacc aggctggcct    23220
tgaactcaca gtgatctatt tgcttctgcc tcccaaatgc taggtaccta cactcccgtt    23280
tgagaaaaca caggccatca gctgcttgag cgtggccaac aggcggcctc agctacagag    23340
agccatttgt cctaaggcca taccttcct ggtggccaca tgtaatggtg gcccatttta    23400
gtacatacaa ctaggcatct cgtgttgcat ttcaggggttg ggctgcaggc ctgcataggt    23460
ctgcatggga agaatgctac atgcagctca gtagcagact gcctgcctag tgtgtgagag    23520
accttgggtc cagtccccag catggtggta gcaagacatt ttgggaacag ttttttgcttt   23580 aaattttaac ttttatttgt gtgtatgttt gtgtacacag gtttccttgg caaccagaag    23640
aggatgttgt atccccagga cgtgtcatta aaggggatca tgagtaggcc tatgtgggtg    23700
ctgggaacaa aattcagaat tctgcaagag cagtgtgcag acttaaccat taagccatct    23760
ccccagctcc ttgattttgc atttgaatac agtttaaaat gaaatgcaca ttaagccacg    23820
gtgacagtga tgcaaacttt taatcccaga actcaggagg cagaggcagg agaatgtctg    23880
tgagttccag gccagcctgg tctacagacc tagttccagg ccagcctggg ctacacaaaa    23940
aaacaaaagc aaaaccaaaa caaaataaag acacagacaa accatggcag gaagacatgg    24000
gagcctcaac ctcttcattt gacggctgag aaatcgaaaa cagatgacca ggagagacca    24060
aggtctcact gctgccttca aggcttgccc tcagtgactg gaagatgttc cactgggccg    24120
catcttaata tcttaccatc tcagggctgg agaactggct gagtggttga gttgctcttg    24180
cagaagtcct aggtttgatt ccgaggaccc acagggtggc tgagatcact tatcccagtt    24240
ccagtggagc cagtacccaa atagtgcatt acacacttgc aggcagaacg ttcagacaca    24300
taaaataaaa taaatagacc taaaaacatt taaaagaaag gagaagcatt atccagagtc    24360
gttttatttt gttttgagat agactcttag ttgacctggg actgtctgtg tagactaggc    24420
tgggcttgaa ctcacagcga tcccctgcc tcccaaagtg ctgggtgtac caccgtgcca     24480
ggtacctagg cccctgttta agaagacact tgccatcagt ggctgggtgt ggtcttagct    24540
gcagaaagcc acctggccct tcccaggtgt ccacatataa tggttggtcc actttggtac    24600
gaatgctggg caccccaact gcatgtcagc tttgggcttt gggttagctg aggtctgcat    24660
actggttcta gttgcccacc ccttctcttc catagaggtg gggcctaagc ccgtgttcta    24720
aactccatct caggctctct taagaagtga cctgcgacat ccaggaagaa gtaacagcca    24780
gtgcccccga gacccactca ctacatgcag tctcagcccc tagagaggat ggaaaagcct    24840
```

```
ccggtctcct tgttcttatg atcagccttc tcctcaagga gctggggcca gtggggcaaa    24900
gcacattctc ttctgaccct gaatcacaga tcctgagtca ctggtgcaaa ctatcaagcg    24960
ctaagttggt ggtgaggttg acctgtacta caaatcactt catttctcac ccagactagc    25020
ttattggcat tccaggcata gaaagccaag agcttgaccc ccactatagc cccagagaga    25080
cagcccacat agtctgtggg catagtgatc tcatcttagg taatccatgc acataaatta    25140
gcatgtcttg ataatacata cctaatgctc ctgttaggcc agcatgccta acatgctcac    25200
caacccaatc tgtgtttggg aaaggccaat attccgcaag gcagaatgct agtccttcag    25260
gaatggggct gcagctggac tggggagaac acactgaggt tataagagga ccattgaggc    25320
ctaatagcca aggtagagta ggcggagcct tgggttacag tgttcagcac caggaggaaa    25380
gagtcactat caccatgggg ttcatctgtc actggaggaa gcagaatatg aactaagagg    25440
catattatgt tgggttacga ctttagttaa gatctgagtg tatcccatgt gatacattgt    25500
cagtccttag gaagatgtct tgggagatgg tgagatcttt aagatagaga cccagtgtca    25560
ggttctttat gtctctgaca gcatgcccat gaaggaagtg gtctctcctg gatctctttt    25620
tcagttttgc aggcatggga tgaaggggtg tatccttccg tgtgcttctg ccatgatgtg    25680
tacttcaaca tagacctgta aggaacagtg gctacagatt gtggactgaa gtctctgaga    25740
ctgtgagtcc aaataaccct ttctttctag gcatggcggc acacacctgt aatctcagca    25800
tgctggaaat gtgcagcagg atcaggagtt aaagaccagt ctcagataaa tgacagttca    25860
aagccatcaa ggggataatg agatacttcc tcaaaaacca tcaaattaaa acttttgttt    25920
ttatacatta caacttgtca ggggttttgc tatagtaatt aaaagtcacc acaggaaaca    25980
aaggcacgta aacatagcaa catgtgctat gtttaaggca acatgtgcta ggaaggtaga    26040
tatcaccatg ctgggtgctt agaccagggc tatgtcgagg tcccggagga gagctgagga    26100
agccctgggt gaatgtataa tgtatcacgg gcctcagacc tgtgagatct ggcaaagctt    26160
ccccctgcac gctgtgggtg aggtgaatgg ggattcggca gagcctttgt ctggtctgag    26220
tgcaaatgct gacggtatgt tctagtggag gtgtttacaa aggacgggcc agtgtgcgct    26280
ttagccatag aagtggtggc tccctgatga atgtccacaa cctgggattg ctgcccacaa    26340
gatcagccag gccctctcct gcgctgtgca gagtgaacac acggaggttc tgggctgctc    26400
cagtggctgc taccattctg ccagagagtg cacaggccac ctgaccccag cctttctgtc    26460
catgtgtctg tccttttcttc actctctcac caccttgtt agggtcccag atccaagtta    26520
tgtagggggt ggattaggaa atgctatggg atgagaggca gtgttggttg tcattctcct    26580
tagggtaacc tgtgagtatc aaggaaagaa agtgtacacg cagaaggctc accgtgctgc    26640
tgctatgtac aagtgagcac aaatgtaacc tctggaaata cccatttatc atgtctgttt    26700
tgggggcaga gcccaggcag gcgtttctac tcatggtcct aggagcagcc tctcctcatc    26760
tggtatgcag cccttcctta tccgagacgg agcctggtgc cggacacag gtcatttccc     26820 tgcagttgta tattatttgg gcagctcact tctttaaaat attttttgaaa aaattatgtg    26880 tatgagcctg catgtatgtc tgtgcaaaat gtccacagag gccagaagaa ggtgtcagac    26940
cccctggaac tgggagttcc gggtggtcgt gtttggcata tggggcctgg aaaatgaacc    27000
ctggtctcct agaagagcaa ccagtgcgct cagctgctga gcacctctcc aactcctgct    27060
tctctggact gggagacaaa ggaaaagtga gagactgatt ctgttctgtc aagtctctga    27120 gcataggaa gacctaggtt cattctatgt catctgtctg tctgtctgtc tgtctgtcta    27180
tctatctatc tatctatcta tctatctatc tatctatcta tctgagacag gatttcacta    27240
```

```
tgttagcctt ggctgtcctg gaactctatg tagacaaggc aggtcttaaa ctcgcagaag   27300
atcctggtgg tctctcccca ctttgcctga ttaggctcac ttttaagggg aatgaaatgg   27360
gctgggtgtg gcagtacaca ccttgctctc agcactccga ggcacagaaa ggcagatctc   27420
tgagtttggg gccagcctgg tctatgcagt gagctatagg caagccaggg ctacatggta   27480
ggaccttgtc ttaaaaagag ccccaaacaa atagctcact tgcccaggtg aggtccacca   27540
gcatctctac attttgaccg gaagctaaga ggaatcttta ttacatcacg cctgccacag   27600
tctccatctt tgttgcagct ggagtgctcc cacagggctt ccactgcacg cactgcaccc   27660
gaagggcttc cacttcacg cacttcaccc gaagggcttc cacttcacg cacttcaccc   27720 gaagggcttc acacttgatt cacttgaccc gaaggggctg acactgcttg cactgcacct   27780 taagggctg acactgaccc aatggcaccc gaaggggctg acactgaccg cactgcaccg   27840
aaggggctga cattgcacac gctgcaccca aaggggctga cacttgctgc actgcacccc   27900
aaggggctga cacttgcacg cactgcacct accaagggtg acactgcacc tgctgcaccc   27960
aagggggctg acactgcatg cactgcacct accggggctg atactgcacc cactgcaccc   28020
aggggggctg acactgcacc cactgcaccc aggggggctg acattgcaca tgctgcaccc   28080
aaaggggctg acacagcacc cactgcaccc gagggagctg acactgcacg cactgcacct   28140
accggggctg acactgcacc gcttgtaatg tacattactg ttttttttt ttcttttctt   28200 tttttcagag ctgaggaccg aacccagggc cttgcccttg ctaggcaagt gctctaccgc   28260
tgagctaaat cccctacccc tacattactg tttagaaaca aatttatggt ccttctcaca   28320
tgctgcagga gattacacaa agttgggggt tatcaagaat gtggatcacg gtggatcatt   28380
ttagcactgt cccccccaca gaaagggtca tttctagaca aagaaaata gtttatatgg   28440 aacacttctg ggctgggcag tggtagcaca tgccttaaat cccagcgctt gggaggcaga   28500
agcaggcgga agcacgcgga tgcacgcgga cgcacgcata tctgtgaggt ttaggccaac   28560
tcggtctatg cagcagcttc caagacagcc aaggctgtat ggagaccctg tctcggggtt   28620 ggtgggaat ctcttcaccg tcttggtcac ttctttatgt gtgagacaca tagacgtttt   28680
tcttctgaat attttattgc tgcttgtggc attcacaact tagggaaaaa ttgttaaatg   28740
ctgcattccc agcacttgag ccagtgaagt tcaggcctcc gctcgtcttg taatggtatt   28800
tgcacagggg atgccttggc tgagtgagtt cttccagaaa actcctgggc ccttaacacc   28860
tatttccagc atttggaaat ccgaggcagg aggattgaca tgagttgcag acatagtcag   28920
ctagaagtgc agcattaaat cctatcttaa aataattatt agaataattt aggggggaaaa   28980 gcctctaata gagatgggag agtgtgcgca tgactgccct actgtgtgct tctagaaatc   29040
aatatgaatg ggccagaact agagaaaagg ctgtgagagg ctgtaccctg ctgtgtgcaa   29100
cccacttccc tcctactatg tgggtgctgg gcatgacacg aggttatcag gctgggtgac   29160
aagcaccctt acctgtgggc agtcttgctg gtccaaccta tttgcatttg aatcccagct   29220
acttcaaacc ccatgggtgc atatttaccc acttttggtt ttggaaacag gatcttaaaa   29280
taaacaggtc tcactctgta acccatgctg gcctgaattc agcatcttca gcctcagtct   29340
cccaagcgct acgatttcct atgtgccata tgtcacaata catgcacttc agttttgtca   29400
aaagaagtga accaggaata actggtacct acctataaga ctgctgtgat gaaggaggac   29460
attgtgtaaa acgaaactca ggatatagta agtgctcaac acgtgttaga catgttggtc   29520
tccatgaggg cacaaaccca gggcctcatg catgccaaga attgggccta tcactgagct   29580
atacaattag tccctatgac ctactgtgac ctcagacgca caccatggat ctgacattgc   29640
```

```
atcaaatcag aaatgaattt ctgaaagact tgctcatagc atgccctccc acaccccgt    29700 cccagccccc cctctcactg gcaaggacat ctcactgtgg tggtggcagg gcctctaaaa    29760
catcatagga tagctgagca gcagtggcac atggcctctc agtcccagca caggggaggc    29820
agtcagcctg gtctatagtg taagctccgg gacagccagg gctacataga gaaaccctgt    29880
caaacctacc ctacttaaaa acagaagtag agcagtagtt tggattacac tgctttgaca    29940
cttggtgggt agcatgtgtg cacctgccca ggagctatct ggattctcaa atggaagaca    30000
cagacacaga cacaaacaca aacacacaca cacacacaca cacacacaca cacacacaca    30060
cacacacaca cacaccagtt aacttttgac acgccatgac tagctcaaag gctagggact    30120
cccaaacctt cccctgtcag caaatgctcc cctctggtac tcctgagact aagctaagcc    30180
ttcccctgct gtcccaggcc caacggagga agtgagcatg gtcacttacc tgattctttt    30240 ttttctttt ttcggagctg gggaccaaac ccagggcttg cgcttgctag gcaagcgttc    30300
taccatgagc caaatcccca accccacata ttctgattct tacatggctg attggctttc    30360
tgtccctgca gttcttacat cctgtccttc ttccctgaat catgaggacc ctctcctctc    30420
tctctctctc tctctctctc tctctctctc tctctctctc tctctccctt ctctctgtgt    30480
ctctgtgtct ctgtctgtct gtctgtcaca cacacacaca cacacacaca cacacacaca    30540
cacactagcc catgcaaatc taagggcccc ttcccgtctc cctttgcctg accattggct    30600
cctggcatct ttattgatca atcaaaaacc aattgggat aaggacctac agtgtttgga    30660
catgaagatt cctaatttgg gggctgcatt aattcaaaac attggaacca attcccaaca    30720
acaacaacaa caacaaataa agcaaagaaa aaagtttaca acgctgcctt cattatttga    30780
gaaacaaatg taaggaaaac catcaggtat ctggactttt aaacggccgg gattagaga    30840 ctctgggatg ttttctgtgt tggggattga agccagggcc ctgggacatg gtaaggaagc    30900
actgtaccat gaaactacac cccagagtct gataaggcta ctgaatgaca attaaagatt    30960
cataattgct gaaattctgg aaaactctaa gctaccaatt ttgtatatgc tcaacttggt    31020
ttcctgaaaa catctgaggt tcttgcacgt aacttttcct cagagcaagt acaactaaat    31080
tctgactttg tgacaataaa gattgtcagg aaaggctttg tgaaaatgtt cagtccccag    31140
gagacgtgcc ctcctgcagc ctgtgaatgg cggccaggtc acaagtcagc agatgcagtg    31200
gaacggagtg tggtacttct gtgagacact gcaggactgg atggatggct tagtagttaa    31260
gaacatgggc tgctctccca gaggacctgg tttcaattcc aagccttggg ccctgcaaga    31320
accttatata gactggcttc aagttctcca tgtagctgaa tatgacatta aactccagat    31380
actcctgagt cctaggttta cagctgtgta cagctatgtt tcttccctga cgaccccgca    31440
gcccccattt tgagataggg atttaggtag cccaggctgg cctcacactg actaagtgag    31500
actggcttta aactcctcat cctttaaggt accaccatga atttgctgta tagctctggc    31560
tggccttata taatgtagac tagactggcc tttaacttta aaattgtgca ctttatttt    31620 ttttaaatta tgtattttat gtatatgagt atactgtagc tgtcttcaga cacagggcac    31680
cagacctcat tacagatggt tgtgagccac catgtggttg ctgggagctc aactcaggac    31740
gtctggaaga gcagtcagtg ttcttaacct ctgagccatc tctccagctc tctgcttaat    31800
aagtgctggg atgactagca tgtgtcaccc tcctggccac ttctggtgtc tccttttccag    31860 gcttttaaaa attatctgtt ggcatgtcca cacagggtta tatgcatatg aacgcaggtg    31920
cctgtgggct gtcctgtcct ggaactggac ttacagatgg ctgtgagcca cttgatgtgg    31980
gtgcctggaa actaactggg ggtctgaaaa agcgggaaga actcacatga ctgtggagtc    32040
```

```
tgctacccct tttattataa aagaaaagaa gatattttaa cagcacgtat gagacacaag    32100
tgaaagctgt ggccatggtc ttcagggatg gttaggtcct gcaaaactga aggaggtggg    32160
ctctgggtgt tggtcacatg gtagattgat aggccctggg ttcaatcccc acctctgcat    32220
aaagcaggca tggtggttca ctgcctgctt ttagaggaag aggcaagagg attggtagaa    32280
tctcaaggtc attttcagct acatagcacc agtcaaatct ttgagtccaa gaccagcctg    32340
atctgtgtac tgagttccag ggcagctaca tagttgagac cctacttaaa atttcaaaca    32400
acaaaaccca caaggtttaa aaactctatc acttttagtt atgtttgtgt gtaagtgttc    32460
gtgcccacgg aggttagagc actgtatccc ccggagtggt gagcgggctg gcatgagtgc    32520
tgagggctga attcagcatc tgtgttcaac atatttgtta aagcacacga agaggaaatg    32580
gccagtgtca acaggagccc agccaggctt ggggtgggaa aatgctttga cttctatctg    32640
gcaagaaaaa aacaattcca agtttgatcc ttgccagact cttggccttt accaggcttt    32700
cctcacagag tctgctgtaa ctgtttctgc aaattcgcag aggaacctga gatctcaggg    32760
cacgttggat acccacgtgc tggagaaact gaacaatgac tttaggtttc atcgtgcctg    32820
gatgaaacat gaaaatacccc cacaccgctg agctgacaaa tgtgcctctc tctctgtagc    32880
ccttcagtca gctgagcagt ttgccctcgc tcggctgcag taccagcaca ggcacccccag    32940
tctccccgat gagcggtctc atgaggattc aggttggtct cgaactccct atgtagctga    33000
aaatgacctt gagattctac caatcctctt gcctcttcct ctaaaagcag gcagtgaacc    33060
accatgcctg ctttatgcag aggtgggggat tgaacccagg gcctatcaat ctaccaagtg    33120
aacaacaccc agagcccacc tccttcagtt ttgtaggacc taacctagcc ctgaaggcca    33180
tggccatggc tttcccctca gcacccactt atcatgaagg ggcaagggtc cagtttcttg    33240
gttaagtatc tacgcttgtg actagggaga tacatcctgg gcaggagtga agggttaccc    33300
attcagcagc agagttccta ggtttactgt gacaacaaag atctaggaat ggcctaggtt    33360
gtcctgacat gatcccatta gcctacctca gatatctgaa tgcaggggct cactgtgtgt    33420
cccagtcagg gacagtattt actaccctaa agtgggttac agctctcggg gggggggggc    33480
tgcgtgcagg acgacacctg caccttcaca cttgcttctt caatggagta agaggctgct    33540
aacatcccca aggtttccat ttcagctagg atgagagtct ggagttcatg tccctggtat    33600
tcaagtatat gacactgaag agcaaagagg cagagagctc atccactaac aggcatgcac    33660
tgcactcatg aacatctgtg tctgatcccc ggtacacatc aaagccatgt gcaccgaatt    33720
ccagcgccag gcaagcatac gcagatgcat tctctgaggc tagctggctg ggcagtctaa    33780
atactgagtg ccaggttcca gtgaaaggcc tcgtctcaaa aaccagaaca aaccaaatca    33840
aaccaaacgt aaagcagacc aaggtgagag agtcttgaaa tgcacccaa gggtgctgtc    33900
tggccactgc ttacacacac tgaaggacag caactgaccg caagaagcgg gtttagagtg    33960
gagtctactg tctgctgggt agtccaatga cgctgtgtca gggcagggtc cggttacaga    34020
aatcactgac ggggaagcct tcccaggaga aacggggcac ccttttttgct ttctggacct    34080
tggacacacc tgaccctacc cagcaaagcc caggattgag caaagcagat aactaactcc    34140
tggctcagtt aggtgaactg gcttttggct aataaccctta agacccaaat aactgggaca    34200
aataaactta ttctacaaca agaaaaagca agccacataa caaaaggctt tgcttttccaa    34260
tagtttatttt ataaaagcag gaaacattgg gctcacacta ttccaagaaa ctcaggagac    34320
agctcttggc ttctagaggg gacagtccag tctgatcttc tgtgtgatag gaacttccca    34380
gagtttaatg ctgtccggag tttgtatgtg gtgtcagaac aggtactata cctggtgcca    34440
```

```
aatctagaat gaatggggc tgctctggac aaggctgtgc caccctcctg ggatgcacca    34500
atttctaccc caatatccag tccctaggca agcactgtcc ttatttgggc ctgagaggcc    34560
tctgttctca gttcctgacc acctgcccctt ctttggtgac cgcccagtta taactcttcg   34620
gagagtccaa ggcctcttct atccgtgcct ccaggttctc ccgagtgatg aagttttgg    34680 cctcctccta cgggaagaga aaggttagct acgtgggatc tctcagagct ggctgcctgc    34740
ataacttact gtctctagcc caccttaaga agggtgtcaa aagagcccag ggccccttg    34800 agtgtcccac caataggcca gcacaactgt actaggtgac ctcaaccatt atatccctct    34860
tcctcggaca attacccatc agatctctca gccacaaccc aagaacgaat cgaatcgtga    34920
caacctgatt gggggcgggg ggaggtgcgg ggtggtggac tctctcaacc ttgtcactct    34980
cccttacaca ataaaaacag ctccattctc atttatggtt tccctgacct tcaagtttca    35040
cacggcaata ctagcctgta acctttcatt gaccattgtc tgggaggcac tctgtgtgtg    35100
cagagcagag agagaagcct cctgaagact ggtcacttga caccctgtgc tgctctcccc    35160
agagcctccc tcaccggaat ctccaatacc cacattcctc acgacctcgg cccacctgca    35220
gtttgagaac ttcttgttct ttcagttgca cccaagcctg ctcctcctgg gccctctggg    35280
cctggacctc agcctgccgc agctcctggg cctgtgcttc gagctgcaac ctagctatcc    35340
tgcgaggaaa aaggagccga gaatgagcgg ggccgtgggc cgcgcacggg cagaaggagc    35400
agggttgggg gctggccccc gggccgcgcg gccaggcggt tcaaagcccg caacatgaca    35460
gctagcgcct gcgccctgtc cggaagtggt cgaggagcat cacgggaatc tcctgtcccc    35520
gcccccgtag gcggagctct tgctgtctgg cccatcgcgt ccctggagtc tcgggtagag    35580
tgggagggtc gaggggcacc ttggagacca cagttcgctg ggctgtattg cccgccaatg    35640
acagctacaa caccaggcgc tcttgcctac ttgttcacaa gcttggacac cgccccaaag    35700
cgtgtggttc tctggcccac cggtggcctg tgtacccttc cagggctgat gcaagaaatt    35760
ctgagcttct agctacttaa gttaggctta cacttcctct ttgagtaagc gttctcctga    35820
tgcactttaa actttaggtt tgcaatcgag caacaaacct tttccttgca ttgcactgcc    35880
ctgttgtggt cttgggcagc tctgcaatta attgccagag ttctcagtat cagtgatcac    35940
ttgttttcta ctgggtggcc tgtgtgaggt gacgcttgtc ctctttcacc tgagccgggg    36000
tcttcccacc ttgagaccat ttatgaagct tttaaagtac tatcttcctc tacaatgaag    36060
agaaacagga ggcagtgcag ggcagagagc atctgtccca aaggtagatg gctctccctct   36120 gggagagttg ttggtaatca gaagctgacg gtgagggcta gggaactgaa gtctcatcct    36180
actcattagt gttgtcaaca ccagattctg cagagaatct gcacttagga gggtctgagg    36240
agcctgggct gactgcaata cctgatattt ctcagaagag aacagagtct gcttacatcc    36300
ttctcccaac ttccaggccc gtaggaggcc cagccagcac cctcttcctc tcatctcacc    36360
ctaccctgga gtgacacagg gttgctctga acatcaggga acgtggcact cccatccttt    36420
cttgcaacag gtctcactat atagctccgg atggtctgtc acttacaatg tatatcagac    36480
tcacaagagg tccatctgcc attgcctcct aaatgctggg gttaaaggca cataccacca    36540
cacctgtcct aaacctttct tcttcggggt catcctagat aaccagtatc tcatttcaga    36600
taacttcagt gtctgggcaa agagaatatt tctatggtgt gggtcattcc tagaggcttc    36660
ctaaccttgc tggctctgac gttctctcgg ctggtcaggt ctactcatcc ttctttcaga    36720
gggtttcata agttgtaaga gatttaggcc tacggtggat gaaagatgtg gagtcatttt    36780
gagtagctaa tgctacagaa ctagaaggca ggttctctgc cccccttctct gacctgttgg    36840
```

```
ggaagtggaa gtaactttcc atttgtgacc ttccccacta ggtggcgaga tagaattgtc   36900
aaagctggga aaggaggctt ttctgggcag ttcatgggta gaaggacaga cagacagagt   36960
tggaggaatg gaagcctcct catttaccaa ggggtaaact atggatgagg tgacttcagg   37020
tgcctgcagg accctatgca gacggtccca ggatttaatg atcaggccat tctatttcct   37080
ctggtgtcaa atccagtgat atcattaaaa caaaaacaaa aaagcccaa tcagggtctt    37140 acttgatggc cttatatttc caacaaagcc caggctggcc ttgaacttga agcaatatcc   37200
ctgcatctgt ctccagagtg ctaagattgt gtgtgtcacc ataccaaggt acagtgatct   37260
cttgaaacag ggaggtgcaa gtcattactc aaacccctcc tcacaatgtt ctatgagcaa   37320
atccgaagtt gatgttggct tttaaagtca ccagacaagt gtccttctgc ttagatcttc   37380
ctaggaactg aggtttgaaa caaaagcat aacatggttg gagagatggc tcagtagtga    37440
aattctgaat gtggttccca gcatccacat tgggcacctc agaatggcct ataacttcaa   37500
ttctagggac caagtaatct cttctggctt atgggtgtca ctcacatgca tgtgtgcata   37560
tggtgcctaa gtaaaaaaat aatcttttaa aagcagattt taaaaaaaat ttcaacgatt   37620 ttttttttaat gttcattggt gttttgcctg catgtatatc tgtgtgaggg tgtcaggttt   37680
ccaggaactg gagttacaga cagatgtgag ctacctgttg gtgctaggaa ttgaacccag   37740
gtcctctgga agaataatca gtgctcttac ccactgagcc atctctccaa cccaaataca   37800
tcttaaaaaa aattaaaaca gtggacctgc cttctagttc tgtagcatta gctactcaaa   37860
atgacccaca tctttcatcc accgtaggcc taaatctctt acacttatga aaccctctga   37920
aagaggatga gtagacctga ccagccgaga gacatcagag ccagcaaggt taggaagcct   37980
ctaggaatga cccacaccat agaaatattc tctttgccca gacactgaag ttatctgaaa   38040
tgagatactg gttatctagg atgaacccg agagaagaaa ggtttaggac aggtgtggtg     38100
gtatgtgcct ttaaccccag catttaggag gcaatggcag atggacctct tgtgagtctg    38160
atatacattg taaaggggag aactcccgga atttgttctc tgacctacac atgtgacatg    38220
catgtgttcg tgcacacaca catacacaca cacacactgt aaaaatgcaa aatggctacc    38280
aagtggtcat tgagcttctc aacctcactg acagctacat tattatatag acttactggg    38340
aacagatccg caggaaatta tttggaatct ttttcttttc tctaacgggg gctgatctgg    38400
aacttctgag ccttttttgtt ccctatcatg aatgctggga tggcaggcgt ttccacatga   38460
ctcgttcgat gtagtattgc agactgaacg caggactttc cacacactaa gcaggcattc    38520
tgtgaactgt tacgtctcca gccccatttc taaattctaa caccaaagtg ctagttttgt    38580
cccttgacct ggacactgca gtgagttcac agaacttata atcaccctgt ttagtgtaga    38640
agctacctca atcaccatga cattttttcaa aaatgtgttc actttcctct ttagagtcca   38700
agcacaccaa gcttggcgga acaatgatac agtctaactg gatctgtttc aaaattgcaa    38760
cttgactcta catctaaata ggtatgtgtt gtgacaagtt tattatgttg tgtgtgtgtg    38820
tacacatgtg ccacaggaag ccaaaggaca acttgctaga gtgcattttc tttcctggga    38880
attggcctct ggttgtcagg cttggtagca cgcactttga ccctctaagc catcttgatg    38940
gcccagagag tgaaccacgc tgttttcact ttcctacttc ttgggctgaa ttctcaagta    39000
cctgcccttg cagctttgca cccttcctaa cttcaaaagg aaactgacat ggagaagggt    39060
gatacttgag gatttcctgg ctcacttagc tcaggactct ggcctaagaa cagggaaccc    39120
agcagtgtga acagggtcc aagagagttc atttgtactt accggcaaaa cagtgtggca    39180
ggcttcacac aaatacatac tcggcaccag gacagggcca ctctggatgg aggtgggctt    39240
```

```
aggtggggta ctgcccaccc agggttgtcc tctcttgtaa gcagactcat ggggacagcc    39300
cagaagtgat cccacagtct ctctgaagct gacaataggg gataattcta agtcctcatc    39360
ctgtgctcat ccacagtcct ttgtcgatct ggacactact atcatgggct gctggaaaca    39420
ggtctttgca gcccaagtct gagccactag ctctgctttc actgccagcc attaacctcc    39480
gggagtgggc gtgggataag aagaaacatt tatagagtca acggccaatc tgtatttggg    39540
ctgaaaacca tattaaggaa gggccaagcc tggcataatg gtgaccagag ccactagggg    39600
accaactgca cccagctttta gcaaagtgac aggcagcatg aggtaccatt atgtgtgctg    39660
ggcatgcggc ttcaggatgg ctctgtgacc tcctagaggt tgtcttattg gcaggcatag    39720
gaaacaaagg cagagaatga atgctacagc cagagagacc cagatctgct aagtggatga    39780
ctcttgtaca tatgtgtgta tgttgttttt gaggcagggt ctcactgtgt agctctgact    39840
gtcctggaat tggatctgtt ggtctcaagt tcagatccta gtggtttatt tttcctgtgt    39900
atgtgtgctt gtcatgcaca agcatgtgtt aaggtgagta gatatgtagg cacatggaga    39960
tcagaacaat ggtgtcactc caaacctttta tagacctata tccatcttga cattagggtt    40020
acaggtgtgt tcaacataga tatggccaaa atttaatgtg ggttctgaag atctaaatat    40080
gtcttgtgct ggctagttct acgtcaacct gacacaagct agagttatct gaaggaaggg    40140
aaccttagta gagaaactgt ctccatgaga tccagctgta tagcattttc ttaattctta    40200
gttagagact aatgggggag ggcccagtcc attgtgggtg atgcaacctt agacaggtga    40260
acctgggttt tgtaagaaag caggctgagc aagccatgag gaagcaagcc agtaagcagc    40320
actgaccatg gcctctgcat cagctcctgc ctccaggttc ctgccctgtt tgagttcttg    40380
tcctgacctc cttccgtgat gaacagtgat atggaagtat aaccaaataa accctctcct    40440
cccaagttgc tttggtcatg gtgtttcatc acagcaacag aaagcccaac tgaggcaggt    40500
tttcatgctg tataacaagc tgaaccatct taccagctcc atagtgttta ttttaaaaga    40560
tgagtgtgta actttccttt ttttcctttt aaaaatccaa agaaccacgt tcctcaggaa    40620
aagctctggg ccagttctcc tggtaacttt gaagtctttt taaaggcaga gtctatgtta    40680
gacaagctgg cctcaacctc acagagatca cctccctctg cccgttaact gcctggtgag    40740
ctacaatgtg tttttaaaga tgtccctgtt ccctcttaaa caactccaat ttcacccatg    40800
tgttcccatt tggtaggaca ggaagccatt tgttcatcat gaagcttctg ctgatgtcag    40860
gacaggcgcg cgcgcgcaca cacacacaca cacacacagc agctttagtc atttgtggtc    40920
agctgggaaa atgggaaaac acggttggag ctgagttgaa ctgaagagtt ggtggagaca    40980
catggtgcaa atcctgagca gtagctgaag gaaaggtaca agtttggcag tagattggcc    41040
aatgaggtgc agagataaag cagaagggct gccccgagag ctgcagcatg gtgcgtggaa    41100
cccttcagga ggtagaaagg tagaaagggc tgcttggact actagtgtgt agattactgt    41160 cttttcagcag gtgaaagaca aggctagagc ctgtgattgg acagtagaaa aggagggcgg    41220
gctgagagtt tgagagtctg gagggatagg aggaaagaag gaagatggag gaagagaagg    41280
atgacccaga gctgtgtggc tttaaatagc cacaggtagc tatgaatatc atataagggg    41340
tggattatga caggacaatt tgtccactca aggtgggcag cttatatcat attaattggc    41400
tctgagttct ttgtcttggg catttttgtga gctgagaatt tactgatata aatctgactg    41460
ataaattaca agcctctaga gttttgattt tactgggtta cagggatttg tgacagttaa    41520
ctgcgagatg ctacagccag agagacacgg attctgctaa gtagatgact cttgtacata    41580
tgtgtgtatg ggggctagct gtgaaggcag tgaaactgct gccagggcca gagagtagtt    41640
```

```
ggcactactg tgggatggtg catccatttt tttaaaaatt atttaatgca acactagtga  41700
gtcatccagt aggaaatgct ggggtctggg gagctggggg tggaggaaag ccacaagccc  41760
acggagcccc agatccccca cctctttgga gaataacact gatatcagtg actcagacac  41820
aatagatctt ggggttcagc acccaagctc ctctagtaag catgggtgca aaaggtgtgg  41880
aatggagagt gaaggaagac tttttcataa gcctgtcaca aatgaggagg aagctaagct  41940
tgggaaatgc aggccttcag tggcagacca agtggagtca atgaagtaag gtctgagtag  42000
aagggctctg ggtgtgcgct tcaggctggg tgcacacttc tttctgagga aatgctcact  42060
tccactttga ccattccctg acccaggtca tagctgatgt gccagagtgt catgggtgaa  42120
gtggtcactt tcgctctttc cacacaactg tgctgtgtaa gacacccttt ctctggtcat  42180
acaggagtcc cctgtggggt ttgagccctg acttaaaaag aaaggatgag ggctacttct  42240
gtggaaggga gcaaagagca gaggtcattc ctgctggagg agatctgcta acaagcatgt  42300
gatgtttaac attaagggct gctcatcaag tcagcactga ctccagcaga gtcctgtcga  42360
ggctactcca gtatgccctg gtcaagacta gccttggcaa gggagcagcc tgggctgttg  42420
ctaggtggat agaagcacac acagaggatt ttccttagtgg tgtatgtaat cactgaggtc  42480
ttgctgaccc agtaggcata ctcctccatt gctagactca gtcacacaaa gtgtacaaga  42540
acagggcatt cttcatggaa aattcctgac tgggtctttt agagctccag ttcctagagg  42600
ggcagatgat cccagtgact tatgctcagt gtaaagctgg tctgctgtca catctttgct  42660
cccaaaggtt tctgggattc ctcctgtact ttccttctatt tttattttca agacagggc  42720
tctctgtgta gtcctggctg ctctggaact tgctctgcag accaggttgg cctcaaattt  42780
atagagatcc acttgcctct gccgtccaag tacagggatt aaagttgcat gccaccactg  42840
cccagcctct ctaaaatttt cttaattaat ttattttca agacagagtc tcactatgta  42900
gtcctggata tgctggaact cagtaatgta gaacaggctg tccttgaaca tacagagttc  42960
caccaacctc tgcttccaag tgctgggatt gaagtgtgtg ccactatgcc cagctaaaac  43020
ctgtttatt ttctgtgcat gggtgtttgc ctgcatgtat gtctgtgcat catttgcctg  43080
actggtgccc acggaagtca gaggaggaca ctggatcccc tgaggtgccc acggaagtca  43140
gaggaggaca ccggatcccc tgcagtgccc atggaagtca gaggaggaca ccggatctcc  43200
tggatctgga tgactgagcc atcacatggg tcttgggaaa agatcccggg tttgctctaa  43260
gaacaagtgc tcttaatgat tgagatgtct ctctatccca tgtttctttg tacacaaaca  43320
ccatggacac gtggcataca ctgggcttcc ttttcacacc actctgtcga acttaaattc  43380
tgctggcggc tccaactgac ctttcctttc tattcctaaa ttctcggcat ggcttgggtc  43440
tggttaagtc ccccctttc caagcagccg gaagcactta tctctgaatg tgcctctgtg  43500
ggacacaccg ggggacctgc tgaagcctct gaagagcaga ggtgatgtct gcctccccat  43560
cttttgccctc ttgtgctaag aagctacttg tgatgctgga ggtggtgggg aaaacccacc  43620
agccttgcca cctgaagtga agggcagcca cggcctgtgt cctagccagt ggggattagt  43680
gaaaatggta aagtgggcaa cgaggctgct tgctttctga gcttcctcct attttgggtt  43740
ggtagcagca gcggcccagt tccttcccac tgtggggatg aggagtacgc cctcaggatg  43800
ccggcatcag agaaggcaag aacagacgca gtgtcgcacg tcttcaatta cagcacttgg  43860
gaggcagaga caggcagatc tctgcgagtt caaggccagt ctggtctaca cagtgagttc  43920
taggttcgtc tgtgttacac agggagaact gtctgaagaa acaaacaaag agaaaattaa  43980
agttagatgt agtggcacgg tcataatcta aaatgtggcc tagctgttct ctgttctctg  44040
```

-continued

```
tttctcttc ttcctccctc cctctctctt cttcattgtc tgtctgtctg gtgcttgtat    44100
atcaaaatgt aagttctaag atatgcttca gcaccgtgcc tgcctgcctg ccgccatgct    44160
ccaccatgat agtcatagac ccaccctctc gaactgtgaa tcccaaattt actttcttct    44220
atgagttgcc ctggttatgg tgccttatca cagcaacaga gcagtgagta atatacccac    44280
cctcaaagac aagctgaaag agagacccat gtgctgtggc atgcgtgtgc ctacacttaa    44340
cacacataaa taaatacatc tcctgaagaa aatttaaaag ttattctgga cagaaactag    44400
agaggccaga ctggcctcag ctcaagccca cagcagctcc tctgtcctgc tgtcctttcc    44460
tgtagagaaa ttcagtgaga cccaagctgt ctgtcctagg gctataagct gggtgggtgg    44520
ctgggatgac cacacttgat agaaaagagg aaaaggaact gggagttgcg gccgcc        44576
```

```
<210> SEQ ID NO 18
<211> LENGTH: 23
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 18
ggacagcccg aaggactaca ggt                                             23

<210> SEQ ID NO 19
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 19
cgaagaactc cgcagggtcc                                                 20

<210> SEQ ID NO 20
<211> LENGTH: 18
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(18)
<223> OTHER INFORMATION: SYNTHETIC PRIMER

<400> SEQUENCE: 20
aagacccgcc acgacccg                                                   18

<210> SEQ ID NO 21
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER
```

```
<400> SEQUENCE: 21
gaatcagcac cctctccgcc                                              20

<210> SEQ ID NO 22
<211> LENGTH: 25
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(25)
<223> OTHER INFORMATION: SYNTHETIC PRIMER

<400> SEQUENCE: 22
tgcggagttc ttcgtgctga tggag                                        25

<210> SEQ ID NO 23
<211> LENGTH: 20
<212> TYPE: DNA
<213> ORGANISM: Artificial
<220> FEATURE:
<223> OTHER INFORMATION: SYNTHETIC PRIMER
<220> FEATURE:
<221> NAME/KEY: misc_feature
<222> LOCATION: (1)..(20)
<223> OTHER INFORMATION: SYNTHETIC PRIMER

<400> SEQUENCE: 23
ggtgctcggc ggcgtccttc                                              20

<210> SEQ ID NO 24
<211> LENGTH: 21
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(21)
<223> OTHER INFORMATION: synthetic primer

<400> SEQUENCE: 24
gagtggcgga gagggtgctg a                                            21

<210> SEQ ID NO 25
<211> LENGTH: 18
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(18)
<223> OTHER INFORMATION: synthetic primer

<400> SEQUENCE: 25
ggccgaggct gagcgggg                                                18

<210> SEQ ID NO 26
<211> LENGTH: 20
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(20)
<223> OTHER INFORMATION: synthetic primer
```

```
<400> SEQUENCE: 26
ctgaaggacg ccgccagca                                                    20

<210> SEQ ID NO 27
<211> LENGTH: 19
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(19)
<223> OTHER INFORMATION: synthetic primer

<400> SEQUENCE: 27
ctccaacgcc tgccgctgc                                                    19

<210> SEQ ID NO 28
<211> LENGTH: 21
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(21)
<223> OTHER INFORMATION: synthetic primer

<400> SEQUENCE: 28
gcaggaggag cgggagcagg a                                                 21

<210> SEQ ID NO 29
<211> LENGTH: 19
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (1)..(19)
<223> OTHER INFORMATION: synthetic primer

<400> SEQUENCE: 29
tccagtgccc cgcaagccg                                                    19

<210> SEQ ID NO 30
<211> LENGTH: 41
<212> TYPE: PRT
<213> ORGANISM: Unknown
<220> FEATURE:
<223> OTHER INFORMATION: conserved sequence
<220> FEATURE:
<221> NAME/KEY: DOMAIN
<222> LOCATION: (1)..(41)
<223> OTHER INFORMATION: CONSERVED SEQUENCE

<400> SEQUENCE: 30

Met Leu Arg Ala Leu Asn Arg Leu Ala Ala Arg Pro Gly Gly Gln Pro
1               5                   10                  15

Pro Thr Leu Leu Leu Leu Pro Val Arg Gly Pro Arg Pro Arg Ser Phe
            20                  25                  30

Ser Ala Pro Phe Ser Ser Gln Asp Ser
            35                  40
```

```
<210> SEQ ID NO 31
<211> LENGTH: 123
<212> TYPE: DNA
<213> ORGANISM: Unknown
<220> FEATURE:
<223> OTHER INFORMATION: conserved sequence
<220> FEATURE:
<221> NAME/KEY: misc_feature
<222> LOCATION: (1)..(123)
<223> OTHER INFORMATION: conserved sequence

<400> SEQUENCE: 31
atgttgcggg ctttgaaccg cctggccgcg cggcccgggg gccagccccc aaccctgctc      60
cttctgcccg tgcgcggccc acggccccgc tcattctcgg ctccttttc ctcgcaggat     120 agc                                                                  123

<210> SEQ ID NO 32
<211> LENGTH: 19
<212> TYPE: DNA
<213> ORGANISM: Unknown
<220> FEATURE:
<223> OTHER INFORMATION: conserved sequence in mouse
<220> FEATURE:
<221> NAME/KEY: misc_feature
<222> LOCATION: (1)..(19)
<223> OTHER INFORMATION: conserved sequence in mouse

<400> SEQUENCE: 32
agacataaaa aggtcggtc                                                  19

<210> SEQ ID NO 33
<211> LENGTH: 19
<212> TYPE: DNA
<213> ORGANISM: Homo sapiens

<400> SEQUENCE: 33
aggcataaaa aggccaggc                                                  19

<210> SEQ ID NO 34
<211> LENGTH: 19
<212> TYPE: DNA
<213> ORGANISM: Unknown
<220> FEATURE:
<223> OTHER INFORMATION: conserved sequence in Bos
<220> FEATURE:
<221> NAME/KEY: misc_feature
<222> LOCATION: (1)..(19)
<223> OTHER INFORMATION: conserved sequence in Bos

<400> SEQUENCE: 34
cgggcttaaa aggccagac                                                  19

<210> SEQ ID NO 35
<211> LENGTH: 19
<212> TYPE: DNA
<213> ORGANISM: Rattus sp.

<400> SEQUENCE: 35
aggcataaaa aggtcggtc                                                  19

<210> SEQ ID NO 36
<211> LENGTH: 19
<212> TYPE: DNA
<213> ORGANISM: Artificial
<220> FEATURE:
<223> OTHER INFORMATION: construct
```

```
-continued

<220> FEATURE:
<221> NAME/KEY: misc_feature
<222> LOCATION: (1)..(19)
<223> OTHER INFORMATION: construct

<400> SEQUENCE: 36
aggcataaaa aagtcggtc                                              19

<210> SEQ ID NO 37
<211> LENGTH: 15
<212> TYPE: PRT
<213> ORGANISM: Unknown
<220> FEATURE:
<223> OTHER INFORMATION: conserved sequence
<220> FEATURE:
<221> NAME/KEY: DOMAIN
<222> LOCATION: (1)..(15)
<223> OTHER INFORMATION: conserved sequence

<400> SEQUENCE: 37

Pro Arg Pro Arg Ser Phe Ser Ala Pro Phe Ser Ser Gln Asp Ser
1               5                   10                  15
```

OBESITY GENE

CROSS-REFERENCE TO RELATED APPLICATION

This application claims priority under 35 U.S.C. §120 to International Application serial number PCT/GB99/02658, filed Aug. 12, 1999, which claims priority to application serial number GB9910522.3, filed May 6, 1999, and GB9817566.4, filed Aug. 12, 1998.

The present invention relates to a gene which is involved in the control of obesity and fertility. In particular, the gene disclosed herein is involved in late-onset obesity in males, which is coupled with infertility. Moreover, the invention relates to animal models for late-onset obesity.

Obesity, which differs from being overweight by being characterised by an increase in the proportion of body fat present as opposed to a mere increase in body weight, is one of the major contributors to chronic disease development. Mortality in overweight males (5–15% overweight) increases to 125%, but rises up to 500% in obese males. Laboratory and epidemiological studies have also shown that mortality amongst obese males aged between 25 and 34 can increase up to twelve times. This increase in mortality is caused by the multitude of health risks associated with obesity, including cardiovascular disease, hypertension, diabetes, sleep apnoea (the abnormal ceasing of breathing during sleep), hernias, flat feet, arthritis, osteoarthritis, some cancers, varicose veins, gout, respiratory problems, gall bladder disease and liver disease. The more serious complaints include:

Cardiovascular Disease—Obesity is an important factor in cardiovascular disease in both increasing blood cholesterol and blood pressure, and has been shown to increase the risk of disease by up to three times. Obesity also increases the work of the heart—cardiac volume, stoke volume and blood volume must all increase to cope with the increased weight. The detrimental effects of obesity on cardiovascular disease are reversible with weight loss.

Diabetes—Excess weight also increases the chance of acquiring diabetes mellitus by threefold and increases the risk of dying from diabetes by up to eight times. The mechanism by which an increase in body fat increases the risk of diabetes is largely unknown. However, it is postulated that a slight increase in circulating serum glucose or L-leucine may increase the basal levels of insulin. This rise in insulin is then associated with resistance to insulin, caused both by decreased intracellular effects of insulin and a reduction in insulin receptors in the cell. Obesity has also been proven to alter pancreatic function and in susceptible individuals this may lead to the development of diabetes mellitus.

Cancer—cancer has also shown a significant association with obesity, but the mechanisms are not understood. One proposed explanation is that obesity alters hormone levels and this could influence cancer development. In males, obesity is associated with a greater risk of developing prostate and colorectal cancers.

Gall bladder Disease—obese males show a four times increase in the risk of developing gall bladder disease.

Endocrine Function—this is also modified by elevated fat levels. The Beta cells in the islets of Langehans are enlarged in obese people and glucose intolerance is also frequently inhibited.

Reproductive System—obesity in males also impairs the functioning of the reproductive system.

Growth Hormone—obesity impairs the release of growth hormone from the pituitary gland. This problem is of particular importance in obese children whose growth may be impaired. It is fully reversible if weight is lost.

Numerous genes, gene products and their receptors have been characterised in rodent models of obesity which bear mutations associated with different forms of obesity (Bray & York, 1979; Comuzzie & Allison, 1998). Most such spontaneous mutations are recessive, and include mutations affecting leptin and its receptors in such models as ob/ob and db/db mice, Zucker fa/fa rats, Koletsky (f) rats, OLETF rats, corpulent (cp) rats and their substrains or derivatives (Zhang et al., 1994; Tartaglia et al., 1995; Iida et al., 1996; Takaya et al., 1996; Chen et al., 1996; Jamal et al. 1997; Kahle et al., 1997; Lee et al., 1997; Moon & Friedman, 1997; Takiguchi et al., 1998). These phenotypes are thought to result from a disruption in leptin or its receptors or in CCK-A receptors, and affect the control of food intake or energy expenditure or metabolism, and disrupt the gonadotrophic axis in females.

There are numerous other candidate genes putatively involved in obesity, some of which have been recently been summarised by Comuzzie & Allison (1998; Table 1). These include tubby (tub), agouti, Nh12, MCH, CRH, hypocretins or orexins, CART peptides, melanocortin-4 ligands, uncoupling proteins (UCP1–3), carboxypeptidase E, NPY, their related transcripts or homologues or their receptors (Coleman et al., 1990; Miller et al., 1993; Good et al., 1997; Klebig et al., 1995; Naggert et al., 1995; Ollman et al., 1995; Kleyn et al., 1996; Richard, 1996; Qu et al., 1996; Fan et al., 1997; Huszar et al., 1997; North et al., 1997; Ohki-Hamazaki et al., 1997; Graham et al., 1997; Boss et al., 1997; Vidal-Puig et al., 1997; Millet et al., 1997; Cool et al., 1997; Kristensen et al., 1998; De Lecea et al., 1998; Sakurai et al., 1998). These models exhibit some degree of sexual dimorphism, a slight delay in onset of obesity or a dominant pattern of inheritance, though none show all of these in combination. It is generally believed that obesity is due to the complex interaction of a number of different factors.

The study of obesity and its effects on health requires suitable animal models which can faithfully replicate the condition as seen in humans. None of the available models combines all of the symptoms of obesity. In particular, the symptoms of male pattern obesity, which include late onset, sterility and a concentration of fat around the abdomen, are not displayed by currently available models. There is therefore a need for an improved model for obesity, which displays more of the characteristics of obesity observed in human patients.

Transgenesis is a well established technique for the introduction of DNA sequences into the mammalian genome, and has been used to insert endocrine genes in several species, predominantly in mice (Palmiter et al., 1982; Bucchini et al., 1986; McGrane et al., 1988; Ho et al., 1995), but also in other species (Hammer et al., 1985; Pursel et al., 1989), including rats (Mullins et al., 1990, Zeng et al., 1994, Chareau et al., 1996; Flavell et al., 1996). The methods are well described (Hogan et al., 1986, Chareau et al., 1996) and usually involve the microinjection of cloned DNA fragments into the male pro-nuclei of eggs isolated from superovulated females. Such eggs are transferred into the oviduct of pseudopregnant females (obtained by mating with vasectomized males) and carried to term. DNA extracted from tail clippings obtained from the progeny may be examined for the presence of specific transgene DNA. Depending on the integrity and stability of the DNA sequence, the number of integration sites and their location in the host genome, transgenes may become stably integrated in the host genome and transmitted to subsequent progeny.

If promoter and enhancer sequences are present in the transgene, the transgene may show high levels of expression in the host animals and the products may induce an endocrine phenotype that would be expected from the hormone product. For example, overexpression of human growth hormone (hGH) using a variety of heterologous non-specific promoters induces variable degrees of growth stimulation in transgenic animals (Palmiter et al., 1982, 1983; Morello et al., 1986; Pursel et al., 1989; Shanahan et al., 1989; Stewart et al., 1992; Short et al., 1992). However, transgene expression levels often differ between different transgenic lines made with the same insert, and the tissue specificity may vary, being highly dependent on the size of the DNA insert, the number of copies of the insert, its integrity and its integration site(s) in host DNA (Lacy et al., 1983; Al-Shawi et al., 1990; Huber et al., 1994). Unexpected phenotypes may result, either as pathological consequences of inappropriate amounts of transgene product or its production in ectopic sites, and examples of this for hGH transgenes include glomerulosclerosis or female infertility in mice or rats (Bartke et al., 1988; Brem et al., 1989; Quaife et al., 1989; Ninomiya et al., 1994). Intentionally directed expression of a transgene to an ectopic site may also have a significant influence on the nature of the phenotype produced (Omitz et al., 1985; Baker et al., 1992). This is well exemplified using hGH transgenes, since instead of an overgrowth phenotype, hGH can produce an opposite, dwarf phenotype in transgenic mice or rats when driven by a promoter that targets it to the central nervous system to induce negative feedback effects on the endogenous GH system (Hollingshead et al., 1989, Banerjee et al., 1994; Szabo et al., 1995, Flavell et al., 1996).

Other examples of endocrine transgenes include those targeting the genes for oxytocin (OT) and vasopressin (AVP) (Russo et al., 1988; Habener et al., 1989; Grant et al., 1993a,b; Ang et al., 1991, 1994; Murphy & Ho, 1995). These genes are expressed mainly in magnocellular neurones of the supraoptic (SON) and paraventricular (PVN) nuclei of the hypothalamus (Vandesande et al., 1975; Young, 1992; Gainer & Wray, 1994). The expression of these hormonal peptides appears to be mutually exclusive, coexpression in the same neurone occurring only rarely (Kiyama et al., 1990). A construct consisting of sequences 0.6 kb 5', 1.8 kb 3' and the entire structural gene of bovine OT directed expression to the oxytocinergic cells of the SON and the PVN, but also to the lung and Sertoli cells of the testis in transgenic mice (Ho et al., 1995). The hypothalamic expression was also physiologically regulated with an increase in the abundance of the transgene transcript occurring during dehydration. The Sertoli cells are a site of peripheral expression of the endogenous OT gene in cattle but not in mice or rats. In these transgenic mice, the testicular transcripts are translated and processed (Ang et al., 1994), suggesting that this construct contained regulatory elements capable of recapitulate the bovine expression pattern of OT in the mouse testis (Ang et al. 1991). Foo et al. (1994) have identified a testis-specific promoter in the rat AVP gene.

The AVP and OT genes are highly homologous in structure, and are transcribed in opposite orientations from positions closely linked in the genome within a single locus (Sausville et al., 1985; Young, 1992). It is therefore possible that elements in the flanking sequence of the OT gene normally interact with those present in the nearby homologous AVP gene to regulate their mutually exclusive expression (Young et al., 1990; Young, 1992). To test this theory, mice were generated bearing 1.25 kb of 5', 0.2 kb of 3' and the structural gene for bovine AVP fused, in same the same orientation as the endogenous genes, to the bovine OT transgene already described to show hypothalamic expression (Ho et al., 1995). The resulting mice expressed the bovine OT transgene in the testis and lung, but lacked hypothalamic expression of this transgene and did not express the bovine AVP transgene. A further bovine OT transgene, including 3 kb of 5' sequence, the structural gene and 2.5 kb of downstream sequence was used in an attempt to overcome this repression, but no animals were generated, and it was argued that the region between 0.6 kb and 3 kb 5' of the bovine OT gene conferred a toxic effect in embryonic development which is usually repressed (Ho et al., 1995). Transgenic rats have also been generated bearing fragments of the rat AVP gene with reporter genes inserted into the third exon of the AVP gene. Transgenes containing 1.5 kb and 3 kb of 5', 0.2 kb of 3' and the rat AVP gene with a β-galactosidase reporter gene in the third exon also conferred expression to the testis. This was attributed to the presence of a cryptic testicular promoter within the reporter gene (Zeng et al., 1994a). Clearly however, the use of small fragments of DNA containing OT or AVP sequences gives rise to unpredictable patterns of transgene expression.

One theory is that this variation may be overcome if sufficiently large DNA constructs are used, containing regions of DNA known as locus control regions (LCRs) that can direct tissue specific, position independent, copy number dependent, physiologically appropriate, expression of the transgene in the host (Grosveld et al., 1987; Bonifer et al., 1990; Huber et al., 1994; Fujiwara et al., 1997). Again this may be exemplified with hGH transgenes. An LCR region for the hGH gene has been defined by Jones et al. (1995). When a cosmid containing this sequence was used to generate several lines of transgenic mice, hGH was expressed in the pituitary gland in an appropriately regulated fashion, and the mice showed no overgrowth phenotype or other pathological consequences of overproduction of hGH.

SUMMARY OF THE INVENTION

A line of transgenic rats has been generated using a cosmid of rat DNA containing the genes for oxytocin (OT) and vasopressin (AVP), into which reporter genes were inserted, namely hGH (Roskam et al., 1979) in the AVP gene and bovine OT mostly replacing the rat OT gene. To attempt to include LCR regions for this gene locus in our transgene constructs, larger DNA fragments containing both OT and AVP genes and larger amounts of flanking sequences were used, which were isolated from a rat cosmid library. One line of such rats, bearing at least 4 copies of this cosmid as a concatamer integrant, exhibits an unexpected and novel late onset obesity and infertility dominant phenotype that would not be predicted from the known DNA sequences present in this cosmid. This phenotype is clearly distinguishable from other obesity/infertility syndromes so far described.

Analysis of the cosmid sequences used in the transgene constructs reveals the presence of a previously unknown gene, which is responsible for the observed obesity phenotype.

Accordingly, in the first aspect of the present invention there is provided a 5'OT-EST polypeptide having a sequence selected from the group comprising the sequences set forth in any one of SEQ. ID. Nos. 2, 4 or 6, and sequences substantially homologous to any one of the polypeptides set forth in SEQ. ID. Nos. 2, 4 or 6.

In a second aspect, the invention provides a mutant of a 5'OT-EST polypeptide according to the first aspect of the invention which is capable, in vivo, of modulating the obesity of an animal expressing it.

In a third aspect, the present invention provides a nucleic acid encoding a 5'OT-EST polypeptide or mutant 5'OT-EST polypeptide according to the first aspect of the invention. Advantageously, the nucleic acid has a sequence selected from the group consisting of any one of SEQ. ID. Nos. 1, 3, 5 or 7; sequences which are hybridisable under stringent conditions with an oligonucleotide comprising 20 contiguous bases from any one of SEQ. ID. Nos. 1, 3, 5 or 7; sequences substantially homologous to any one of SEQ. ID. Nos. 1, 3, 5 or 7; and sequences complementary thereto. Stringent hybridisation conditions are preferably as defined below.

In a fourth aspect, the invention provides diagnostic reagents for the detection of mutations, polymorphisms or other changes in 5'OT-EST which may predispose an individual to obesity. For example, the invention provides probes useful for amplifying 5'OT-EST nucleic acids.

In a fifth aspect, the invention provides a transgenic non-human animal expressing, as a result of transgene expression, a 5'OT-EST polypeptide or mutant 5'OT-EST polypeptide according to the invention. Transgenic animals according to this aspect of the invention are models for obesity in humans, and may be used for research into therapies and treatments which may be used to alleviate obesity.

BRIEF DESCRIPTION OF THE DRAWINGS

FIG. 6 is an alignment of the sequences of 5'OT-EST from rat, human, and mouse sources. The mouse amino acid sequence is SEQ ID NO: 6, the rat amino acid sequence is SEQ ID NO: 2 and the human amino acid sequence is SEQ ID NO: 4. The predicted deleted form in JP17 is SEQ ID NO: 8.

FIG. 12 shows the levels of plasma insulin, glucose, cholesterol, triglycerides, leptin and corticosterone in terminal blood samples from transgenic and non-transgenic rats. Values shown are mean of each group +/−SEM (n=6 for transgenic groups; n=4 for non-transgenic groups) (* Significantly different (p<0.05) from sex matched non transgenic group).

DETAILED DESCRIPTION OF THE INVENTION

Definitions

Figure 1:
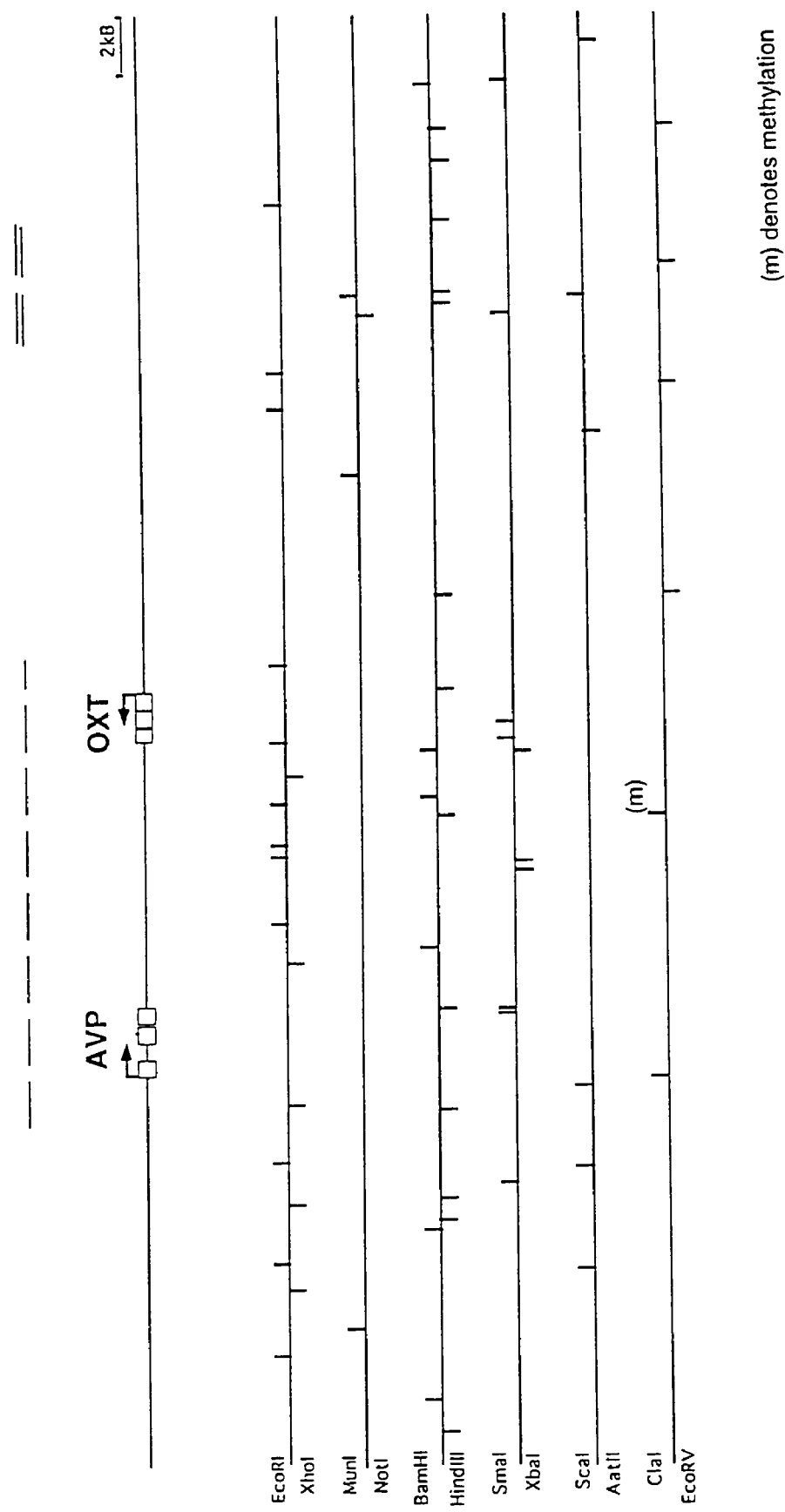
FIG. 1 shows a partial restriction map of the rat AVP/OT locus, from cosmid cVO1, cVO2 and cVO3. Restriction sites for the enzymes listed are shown as a vertical marks. The known sequence of the rat AVP and OT genes is indicated by single dashed lines, and the sequence determined and disclosed herein of the rat 5'OT-EST gene is indicated by the double dashed line. Scale is approximate.

As referred to herein, "5'OT-EST" is the polypeptide represented in SEQ. ID. Nos. 2, 4 or 6 (rat, human and mouse respectively). Preferably, it is the human sequence. However, the term also covers alternative peptides homologous to 5'OT-EST, such as polypeptides derived from other species, including other mammalian species.

"Mutants" of 5'OT-EST include polypeptides which differ only in minor, insignificant ways from wild-type 5'OT-EST, for example polypeptides having conservative amino acid replacements or additions or deletions. Preferred, however, are mutants which are able to confer, on animals expressing them, an obese phenotype as defined herein. An example of such a mutant is the 5'OT-EST-xdel polypeptide set forth in SEQ. ID. No. 8. Further mutants may be obtained as described herein, and defined according to their functional effects in transgenic animals or host cells.

"Substantially homologous", whether applied to polypeptide or nucleotide sequences, is as defined herein with reference to homology screening. It may be interpreted as referring either to sequence aligment and direct comparison, or to homology as defined by BLAST homology searching as defined herein.

A "transgenic animal" is an animal whose genome has been functionally altered by genetic manipulation. In the context of the present invention, this includes animals bearing and expressing a 5'OT-EST or mutant 5'OT-EST transgene, animals from which 5'OT-EST sequences have been deleted or in which they have been modified, and animals which are transiently transformed to express a (mutant) 5'OT-EST transgene such as by transformation with viral sequences.

"Transformation" refers to the functional insertion of a gene by nucleic acid transfer, or the functional deletion of a gene, in a cell or organism. The term thus includes transfection, transduction and any other techniques useful for transferring nucleic acids into cells or organisms. Cells transformed according to the invention express a novel genotype as a result of the transformation.

For the avoidance of doubt, unless otherwise required by the specific context, reference herein to an entity in the singular includes the plural thereof. Thus, the expressions "a gene" and "one or more genes" are equivalent.

Moreover, unless otherwise required by context, references to 5'OT-EST (5'OT-EST) preferably include mutants of 5'OT-EST (5'OT-EST).

A "cosmid" is a bacteriophage-based vector as commonly known in the art.

References herein to "obesity" and obese animals are preferably references to the SLOB phenotype observed in SLOB rats according to the invention, characterised in being inter alia male-specific, late onset, with fat deposition concentrated in the abdominal area and associated with sterility.

DESCRIPTION OF PREFERRED EMBODIMENTS

A cosmid (cVO14) of rat DNA containing the rat vasopressin (AVP) and rat oxytocin (OT) genes (Ivell & Richter, 1984) was constructed, and DNA reporter sequences inserted therein using standard methods (Sambrook et al., 1989) as outlined in Examples 1 & 2 below. Microinjection of the cVO14 DNA insert into fertilised rat eggs and their transfer into pseudopregnant recipients resulted in production of viable offspring. Unexpectedly, the male founder rat with 4–5 copies of cVO14 (JP17) showed a dominant phenotype of severe late-onset visceral obesity. This form of obesity shows (i) a very late onset, (ii) a highly selective visceral distribution of fat developing on a normal rodent diet, without hyperphagia, (iii) an effect greatly preponderant in males, (iv) a predisposition to excessive dietary-fat induced obesity at an early age, before the phenotype becomes apparent on a normal diet, and (v) a dominant pattern of inheritance. Moreover, male transgenics show severe infertility in males, whilst females are fertile. Rats bearing this transgene have been termed SLOB rats (for Severe Late-onset OBesity). The symptoms of obesity observed in SLOB rats all occur in several forms of human obesity, including that associated with human syndrome-X (Reaven et al., 1988) for which a late-onset increase in abdominally distributed fat, affecting males much more severely than females (Gray et al. 1997) may be mimicked in the SLOB rat. Obvious causes, such as leptin deficiency or insulin resistance or overt Type 1 or 2 diabetes may be excluded.

Although the SLOB phenotype is preponderant in males, it may be markedly exacerbated in females by ovariectomy.

Mapping and analysis of cosmid DNA used to generate cVO14, revealed a putative gene, 5' of the OT locus. A fragment of this DNA was subcloned and sequenced. Analysis of this region of rat DNA enabled us to determine the location, orientation, partial exon structure and predicted protein product of a novel gene lying 5' of the OT gene in rat DNA. Further sequencing and analysis elucidated the structure of this gene, and provided additional sequence information for the cosmid DNA surrounding the known sequence of the OT and AVP genes. The novel rat gene is termed herein 5'OT-EST, which encodes the 5'OT-EST polypeptide. The genomic sequence of 5'OT-EST is given in SEQ. ID. No. 16.

A search of DNA and protein databases revealed no significant match to any known gene, but recognised partial matches to DNA sequences homologous to 5'OT-EST in expressed sequence tag (EST) databases from rat, mouse and human DNA sources. These represent partial products of the rat gene, and of genes homologous to this novel rat gene, in mouse and human DNA. The predicted structures of four exons, termed w, x, y, z, and predicted protein sequences are highly conserved between these species. A partial match was noted to a human genomic DNA sequence alluded to, but not disclosed in White et al. PNAS 95:305–309 (1998), but deposited by them in Genbank (Accession no:AF036329) as a putative genomic fragment containing the human GnRH-II gene. The relationship between human 5'OT-EST and human GnRH-II as described by White et al. is confirmed by the present work; however, there does not appear to be any such relationship in rats or mice. Homologous rat GnRH-II sequences cannot be recognised by sequence analysis in cVO14, which contains more than 10 kb of rat DNA flanking 5'OT-EST. Neither can any homologous mouse GnRH-II sequence be identified by hybridisation or PCR studies in multiple mouse genomic clones which contain 5'OT-EST and at least 50 kb of flanking DNA. Thus, it appears highly unlikely that the GnRH-II sequence corresponds functionally with 5'OT-EST.

In rats, 5'OT-EST lies about 10 kb downstream of the 3' exon of the protein tyrosine phosphatase receptor alpha (Ptpra) gene, and the intervening 10 kb show no homology with GnRH-II. Additionally, mouse BAC clones containing 5'OT-EST show no homology to GnRH-II. Thus, GnRH-II sequences are not adjacent to 5'OT-EST in rats or mice, and neither GnRH-II nor Ptpra is present in the cosmid used to generate SLOB rats. Complete sequencing of the cosmid reveals no other novel genes.

Based on physical linkage to Ptpra, Avp and Oxt, 5'OT-EST maps to the distal region of mouse chromosome 2, 7.32 cM from the centromere. Ptpra has itself been implicated in the control of insulin sensitivity, and both 5'OT-EST and Ptpra lie within 0.21 cM of mg, another gene implicated in the suppression of obesity. In mouse, all three genes map to the same region as the mouse obesity locus Mob5 (Encyclopaedia of the Mouse genome VII: Mouse Chromosome 2; (1998) Peters et al., Mamm. genome 8 Spec No:S27–49). It is likely therefore that 5'OT-EST contributes to the trait observed at this locus in mice.

Accordingly, the present invention provides 5'OT-EST polypeptide. 5'OT-EST according to the present invention may be mouse, rat or human 5'OT-EST, as well as variants of 5'OT-EST derivable from other species or by natural or artificial mutation of a 5'OT-EST gene.

The variant provided by the present invention includes splice variants encoded by mRNA generated by alternative splicing of a primary transcript, amino acid mutants, glycosylation variants and other covalent derivatives of 5'OT-EST which retain the physiological and/or physical properties thereof. Exemplary derivatives include molecules wherein 5'OT-EST is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of 5'OT-EST found within a particular species, preferably a mammal. Such a variant may be encoded by a related gene of the same gene family, by an allelic variant of a particular gene, or represent an alternative splicing variant of 5'OT-EST.

Variants which retain common structural features can be fragments of 5'OT-EST. Fragments of 5'OT-EST comprise smaller polypeptides derived from therefrom. Preferably, smaller polypeptides derived from 5'OT-EST according to the invention define a single feature which is characteristic of 5'OT-EST as described in the present application.

Derivatives of 5'OT-EST also comprise mutants thereof, which may contain amino acid deletions, additions or substitutions. Thus, conservative amino acid substitutions may be made substantially without altering the nature of 5'OT-EST. Deletions and substitutions may moreover be made to the fragments of 5'OT-EST comprised by the invention.

Mutants of 5'OT-EST according to the present invention may possess properties different from those of naturally occurring 5'OT-EST. In particular, 5'OT-EST mutants may modulate the expression of native 5'OT-EST.

5'OT-EST mutants may be produced from a nucleic acid encoding 5'OT-EST which has been subjected to in vitro mutagenesis resulting e.g. in an addition, exchange and/or deletion of one or more amino acids. For example, substitutional, deletional or insertional variants of 5'OT-EST can be prepared by recombinant methods and screened for immuno-crossreactivity with the native forms of 5'OT-EST.

Preferably, 5'OT-EST according to the present invention has the sequence of SEQ. ID. No.2 (rat), SEQ. ID. No. 4 (human) or SEQ. ID. No. 6 (mouse). Mutants possessing desired properties may be generated from these sequences, or isolated from natural sources, by a variety of techniques which assess the biological function of the 5'OT-EST mutant. For example, nucleic acids encoding 5'OT-EST mutants may be used to generate transgenic animals and these animals assessed for indications of an obesity phenotype.

For example, the effects of mutant transgenes may be assessed by carcass analysis, measurement of growth, body weight, body fat distribution, as well as other measures of analytes in body fluids or tissues relevant to obesity in transgenic animals (Mathe, 1995; Shillabeer, 1992). These include, but are not limited to, cholesterol, triglycerides, fatty acids, lipoproteins, and other dietary constituents or metabolites, as well as metabolic hormones, such as leptin, insulin, glucagon, catecholamines or glucocorticoids. Other relevant parameters include cardiovascular measures (Reaven, 1988, Gray & Yudkin, 1997). These may include measures of systolic or diastolic blood pressure, cardiac output, or vascular resistance, together with morphological changes to organ systems known to be affected by cardiovascular or obesity disorders, such as heart, major or minor blood vessels, their muscle or endothelial layers, and their elasticity or fragility. See for example McNamee et al. (1994).

Similarly, parameters related to the infertility phenotype that may be measured, include, but are not limited to, testicular weight, volume, development, spermatogenesis, sperm number, motility or ability to fertilise oocytes. They may also include measures of testicular fluid production and constituents, as well as products of other accessory organs including seminal vesicles or prostate, as well as hormones, receptors, and proteins important in male sexual function, such as testosterone, LH, FSH, inhibin or activin. Other responses that may be affected include energy expenditure, physical activity, ingestive behaviour, excretory behaviour, or reproductive behaviour, or the organs, hormones or receptors commonly recognised to be associated with these physiological systems, their metabolism or morphological structure.

5'OT-EST as disclosed herein is a polypeptide composed of four exons, termed w, x, y and z (see SEQ. ID. No. 16). Advantageously, mutants of 5'OT-EST are mutated in, or preferably lack all or part of, the sequences encoded by one or more exons of 5'-OT-EST. Preferably, mutants of 5'OT-EST lack, or are mutated in, all or part of the sequences encoded by exons x, y and z of 5'-OT-EST.

Preferably, the sequences encoded by exons x, y and z are deleted and those encoded by exon w partially deleted. Most preferably, the mutant is 5'OT-EST-xdel as described herein, for example in SEQ. ID. No. 8.

The fragments, mutants and other derivatives of 5'OT-EST preferably retain substantial homology with 5'OT-EST. As used herein, "homology" means that the two entities share sufficient characteristics for the skilled person to determine that they are similar in origin and function. Preferably, homology is used to refer to sequence identity. Thus, the derivatives of 5'OT-EST preferably retain substantial sequence identity with 5'OT-EST.

"Substantial homology", where homology indicates sequence identity, means more than 40% sequence identity, preferably more than 45% sequence identity and most preferably a sequence identity of 50%, 60%, 70%, 75%, 80%, 85%, 90%, 95%, or 98 and 99%, as judged by direct best-fit sequence alignment and comparison.

Sequence homology (or identity) may moreover be determined using any suitable homology algorithm, using for example default parameters. Advantageously, the BLAST algorithm is employed, with parameters set to default values. The BLAST algorithm is known to those of skill in the art and is described, for example, in Altschul et al., 1990 (*J. Mol. Biol.* 215: 403).

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see Altschul et al., 1990 *J Mol. Biol.* 215: 403) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available on the World Wide Web at ncbi.nlm.nih.gov perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Clayerie & States (1993) Computers and Chemistry 17:191–201, or, for BLASTN, by the DUST program of Tatusov and Lipman (unpublished, but available on the World Wide Web at ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

More preferably, sequence comparisons are conducted using the simple BLAST search algorithm (Altschul et al., 1990 *J. Mol. Biol.* 215: 403).

Conventional BLAST serches of the publically available databases do not reveal any homology of the predicted protein product of 5'OT-EST to any known protein. However, application of a more sophisitcated search algorithm, as described in Taylor et al., 1998, identifies structural similarities to apolipoprotein E (ApoE) in its alpha-helical domains, but without any apparent LDL-receptor domain. Since ApoE is centrally involved in lipid metabolism and transport, a role for 5'OT-EST in cellular lipid handling is suggested.

Accordingly, the invention provides a method for identifying a candidate compound capable of influencing lipid transport, comprising the steps of:

a) contacting 5'OT-EST polypeptide with a candidate compound or compounds and determining which candidate compound or compounds is capable of interacting with 5'OT-EST;

b) optionally, testing candidate compounds which interact with 5'OT-EST in a transgenic animal according to the invention.

According to a further aspect of the present invention, there is provided a nucleic acid encoding 5'OT-EST or a mutant thereof. In addition to being useful for the production of recombinant 5'OT-EST protein, these nucleic acids are also useful as probes, thus readily enabling those skilled in the art to identify and/or isolate nucleic acid encoding 5'OT-EST and/or mutant 5'OT-EST. The nucleic acid may be unlabelled or labelled with a detectable moiety. Furthermore, nucleic acid according to the invention is useful e.g. in a method determining the presence of 5'OT-EST-specific nucleic acid, said method comprising hybridising the DNA (or RNA) encoding 5'OT-EST (or its complement) to test sample nucleic acid and determining the presence of 5'OT-EST. In another aspect, the invention provides a nucleic acid sequence that is complementary to, or hybridises under stringent conditions to, a nucleic acid sequence encoding 5'OT-EST.

The invention also provides a method for amplifying a nucleic acid test sample comprising priming a nucleic acid polymerase (chain) reaction with nucleic acid corresponding to 5'OT-EST, including the untranslated regions (or its complement).

In still another aspect of the invention, the nucleic acid is DNA and further comprises a replicable vector comprising the nucleic acid encoding 5'OT-EST operably linked to control sequences recognised by a host transformed by the vector. Furthermore the invention provides host cells transformed with such a vector and a method of using a nucleic acid encoding 5'OT-EST to effect the production of 5'OT-EST, comprising expressing 5'OT-EST nucleic acid in a culture of the transformed host cells and, if desired, recovering 5'OT-EST from the host cell culture.

Isolated 5'OT-EST nucleic acid includes nucleic acid that is free from at least one contaminant nucleic acid with which it is ordinarily associated in the natural source of 5'OT-EST nucleic acid or in crude nucleic acid preparations, such as DNA libraries and the like. Isolated nucleic acid thus is present in other than in the form or setting in which it is found in nature. However, isolated 5'OT-EST encoding nucleic acid includes 5'OT-EST nucleic acid in ordinarily 5'OT-EST-expressing cells where the nucleic acid is in a chromosomal location different from that of natural cells or is otherwise flanked by a different DNA sequence than that found in nature.

In accordance with the present invention, there are provided isolated nucleic acids, e.g. DNAs or RNAs, encoding 5'OT-EST, particularly mammalian 5'OT-EST, e.g. human 5'OT-EST, or fragments thereof. In particular, the invention provides a DNA molecule encoding 5'OT-EST, or a fragment thereof. By definition, such a DNA comprises a coding single stranded DNA, a double stranded DNA of said coding DNA and complementary DNA thereto, or this complementary (single stranded) DNA itself. An exemplary nucleic acid encoding 5'OT-EST is represented in SEQ ID Nos. 1, 3 and/or 5.

The preferred sequence encoding 5'OT-EST is that having substantially the same nucleotide sequence as the coding sequences in SEQ ID Nos. 1, 3 and/or 5, with the nucleic acid having the same sequence as the coding sequence in SEQ ID Nos. 1, 3 and/or 5 being most preferred. As used herein, nucleotide sequences which are substantially the same share at least about 90% identity. However, in the case of splice variants having e.g. an additional exon sequence homology may be lower. Homology is determined as described above.

The invention moreover provides nucleic acids encoding 5'OT-EST, comprising the gene 5'OT-EST or variants thereof as defined herein. The nucleic acids of the invention, whether used as probes or otherwise, are preferably substantially homologous to the sequence of 5'OT-EST as shown in SEQ ID Nos. 1, 3 and/or 5. The terms "substantially" and "homologous" are used as hereinbefore defined with reference to the 5'OT-EST polypeptide.

Preferably, nucleic acids according to the invention are fragments of the 5'OT-EST-sequence, or derivatives thereof as hereinbefore defined in relation to polypeptides. Fragments of the nucleic acid sequence of a few nucleotides in length, preferably 5 to 150 nucleotides in length, are especially useful as probes.

Exemplary nucleic acids can alternatively be characterised as those nucleotide sequences which encode a 5'OT-EST protein, or which correspond to untranslated regions of 5'OT-EST, and hybridise to the DNA sequences set forth SEQ ID Nos. 2, 4 and/or 6, or a selected fragment of said DNA sequence. Preferred are such sequences encoding 5'OT-EST which hybridise under high-stringency conditions to the sequence of SEQ ID Nos. 1, 3 and/or 5.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68° C. High stringency conditions can be provided, for example, by hybridisation in an aqueous solution containing 6× SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1× SSC, 0.1% SDS.

Moderate stringency refers to conditions equivalent to hybridisation in the above described solution but at about 60–62° C. In that case the final wash is performed at the hybridisation temperature in 1× SSC, 0.1% SDS.

Low stringency refers to conditions equivalent to hybridisation in the above described solution at about 50–52° C. In that case, the final wash is performed at the hybridisation temperature in 2× SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Advantageously, the invention moreover provides nucleic acid sequence which are capable of hybridising, under stringent conditions, to a fragment of SEQ. ID. Nos. 1, 3, 5 or 7. Preferably, the fragment is between 15 and 50 bases in length. Advantageously, it is about 25 bases in length, preferably about 20 bases in length. For differentiating between mutant and wild type 5'OT-EST by PCR reactions, 20mers are the preferred size, whilst for use as probes in, for example, Southern hybridisation, the use of 40mers is preferred. Riboprobes may be designed to be substantially any length, up to and including the entire length of the largest specific cDNA sequence.

Specifically included, moreover, are sequences complementary to the foregoing sequences.

Given the guidance provided herein, the nucleic acids of the invention are obtainable according to methods well known in the art. For example, a DNA of the invention is obtainable by chemical synthesis, using polymerase chain reaction (PCR) or by screening a, genomic library or a suitable cDNA library prepared from a source believed to possess 5'OT-EST and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding 5'OT-EST is to use PCR technology as described e.g. in section 14 of Sambrook et al., 1989. This method requires the use of oligonucleotide probes that will hybridise to 5'OT-EST nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to 5'OT-EST; oligonucleotides of about 20 to 80 bases in length that encode known or suspected 5'OT-EST cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding 5'OT-EST may be isolated by screening suitable cDNA or genomic libraries under suitable hybridisation conditions with a probe, i.e. a nucleic acid disclosed herein including oligonucleotides derivable from the sequences set forth in SEQ ID Nos. 1, 3 and/or 5. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases set forth in SEQ ID Nos. 1, 3 and/or 5. The nucleic acid sequences selected as probes should be of sufficient length and sufficiently unambiguous so that false positive results are minimised. The nucleotide sequences are usually based on conserved or highly homologous nucleotide sequences or regions of 5'OT-EST. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating $\alpha$-$^{32}$P dATP with the Klenow fragment of DNA polymerase in a random priming reaction, as is well known in the art. Oligonucleotides are usually end-labelled with $\gamma$-$^{32}$P-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

Probes for cloning and amplifying 5'OT-EST, especially human 5'OT-EST, may be deduced from the sequence thereof provided herein. Preferred probes may be selected from the following:

| 1U | GGACAGCCCGAAGGACTACAGGT | SEQ. ID. No. 18 |
|----|--------------------------|-----------------|
| 1L | CGAAGAACTCCGCAGGGTCC | SEQ. ID. No. 19 |
| 2U | AAGACCCGCCACGACCCG | SEQ. ID. No. 20 |

-continued

| 2L | GAATCAGCACCCTCTCCGCC | SEQ. ID. No. 21 |
|----|----------------------|-----------------|
| 3U | TGCGGAGTTCTTCGTGCTGATGGAG | SEQ. ID. No. 22 |
| 3L | GGTGCTCGGCGGCGTCCTTC | SEQ. ID. No. 23 |
| 4U | GAGTGGCGGAGAGGGTGCTGA | SEQ. ID. No. 24 |
| 4L | GGCCGAGGCTGAGCGGGG | SEQ. ID. No. 25 |
| 5U | CTGAAGGACGCCGCCGAGCA | SEQ. ID. No. 26 |
| 5L | CTCCAACGCCTGCCGCTGC | SEQ. ID. No. 27 |
| 6U | GCAGGAGGAGCGGGAGCAGGA | SEQ. ID. No. 28 |
| 6L | TCCAGTGCCCCGCAAGCCG | SEQ. ID. No. 29 |

Probes according to the invention are suitable for use as diagnostic reagents to amplify 5'OT-EST and thereby enable the analysis of the nucleic acid for the presence of mutations, polymorphisms or other changes which could render an individual susceptible to obesity.

After screening the library, e.g. with a portion of DNA including substantially the entire 5'OT-EST-encoding sequence or a suitable oligonucleotide based on a portion of said DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete 5'OT-EST (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous 5'OT-EST, genetic screening may be carried out using the nucleotide sequences of the invention as hybridisation probes or as PCR primers, using which genomic nucleic acid may be amplified, and subsequently sequenced. Also, based on the nucleic acid sequences provided herein antisense-type therapeutic agents may be designed.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce a 5'OT-EST mutant that has an amino acid sequence differing from the 5'OT-EST sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

The invention accordingly specifically includes nucleic acids encoding mutants of 5'OT-EST, as defined above. Such nucleic acids may be used for all the purposes identified above in relation to wild-type 5'OT-EST nucleic acids. Particularly preferred are nucleic acids encoding 5'OT-EST-xdel, which preferably have the sequence ATGTTG-CGGGCTTTGAACCGCCTGGCCGCGCGGCCCGGGG-GCCAGCCCCCAACCCTGCTCCTTCTGCCCGTGCGC- GGCCCACGGCCCCGCTCATTCTCGGCTCCTTTTCC-TCGCAGGATACG (SEQ ID NO: 31 see SEQ ID NO: 7), or an equivalent sequence which encodes the same polypeptide having regard to the degeneracy of the nucleic acid code, or a sequence substantially homologous thereto or complementary thereto. In 5'OT-EST-xdel exon x is deleted, and exons y and z are out of frame and therefore not translated.

For hybridisation probes, it may be desirable to use nucleic acid analogues, in order to improve the stability and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulphur; phosphoroamidites; alkyl phosphotriesters and boranophosphates. Achiral phosphate derivatives include 3'-O'-5'-S-phosphorothioate, 3'-S-5'-O-phosphorothioate, 3'-CH2–5'-O-phosphonate and 3'-NH-5'-O-phosphoroamidate. Peptide nucleic acids replace the entire phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The DNA sequences, particularly nucleic acid analogues as described above, may be used as antisense sequences.

In accordance with another embodiment of the present invention, there are provided cells containing the above-described nucleic acids. Such host cells such as prokaryote, yeast and higher eukaryote cells may be used for replicating DNA and producing 5'OT-EST. Suitable prokaryotes include eubacteria, such as Gram-negative or Gram-positive organisms, such as *E. coli*, e.g. *E. coli* K-12 strains, DH5α and HB101, or *Bacilli*. Further hosts suitable for 5'OT-EST encoding vectors include eukaryotic microbes such as filamentous fungi or yeast, e.g. *Saccharomyces cerevisiae*. Higher eukaryotic cells include insect and vertebrate cells, particularly mammalian cells, including human cells, or nucleated cells from other multicellular organisms. The propagation of vertebrate cells in culture (tissue culture) is a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of 5'OT-EST-encoding nucleic acid to form 5'OT-EST. The precise amounts of DNA encoding 5'OT-EST may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or By electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby 5'OT-EST encoded by the DNA is expressed. The composition of suitable media is known to those in the art, so that they can be readily prepared. Suitable culturing media are also commercially available.

The cDNA or genomic DNA encoding native or mutant 5'OT-EST can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and optionally a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA encoding 5'OT-EST is more complex than that of exogenously replicated vector because restriction enzyme digestion is required to excise 5'OT-EST DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up 5'OT-EST nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes 5'OT-EST. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to 5'OT-EST nucleic acid. Such a promoter may be inducible or constitutive. The promoters are operably linked to DNA encoding 5'OT-EST by removing the promoter from the source DNA by restriction enzyme digestion and inserting the isolated promoter sequence into the vector. Both the native 5'OT-EST promoter sequence and many heterologous promoters may be used to direct amplification and/or expression of 5'OT-EST DNA. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding 5'OT-EST, using linkers or adaptors to supply any required restriction sites. Promoters for use in bacterial systems will also generally contain a Shine-Delgarno sequence operably linked to the DNA encoding 5'OT-EST.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al., Methods in Enzymol. 185; 60–89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcH is Xpress™ (Invitrogen) or pTrc99 (Pharmacia Biotech, SE), or vectors containing the tac promoter such as pKK223–3 (Pharmacia Biotech) or PMAL (new England Biolabs, MA, USA).

Moreover, the 5'OT-EST gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

5'OT-EST gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with 5'OT-EST sequence, provided such promoters are compatible with the host cell systems.

Transcription of a DNA encoding 5'OT-EST by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to 5'OT-EST DNA, but is preferably located at a site 5' from the promoter.

Advantageously, a eukaryotic expression vector encoding 5'OT-EST may comprise a locus control region (LCR). LCRs are capable of directing high-level integration site independent expression of transgenes integrated into host cell chromatin, which is of importance especially where the 5'OT-EST gene is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding 5'OT-EST.

An expression vector includes any vector capable of expressing 5'OT-EST nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding 5'OT-EST may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding 5'OT-EST in mammalian cells. Transient expression usually involves the use of an expression vector that is able to replicate efficiently in a host cell, such that the host cell accumulates many copies of the expression vector, and, in turn, synthesises high levels of 5'OT-EST. For the purposes of the present invention, transient expression systems are useful e.g. for identifying 5'OT-EST mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing 5'OT-EST expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In a further aspect, the present invention provides a transgenic non-human animal which expresses, as a result of transformation with a transgene, 5'OT-EST or a mutant thereof as defined herein. Preferred animals include mammals, especially rats.

Preferably, the non-human animal is a mammal suitable for use as a test system for therapies and treatments relating to obesity, including human obesity and animal obesity, which is of concern in household animals such as cats and dogs. Thus, the mammal may be a cat or a dog, or other household pet; it is preferably a rodent, such as a mouse or a rat, particularly a rodent adapted for laboratory testing whose genotype and general characteristics are well known.

Any technique may be used to generate transgenic animals according to the invention. Preferably, the technique involves transfer of a transgene comprising 5'OT-EST to the pronucleus of a single-cell embryo, prior to implantation of the embryo into a pseudopregnant foster mother. Such techniques have the advantage that germ-line transgenic animals are readily produced.

Alternatively, transgenic animals may be created by ES cell transfer techniques. In such techniques, ES cells are transformed with the desired transgene and then used to reconstitute an embryo. Animals created by such techniques are normally chimeric for the transgene. However, more accurate positional insertion of the transgene is possible, and selective deletion of endogenous genes by homologous recombination is facilitated (Mansour et al., 1989).

Further techniques include targeted or non-targeted delivery of genes to whole animals, using viral or non-viral vectors. For example, genes may be delivered by recombinant retroviruses or adenovius vectors, including adeno-assisted virus vectors, which are capable of integrating into the genome of the animal and expressing the delivered gene. Non-viral vectors include liposomal vectors, antibody-targeted DNA-protein complexes and the like.

As used herein, "transgenic" animals include animals from which 5'OT-EST has been deleted, as well as animals to which a 5'OT-EST transgene has been added. Optionally, the endogenous 5'OT-EST may be deleted, and a transgene bearing a heterologous or homologous 5'OT-EST gene, which may be wild-type or mutated, inserted into the animal.

Preferred vectors for creating transgenic animals include linearised naked DNA from a variety of sources. In a preferred embodiment, transgenes may be derived from linearised cosmid sequences, from which the phage-related sequences have optionally been removed.

The 5'OT-EST sequences used in a transgene according to the present invention may be inserted separately, or together with further sequences, including reporter genes, further effector genes and the like. Preferably, 5'OT-EST is comprised in a nucleic acid fragment which comprises the natural wild-type environment of 5'OT-EST, including flanking sequences.

5'OT-EST is located proximal to the vasopressin (AVP) and oxytocin (OT) genes in the genome, being transcribed in opposite directions from positions closely linked in a single locus. 5'OT-EST lies 5' of the OT gene in at the OT/AVP locus. Accordingly, the transgene preferably consists of the OT/AVP locus, including 5'OT-EST. Advantageously, one or more of the OT, AVP and 5'OT-EST genes may be mutated, for example by insertion of reporter genes, such as the hGH gene.

Figure 4:
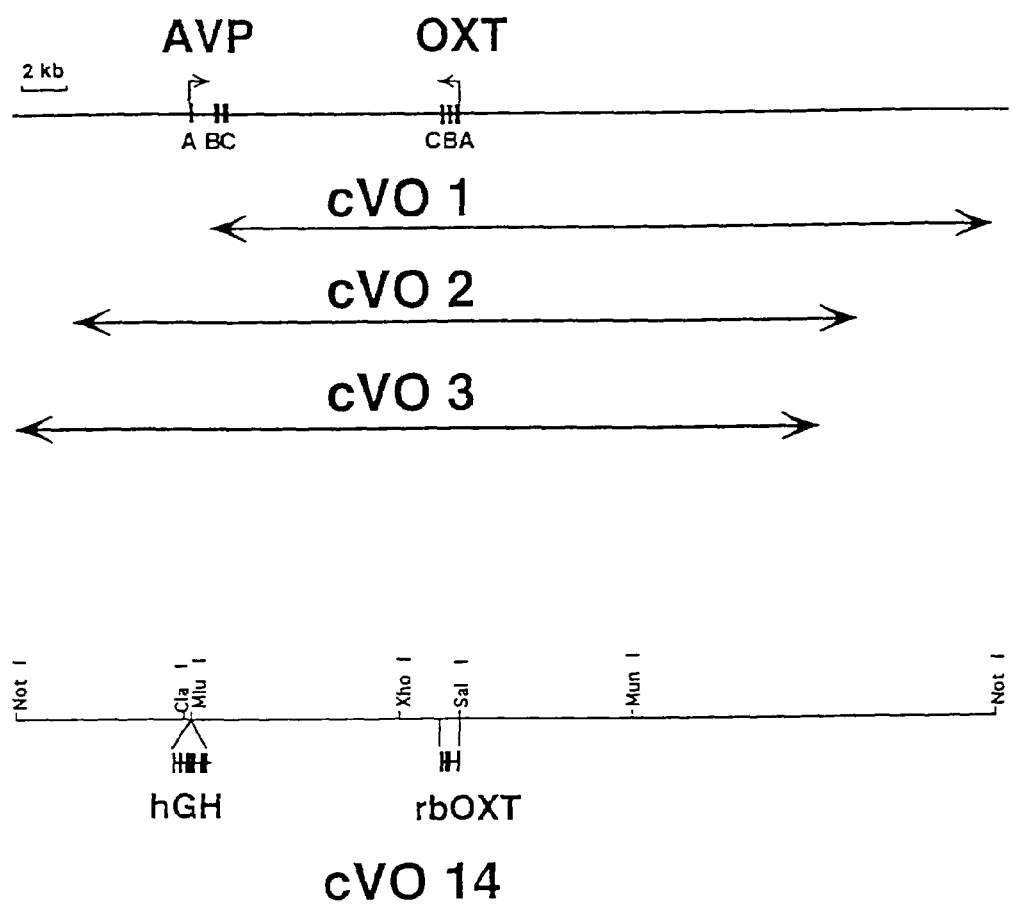
FIG. 4 shows the extent of the rat AVP/OT locus present in the cosmid cVO1, 2 and 3. These clones span a total of 44 kb, including 8 kb 5' of rAVP and 24 kb 5' of rOT. The structure of the final cosmid construct CVO14 is illustrated and some restriction sites indicated.

In a highly preferred aspect, the transgene is cosmid cVO14 as described in FIG. 4 herein. The complete sequence of cVO14 is set forth in SEQ. ID. No. 17.

Transgenic animals according to the invention may comprise single copies of the transgene, or may comprise multiple integrated copies, which may be present as concatamers. Preferably, transgenic animals according to the invention comprise four or more copies of the transgene.

Transgenic animals according to the invention may be employed for a variety of purposes. The characteristics of male specificity, central distribution of adiposity, late onset and severity, and associated morbidity have parallels in the description of several human forms of central obesity. These include, but are not limited to, the condition known as metabolic syndrome, or Syndrome X, as well as other forms of central obesity which may be most severely expressed in human males, with or without reduced fertility and which are associated with increased morbidity. (For recent reviews of the importance of clinical and health care issues in obesity see Science 1998, vol. 280 pp. 1364–1390). Transgenic animals expressing 5'OT-EST or mutants thereof thus have particular beneficial utility as a novel animal model of late-onset human visceral obesity, preponderant in males.

Moreover, the induction of the SLOB phenotype in juvenile rats as a result of dietary fat increases suggests that transgenic animals expressing 5'OT-EST are a model for juvenile obesity in mammals, predominantly male mammals, which is induced by the consumption of a high-fat diet.

Furthermore, the onset of obesity in ovariectomised SLOB female rats suggests the model may be suitable to investigate post-menopausal obesity in female mammals.

For instance, one recognised value of animals bearing 5'OT-EST or mutant constructs is to use such animals and their nontransgenic littermates as animal experimental models for studying obesity or male infertility and their related conditions. Using the information disclosed herein, it is possible to identify transgenic animals before they become obese or sexually mature, and to use them as a model for studying the factors that affect the development of obesity or male infertility in any animal classified as a mammal, including humans, domestic, and farm animals, and zoo, sports, or pet animals, such as but not limited to sheep pigs, cows, horses, dogs, cats, etc.

In particular, rodent models of obesity or infertility are of value in testing the ability of pharmaceutical preparations of novel agents, to be beneficial in delaying or preventing the occurrence, development, course, severity, progression, or exacerbation of obesity or infertility (Mathe, 1995; Fan et al., 1997). Animals bearing 5'OT-EST or mutant constructs are particularly useful in testing agents in this regard, since the phenotype is predictable and non-transgenic littermates are ideal controls.

In addition to screening for unknown compounds, animals bearing 5'OT-EST or mutants thereof may be particularly useful in studies employing administration of natural or recombinant proteins, peptides or other agents or their derivatives already known or suspected to be involved in some forms of obesity or male infertility (e.g. growth hormones, or reproductive hormones, their homologues, analogues, antagonists, inhibitors or secretagogues, or leptin, its homologues, analogues and antagonists) or other natural or pharmacological agents already known to be active and/or of therapeutic value in these conditions (e.g. insulin, thiazolidinones, catecholamines, gonadal steroids) or agents already known to affect their actions, distribution, catabolism or elimination).

Typically in such studies, compounds may be administered to animals bearing 5'OT-EST or mutants thereof and their non-transgenic littermates by oral, parenteral (e.g., intramuscular, intraperitoneal, intravenous, or subcutaneous injection or infusion, or implant), nasal, pulmonary, rectal, sublingual, or topical routes of administration, and can be formulated in dosage forms appropriate for each route of administration, e.g. in soluble form, suspension, or other suitable pharmaceutical formulations.

For example, the effects of such compounds on the obese phenotype may be assessed by carcass analysis, measurement of growth, body weight, body fat distribution, as well as other measures of analytes in body fluids or tissues relevant to obesity (Mathe, 1995; Shillabeer, 1992). These include, but are not limited to, cholesterol, triglycerides, fatty acids, lipoproteins, and other dietary constituents or metabolites, as well as metabolic hormones, such as leptin, insulin, glucagon, catecholamines or glucocorticoids. Other relevant parameters include cardiovascular measures (Reaven, 1988, Gray & Yudkin, 1997). These may include measures of systolic or diastolic blood pressure, cardiac output, or vascular resistance, together with morphological changes to organ systems known to be affected by cardiovascular or obesity disorders, such as heart, major or minor blood vessels, their muscle or endothelial layers, and their elasticity or fragility. See for example McNamee et al. (1994).

Similarly, parameters related to the infertility phenotype that may be measured, include, but are not limited to, testicular weight, volume, development, spermatogenesis, sperm number, motility or ability to fertilise oocytes. They may also include measures of testicular fluid production and constituents, as well as products of other accessory organs including seminal vesicles or prostate, as well as hormones, receptors, and proteins important in male sexual function, such as testosterone, LH, FSH, inhibin or activin. Other responses that may be affected include energy expenditure, physical activity, ingestive behaviour, excretory behaviour, or reproductive behaviour, or the organs, hormones or receptors commonly recognised to be associated with these physiological systems, their metabolism or morphological structure.

Compounds identified as effective in such screening or analysis based on the use of animals bearing 5'OT-EST or mutants thereof are particularly useful in treatment of late-onset visceral obesity, or male infertility, in particular where they occur in combination, and disorders related to these conditions with a view to delaying or preventing the occurrence, development, course, severity or progression of the phenotype, avoiding its exacerbation, and preferably promoting its amelioration or cure in animals of commercial importance, or more preferably in humans.

In another embodiment, converse but also therapeutically valuable compounds may be developed based on screening or analysis as above in animals bearing 5'OT-EST or mutants thereof but which are intended to promote the occurrence, development, or progression of increased fat deposition or increased calorie intake or decreased energy consumption, Such disorders in humans include, but are not limited to, wasting, or anorexia, or cachexia, associated with prolonged illness, or malabsorptive states or catabolic states associated with other diseases, such as, but not limited to, inflammatory conditions, Crohns disease, or AIDS wasting, or burns, or cancer, or bone disease.

Similarly, therapeutically valuable approaches may be developed based on screening or analysis as above in animals bearing 5'OT-EST or mutants thereof but which reduce the degree of male fertility in those conditions in which it might be beneficial. For example, this may be beneficial in the control of populations in animals of commercial or environmental importance, or to develop novel forms of contraception which may be effective in human males. Such approaches specifically include, but are not limited to, the possibility of blocking 5'OT-EST or mutants thereof function by administering 5'OT-EST mutant products or by immunisation against 5'OT-EST to generate neutralising antibodies that interfere with the normal functioning of this gene product in the testis, or hypothalamus or adrenal gland or gastrointestinal tract, or other organ system in which 5'OT-EST is expressed or upon which its products act.

The development and late-onset of obesity in transgenic animals may be particularly useful in studying the chronic effects of novel food additives or formulations designed to prevent or exacerbate the deposition of fat in animals of commercial importance, of destined for use in human food products or dietary aids. Such compounds may be administered as above and their effects on the development, course, severity, progression, exacerbation, amelioration or cure of the obesity phenotype assessed as described above. Additives or formulations shown to reduce the development of visceral obesity in this model may have utility in human food products or dietary aids or find beneficial medicinal use in reducing fat accretion or retention.

In another embodiment, transgenic animals, such as mice bearing 5'OT-EST or mutants thereof or in which 5'OT-EST has been disrupted, may be usefully intercrossed with other animal strains with defined mutations, or with undefined genetic backgrounds associated with propensity for the development of obesity or infertility. Comparison of the resulting progeny with or without the 5'OT-EST transgene will provide additional information on the alterations in occurrence, development, course, severity, progression, exacerbation, amelioration or cure of the obesity phenotype when expressed in these other genetic backgrounds, and analysed as described above. Such intercrossing may then be envisaged to enhance the utility of the resulting progeny exhibiting the obesity phenotype.

Examples of this use include (without being limited to) interbreeding with Zucker fa/fa rats (Iida et al., 1996), corpulent (cp) rats (Kahle et al., 1997), OLETF rats (Takiguchi et al., 1998), ZDF rats, tfm rats, spontaneously hypertensive or salt-sensitive rats (Michaelis et al., 1995) or other dwarf rats such as dw/dw (Charlton et al., 1988) or dr/dr rats (Takeuchi et al., 1991). An example of the utility of this approach is given by (Michaelis et al., 1995). Examples of mouse lines that may be usefully interbred with mice carrying transgenes or deletions affecting 5'OT-EST include, but are not limited to, ob/ob. db/db, tfm/tfm or hpg/hpg mice. A related example includes intercrossing mice carrying transgenes or deletions affecting 5'OT-EST with other strains of mice in which genes already known to be involved in obesity or male fertility have been deleted by homologous recombination or introduced by transgenesis (singly or in combination). Examples of these are already known to include (but are not limited to) leptin, tubby and related genes, NPY, insulin, GLP-1, IGF-1, IGF-II, MCH, CRH, POMC, CCK, orexins or hypocretins, CART peptides, agouti protein, as well as the genes or alternate products structurally related to or homologous with, the above peptides. This example is also intended to include mice with disruptions in or extra copies of normal or mutated forms of, genes for the specific receptors of the peptides listed above (for example NPY receptors, such as subtype 5), or bombesin-receptor 3, IRS-1 or 2, uncoupling proteins such as UCP1–3, carboxypeptidase E, or PPARs or adrenergic receptor subtype 3 or TNF alpha or, all of which have been implicated in obesity.

Similarly, the fertility disruption in transgenic animals according to the invention may also be studied to advantage by crossing these animals or other animals in which 5'OT-EST has been disrupted onto genetic backgrounds in which genes for gonadal or adrenal steroid biosynthesis or metabolism or gonadal steroid receptors and other reproductive hormones or their receptors or hypothalamic or pituitary hormones thought to affect male fertility (such as gonadotrophins, activins, inhibins, PRL, GNRH or transcription factors such as DAX1 or SF1, or other known gene products affecting male gonadal development, such as MIS, AMH, SCF) have been disrupted. Comparison of the resulting progeny with or without the 5'OT-EST or mutant transgene may shed light on the alterations in occurrence, development, course, severity, progression, exacerbation, amelioration or cure of the infertility phenotype when expressed in these other genetic backgrounds. Such intercrossed lines, for example with those genetic strains as outlined above, and in which the obesity phenotype is present in full or in a modified form, may also be additionally useful for screening applications.

Conversely, the transfer of the obese phenotype onto these genetic backgrounds may also alter the occurrence, development, course, severity, progression, exacerbation, amelioration or cure of the specific phenotypes expressed in the strain with which animals bearing 5'OT-EST or mutants thereof are bred. Such intercrossed lines, for example with those genetic strains as outlined above, and in which the obesity phenotype is present in full or in a modified form, may also be useful for screening applications.

Animals bearing 5'OT-EST or mutants thereof may be used to study the transfer of other gene products other than by breeding, e.g. by administration of suitable vectors containing constructs expressing proteins of interest, or by transgenesis. Such examples include, but are not limited to, constructs containing the gene products or analogues of other genes already thought to be active in obesity or male infertility, whose effects may be advantageously studied in transgenic animals according to the invention due to the predictable development of their phenotype. Such genes and their products include those mentioned in above in relation to alternative obese strains. Such derived animals in which the obesity phenotype is present in full or in a modified form, may also be useful for the various applications outlined above.

Animals bearing 5'OT-EST or mutants thereof and exhibiting a specific late-onset visceral obesity may prove of particular value when used in a similar way to screen for the beneficial effects of reducing or eliminating other gene products by their silencing or elimination as described above using transgenesis, or homologous recombination, or by adenoviral delivery of antisense nucleotides. Examination of any alterations in the occurrence, development, course, severity, or progression of the obesity phenotype in these genetic backgrounds would be of utility in identifying the role, if any, of such disrupted genes in the expression of the obesity phenotype. Such animals in which the obesity phenotype is present in full or in a modified form, may also be useful for the applications outlined above.

In another embodiment, animals bearing 5'OT-EST or mutants thereof or material derived from them and/or their nontransgenic littermates may prove useful in experiments designed to identify obesity-related or male-fertility-related differences in gene expression, RNA transcripts, proteins, or other biochemical measures, such as, but not limited to lipids, peptides, carbohydrates, amino acids or compounds or precursors or metabolites thereof, or their distribution, in whole animals, or in samples of biological fluids taken from animals bearing 5'OT-EST or mutants thereof. These may include, but are not limited to: serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts.

Similar analyses may be advantageously performed in samples of any tissue from animals bearing 5'OT-EST or mutants thereof or their non-transgenic littermates, or tissue derived from animals interbred with SLOB rats or other animals bearing 5'OT-EST or mutants thereof. Such tissues are preferably (but not limited to) endocrine tissues, such as pancreas, adrenals, or pituitary gland, adipose tissues from different locations, preferably but not limited to, inguinal, omental, perirenal, subcutaneous, mammary, periorbital or other regions, thermogenic fat, brown or white adipose tissue in other locations, areas of the CNS though to be involved in obesity, preferably but not limited to the hypothalamus, and other tissues, preferably, but not restricted to liver, gastrointestinal tract, gonads, heart, musculoskeletal system, immune system, kidney, connective tissue including skin, epithelial or endothelial tissues.

Specifically included are cells or tissues removed from animals bearing 5'OT-EST or mutants thereof, or animals interbred with them, and maintained thereafter ex vivo, e.g. in tissue culture, or by transplantation in animals bearing 5'OT-EST or mutants thereof or other hosts, with or without immune suppression, provided the particular utility is enhanced by the presence of the obesity gene or phenotype.

The invention thus provides the use of a tissue derived from a transgenic animal according to the invention in a screen to identify a genetic cause of obesity, comprising the steps of:

a) isolating one or more gene products from tissue derived from a transgenic animal as described herein; and
b) determining whether the expression of a gene product is correlated with obesity.

Tissues derived from SLOB rats, including in particular fat pad tissue, may for example be used for differential screening in order to determine differences in gene expression between obese and non-obese animals. The gene products analysed may be nucleic acid or protein gene products. For example, mRNA may be isolated from the tissue and screened to identify differentially expressed transcripts. In particular, gene products which may be involved in cellular lipid transport may be identified by such means.

The development of obesity or male infertility itself in animals bearing 5'OT-EST or mutants thereof is predicted to induce secondary changes in other obesity or fertility-related parameters and regulators. These include, but are not limited to, blood pressure, pituitary hormones, sperm development, maturation, and/or motility, lipid mobilising enzymes or receptors, or agents controlling these. The latter include, but are not limited to leptin and its receptors, melanocortin, NPY, catecholamines, adrenal or gonadal or pituitary hormones, gut hormones such as insulin and glucagon, growth hormone and other growth factors such as members of the GH and IGF-1 families, their binding proteins and receptors. They may also include drugs of several classes that have be thought useful in obesity. Examples of such classes include agents affecting the serotonin system or the fat cell free fatty acid uptake or release or metabolism or lipase activity or hepatic lipid uptake, or insulin sensitisers. This example may also include morphological alterations in any tissue or cells of the cardiovascular system, including but not limited to, the heart and major blood vessels, other blood vessels carrying either arterial or venous blood, and any or all cells comprising these tissues.

Transgenic animals according to the invention appear to present with obesity without obvious diabetes or hypercortisolism. They may thus prove particularly beneficial in studying the developmental changes in these secondary parameters induce by other means, in the development of diabetes, or hypertension or cardiovascular disease or hypercortisolism (Russell et al., 1993), all which are known to be associated with obesity in humans (Reaven, 1988). Examples of such means includes (but is not limited to) variation in dietary components or quantity, or treatment with diabetogenic agents, such as GH or cortisol. Examples of such agents affecting cardiac output or peripheral resistance or blood pressure include angiotensin-converting enzyme inhibitors or cardiac glycosides, or beta adrenergic receptor 3 agonists or antagonists.

Morphological changes may also be seen in adipose tissues or cells, or the other tissues in the body containing fat, such as the liver and related cells, or the skeleton, or in other organs or tissues in the gonadal system, relating to the effects on male fertility. Differences in these measures detected specifically in animals bearing 5'OT-EST or mutants thereof and their alteration by elimination, blockade, endogenous stimulation, or exogenous administration of anti-obesity or other agents affective in obesity or male infertility or related disorders would provide novel approaches to evaluate improve and perfect existing or novel therapeutic approaches to obesity or male infertility in other animals of commercial importance, and more preferably, in humans. An obvious example is the ready source of adipocyte cells and products from specific fat depots that are differentially increased in transgenic animals according to the invention. Responses to agents affecting fat cell metabolism or fat storage or lipogenesis or lipolysis or lipid-lowering agents, may be studied with particular advantage to discern effects on visceral or peripheral fat tissues, and to seek differential effects on fat from different depots in the animals.

The information disclosed herein will enable those skilled in the art to produce protein or peptide fragments corresponding in sequence to 5'OT-EST or mutants thereof, as described above. Such proteins or peptides (or simple analogues thereof), when administered to rats or other animals, or more preferably humans, would be expected to affect the development of obesity and fertility in males, and serve as the basis for the development of similar compounds, based on the homologous human sequences, useful in the treatment of these conditions in humans.

This also includes simple analogues that incorporate alterations known to improve the in vivo stability or delay the clearance, elimination or metabolism of proteins or peptides such as those derived from 5'OT-EST or mutants thereof. Such alterations are obvious to those skilled in the art, and examples include amidation or acetylation of C or N-termini of peptides, or replacement of methionine residues with norleucine residues to avoid oxidation. This example also includes formulations or modifications of proteins known to be effect for the same purposes, e.g. by PEGylation to prolong the half-life of peptides or proteins, or formulations of proteins with inert carriers (such as mannitol or lactose) or buffers or salts, that provide stable solutions suitable for in vivo administration of the active agents to animals or to humans.

In another embodiment, the information disclosed herein will enable those skilled in the art to design nucleotide probes for, or develop polyclonal or monoclonal antibodies against, the DNA, RNA or protein sequences corresponding to the whole or parts of the 5'OT-EST gene in other animals of commercial importance, or more preferably, humans. These are of value in diagnostic tests to screen for mutations in this gene in animal or human populations subject to variations in obesity or fertility. They may also be used to monitor the development, progression, amelioration or cure of obesity or infertility as may be reflected in changes in the activity of this gene or its products. Such predictive tests are recognised to have beneficial value when applied to the human population (Whitaker et al., 1997).

Examples of such probes or peptides or proteins used to develop antibodies include those predicted from the wild-type and mutated sequences in the rat 5'OT-EST gene and mutants thereof, as well as their derivatives as described above, as well as those that may be inferred from homologous genes in human and mouse, either as intact sequences or formed in whole or in part as fusion sequences with other proteins to facilitate production or purification by standard methods known to those skilled in the art. For this purpose, products of the 5'OT-EST gene may also be reacted with, produced as fusion products with, or mixed with, other proteins or adjuvants known to enhance the immune response. Also included are modifications to the nucleotide sequences, already known to those skilled in the arts to confer useful chemical properties on the products, for example by incorporating modified nucleotides to render them more stable, or to incorporate nucleotides tagged with functional groups such as biotin or digoxigenin, or incorporation of fluorescent or radioisotopically labelled derivatives, in order to render the products themselves more readily detectable.

In a further embodiment, the information disclosed herein will enable those skilled in the art to isolate factors which interact directly with 5'OT EST or mutants thereof. For example, two-hybrid screens provide a means for isolating genes for proteins which interact with 5'OT EST or mutant proteins, their fragments or derivatives. Similarly, co-precipitation studies using antibodies directed against 5'OT EST or mutants thereof, produced as outlined herein, might allow identification of such interacting factors. Such factors, when administered to rats or other animals, or more preferably humans, would be expected to affect the development of obesity and/or male infertility in a similar fashion to that seen in transgenic animals, and would therefore be predicted to have similar uses. The use of transgenic animals or materials derived from them, or from the information disclosed herein, has particular utility in providing a specific means of isolating such factors that interact directly with the novel gene products disclosed herein, as well as in screening their biological activities in vivo.

The invention is described further, for the purpose of illustration only, in the following examples.

Materials and Methods

Bacterial Cultures.

All media are made with double distilled water and autoclaved prior to use. Liquid cultures of bacteria are incubated with shaking at 37° C. in either LB broth or terrific broth. Bacterial colonies are grown on agar plates made with either LB broth or terrific broth with 15 g/l bacto-agar. These media are supplemented with combinations of 20 µg/ml or 50 µg/ml ampicillin, 20 µg/ml tetracycline and 0.2% glucose. Bacterial clones are stored at −80° C. after the addition of 15% glycerol.

Purification of Nucleic Acids.

Aqueous solutions containing DNA are purified by vortex mixing with an equal volume of phenol:chloroform:isoamyl alcohol (25:24:1). The emulsion is then centrifuged at 12,000 rpm for 5 minutes in a microfuge at room temperature. DNA is precipitated by adding 3M sodium acetate (pH 5.2) to a final concentration of 300 mM and two volumes of absolute ethanol. The samples are frozen before centrifugation, the supernatant removed and the pellet resuspended in 10 mM Tris.HCl pH 8, 1 mM EDTA (TE buffer).

DNA Preparation from Bacteria Stocks.

The alkaline lysis method of DNA isolation may be used (Birnboim and Doly, 1979; Sambrook et al., 1989) to prepare plasmid DNA from small volumes of bacterial cultures, typically 10 ml. For large scale preparation of plasmid and cosmid DNA, DNA may also be prepared from 1 L overnight cultures by the alkaline lysis method. DNA is dissolved in 100 mM Tris.HCl pH 8, 1 mM EDTA and further purified on a caesium chloride gradient which is centrifuged at 55,000 rpm overnight (Sambrook et al., 1989).

Preparation of Genomic DNA from Animal Tissue.

Rat tail biopsies, up to 1 cm, are taken from 10–14 day old rats and placed in 50 mM Tris.HCl pH8, 100 mM EDTA, 100 mM NaCl ('tail mix'). Genomic DNA is prepared following a standard procedure (Hogan et al. 1986) involving incubation with proteinase K, RNase A, phenol extraction and precipitation with isopropanol. Genomic DNA from other tissue such as liver may be prepared by the same method, though this requires additional homogenisation in a larger volume (typically 5 ml) of tail mix using a Kinematica Polytron PT 3000 homogeniser prior to the preparation of DNA from a smaller aliquot of homogenate.

Restriction Digestion of DNA.

Restriction enzyme digestion is performed using standard procedures in accordance with manufacturers instructions. Enzymes are sourced from Boehringer Mannheim, Cambio, or New England Biolabs. Plasmid DNA is incubated for up to 4 hours whilst genomic DNA digests may be incubated overnight.

Subcloning DNA Fragments into Plasmid Vectors.

Blunting of DNA Fragments with a 3' Overhang

After digestion of DNA with a restriction enzyme which leaves a 3' overhang, the overhang may be removed by incubation with T4 DNA polymerase to create a blunt end for ligation with other blunt-ended DNA fragments. The digests are phenol-extracted, ethanol-precipitated with the addition of 10 μg tRNA, and resuspended in TE. $MgCl_2$ and deoxynucleotide triphosphates (dNTPs) are added to final concentrations of 10 mM and 0.1 mM respectively prior to the addition of 2 units of T4 DNA polymerase (New England Biolabs). The reaction is incubated for 15 minutes at 12° C. The polymerase is inactivated at 75° C. for 10 minutes before purification.

Blunting a DNA Fragment by Refilling the 5'Overhang.

DNA fragments with 5' overhangs may be blunted by filling in the single stranded ends. This may be done using the Klenow fragment of *E. coli* DNA polymerase I (New England Biolabs). The DNA is digested with an appropriate restriction enzyme, phenol extracted, ethanol precipitated with the addition of 1 μg of tRNA and resuspended in TE. 10× Klenow buffer (0.5M Tris.HCl, pH7.6, 0.1M $MgCl_2$) and dNTPs to a final concentration of 1× and 0.2 mM respectively are added with 10 units of Klenow fragment. The reaction is incubated at 37° C. for 30 minutes prior to purification of the DNA.

Vector Dephosphorylation.

Calf alkaline phosphatase (CAP) may be used to remove 5' phosphate groups from digested vectors to prevent self-ligation during subcloning. Plasmid and cosmid vectors, linearised with restriction enzymes, are incubated with 2 units of CAP (Boehringer) in 50 mM Tris.HCl, pH 8.5, 50 mM EDTA, for 30 minutes prior to purification.

Inserting Linkers into DNA Fragments.

Digested plasmid DNA may be blunted if necessary, phenol-extracted, ethanol-precipitated with the addition of 1 μg of tRNA and resuspended in TE. 0.5–1 μg of phosphorylated linkers are ligated to linearised, blunt-ended plasmid DNA. Ligations are performed in a final concentration of 1× ligase buffer (50 mM Tris.HCl (pH 7.5), 10 mM $MgCl_2$, 10 mM dithiothreitol, 1 mM ATP, 25 μg/ml bovine serum albumin (BSA), 0.5 mM spermidine-HCl with the addition of 400 units of T4 DNA ligase (New England Biolabs). The reactions are incubated at room temperature overnight. The enzyme is then inactivated at 65° C. for 15 minutes. The Tinkered fragments are digested with an excess amount of the appropriate restriction enzyme and the DNA purified prior to further subcloning procedures.

Electrophoresis of DNA Fragments

DNA fragments may be electrophoresed in gels of varying percentages of agarose in 90 mM Tris-borate, 2 mM EDTA, pH 8.0 (TBE buffer) containing 0.5 ng/ml ethidium bromide. The DNA bands are visualised on an ultraviolet transilluminator and photographed. Size markers may be Lambda DNA digested with Bst EII, pUC19 DNA digested with Msp I, or a commercially available 1 kb ladder (Gibco-BRL).

Purification of DNA Fragments.

Digested, blunted, dephosphorylated or Tinkered DNA fragments are electrophoresed in low melting-point agarose. Gel bands are excised, melted at 65° C. for 5 minutes, and extracted twice with phenol/0.3M NaOAc. Following a phenol extraction and ethanol precipitation with the addition of 1 g tRNA, the DNA is recovered by centrifugation and resuspended in TE. Alternatively, DNA fragments may be purified from agarose using the Prep-A-Gene DNA Purification System (Bio-Rad Laboratories) according to manufacturers instructions.

Purification of Larger Cosmid-Containing Fragments.

Large vectors are digested and treated with 50 units of CAP for in excess of 3 hours. EDTA and SDS are added to final concentrations of 5 mM and 0.5% respectively. The phosphatase is denatured for 1 hour at 65° C. and the solution is phenol-extracted, ethanol precipitated with the addition of 1 μg tRNA, and the DNA recovered is resuspended in TE.

Ligation of DNA Fragments into Phosphatased Vectors.

After purification, DNA fragments and vectors are mixed at equimolar ratios at an approximate concentration of up to 80 ng/ml, whilst DNA for recircularisation is used at a concentration of 20 ng/ml. Ligation may be done in a volume of 5 μl with 200 units of T4 DNA ligase (New England Biolabs) in ligase buffer. Two control reactions are performed simultaneously omitting the insert alone, or omitting both insert and ligase. Ligations are incubated overnight at 16° C.

Preparation of Competent Cells.

psi-broth 5 g/l bacto-yeast extract, 20 g/l bacto-tryptone, 5 g/l $MgSO_4$, adjusted to pH 7.6 with NaOH.

TFbI 30 mM KAc, 100 mM KCl, 10 mM $CaCl_2$, 50 mM $MnCl_2$, 15% glycerol (v/v), adjusted pH 5.8 with acetic acid and filter sterilised.

TFbI 10 mM PIPES, 74 mM $CaCl_2$, 10 mM KCl, 15% glycerol (v/v), adjusted to pH 6.5 with acetic acid and filter sterilised.

Competent cells yielding a transformation frequency >5×10$^8$ transformed colonies per μg of supercoiled plasmid DNA may be prepared by a method modified from Hanahan et al. (1983). Bacteria of the strain DH10B (Grant et al., 1990) are plated on an agar plate and grown overnight at 37° C. 10 ml of psi-broth is then inoculated with 4 colonies from this plate. The bacteria are then shaken at 37° C. until OD550=0.3.

5 ml of this broth is then diluted into 100 ml psi-broth and shaken until OD550=0.28. The flask is then placed on ice, the bacteria are centrifuged at 4° C. for 15 minutes at 2,000 rpm. The supernatant is removed and the pellet allowed to dry briefly before being resuspended in 20 ml TFbI. This suspension is left on ice for 5 minutes and then centrifuged at 2,000 rpm for 10 minutes at 4° C. The supernatant is then removed and the pellet resuspended in 3 ml TFbII and placed on ice for 15 minutes. Aliquots are then frozen on dry ice and stored at −80° C. The competence of the cells may be tested by transforming plasmid DNA of known concentrations.

Transformation of Competent Cells.

Competent cells are thawed on ice before 50 µl of cells is added to each ligation. These tubes are then incubated on ice for 30 minutes. The cells are then subjected to heatshock at 42° C. for 90 seconds before being placed on ice for 2 minutes. 0.4 ml of LB broth is added and the culture is shaken at 37° C. for 1 hour. Cells are then incubated overnight at 37° C. on agar plates containing the appropriate antibiotic. Single colonies are picked with a flamed wire loop and used to inoculate 10 ml of media for miniprepa-ration of plasmid DNA.

Packaging of Cosmid DNA into Bacteriophage Particles.

Cosmid constructs may be packaged into bacteriophage particles using Gigapack II packaging extracts (Stratagene) and *E. coli* strain DH10B is infected in accordance with manufacturer's instructions.

Southern Blotting.

DNA (10 µg of genomic DNA or 0.5 µg of plasmid DNA) is digested with appropriate restriction enzymes and elec-trophoresed on agarose gels with marker DNA of known size. After photography, gels are treated as described by Sambrook et al. (1989) and the DNA transferred from the gels onto nitro-cellulose filters by the capillary transfer method (Southern, 1975; Sambrook et al., 1989) and these are then baked for 2 hours.

Radiolabelling of DNA Fragments for Southern Blots.

DNA probes are obtained by gel purifying appropriate fragments from restriction digests of subcloned DNA. The DNA is denatured by being incubated for 3 minutes in a boiling water bath. The resulting single-stranded DNA frag-ments are radiolabelled with $\alpha$-$^{32}$PdCTP, e.g. by the random primer labelling kit, Prime-It II supplied from Stratagene, in accordance with manufacturer's instructions. The labelling reaction is halted by the addition of TES buffer to a final concentration of 10 mM Tris.HCl (pH 7.5), 10 mM EDTA, 0.1% SDS. Radiolabelled DNA probes are separated from unincorporated nucleotides by eluting through a column containing Sephadex G-50.

Hybridisation of Southern Blots.
100× Denhardts solution
  2% BSA, 2% Ficoll 400, 2% Polyvinyl Pyrollidine.
1M sodium phosphate buffer (pH6.6)
  352 ml 1M $Na_2HPO_4$, 648 ml 1M $NaH_2PO_4$.
Prehybridisation mix
  0.1 mg/ml tRNA, 5× SSC 50 mM Na Phosphate buffer (pH 6.6) 10× Denhardts solution, 1% SDS.
Hybridisation mix
  Prehybridisation mix with the above described radiola-belled DNA probe.

Filters from Southern blotting are gently shaken at 65° C. in prehybridisation mix for a minimum of 2 hours. This solution is then replaced with hybridisation mix and incu-bated overnight. The filters are washed in varying concen-trations of SSC with 0.1% SDS for varying amounts of time dependent on the DNA probe being used. Filters are then dried and placed between two intensifying screens at −70° C. with Kodak "Xomat-AR" film.

Screening a Rat Cosmid Library

Duplicate filters from a Wistar rat cosmid library contain-ing genomic DNA inserts in the pWE15 cosmid vector (Wahl et al. 1987) are prehybridised and hybridised with probes for the rat OT and AVP genes. Following overnight hybridisation, filters are washed with 3× SSC/0.1% SDS for 20 minutes and then SSC/0.1% SDS twice for 20 minutes.

Filters are briefly washed in 2× SSC, dried and autoradio-graphed. Duplicate hybridisation signals are aligned with the master filters and bacteria are picked, placed in media and left to diffuse. The resulting cultures are grown on terrific broth agar with 20 µg/ml ampicillin and replica plated. Replica plating of the bacterial culture from the library screening may be performed as previously described (Sam-brook et al., 1989). Replica filters are prehybridised and hybridised as above. Positively-hybridising colonies are picked from the master filters and grown in larger volumes of ampicillin-supplemented media for minipreparation and southern blot analysis of the cosmid DNA.

Purification of DNA for Microinjection.

50–100 µg of DNA is digested with Not I to separate the cVO14 cosmid insert from vector DNA. A salt gradient may be used as described by Dillon et al. (1993) to purify the 44 kb fragment. A gradient former is used to pour a gradient ranging in NaCl concentration from 5-25%. The digested DNA is applied to the top of the gradient which is then centrifuged at 5.5 hours at 37,000 rpm. The solution is then removed in 500 µl aliquots which are examined by electro-phoresis. Fractions containing the fragment to be microin-jected are pooled and ethanol precipitated. The pellet is dissolved in microinjection buffer (10 mM Tris.HCl, pH 7.5, 0.1 mM EDTA). DNA may be purified further using an Elutip column (Schleicher and Schuell) according to manu-facturers instructions. cVO14 DNA at a concentration of 1–10 ng/µl, typically 2 ng/µl, is used to generate transgenic rats.

Superovulation, Microinjection and Embryo Transfers.

40 day old prepubertal female Wistar rats are given intraperitoneal injections of 30 IU pregnant mare's serum (Folligon, Intervet Laboratories Ltd) between 9 and 11 o'clock on day −3. The same rats are injected i.p. at midday on day −1 with 22.5 IU human chorionic gonadotrophin (Chorulon, Intervet Laboratories Ltd) and placed in a cage with a stud male of the same strain. On day 1, females are killed and their oviducts removed and placed in M2 media (Hogan et al., 1986). The oviducts are dissected to release the eggs which are subsequently placed in M2 media with 0.5 mg/ml hyaluronidase (Sigma) in order to remove the cumulus cells surrounding the eggs. After 5 minutes the eggs are removed from the hyaluronidase solution, washed thor-oughly in M2 and placed in the unbuffered M16 (Hogan et al., 1986) in a 37° C. incubator supplemented with 5% $CO_2$. After 2 hours of incubation the male pronuclei of the eggs are microinjected using standard procedures and equipment (Hogan et al., 1986). Microinjected eggs are incubated overnight at 37° C.

The following day (day 2), eggs which have divided to the two-cell stage are washed in M2 media and transferred into the oviducts of pseudo-pregnant adult Wistar rats which have been mated with vasectomized male rats the previous night. The surgery is performed under halothane anaesthetic, with between 15 and 20 eggs being transferred into each infundibulum. Resulting litters are tail-clipped at 2 weeks of age. The tails are used for DNA preparation as described above and analysed by Southern blotting for animals con-taining transgenes also as described above.

RNA preparation.

RNA may be prepared from rat tissue by the acid guanidium thiocyanate-phenol-chloroform extraction method (Chomczynski et al., 1987). Briefly, tissue is homogenised in 500 µl 4M guanidium thiocyanate, 25 mM Sodium citrate (pH 7.0), 0.5% (w/v) sodium N-lauroylsarcosine, 100 mM 2-mercaptoethanol prior to the addition of 33 μl 3M sodium acetate (pH 4.1), 500 μl phenol and 100 μl chloroform. The mixture is vortexed and placed on ice for 15 minutes before centrifugation at 12,000 rpm for 10 minutes at 4° C. The aqueous fraction is decanted into a fresh tube and precipitated with isopropanol.

In Vitro Transcription.

A plasmid containing a T7 polymerase promoter 5' to the inserted sequence is linearised with a restriction enzyme which cuts at the 3' end of the insert. Transcripts are then obtained of the subcloned fragment using a T7 transcription kit (Boehringer Mannheim) according to the manufacturer's instructions.

DNA Sequencing.

Sequencing of DNA plasmid Subclones may be performed manually with the Sequenase version 2.0 sequencing kit (United States Biochemicals) which employs the chain-termination method (Sanger et al. 1977), or by automated sequencing using an ABI Prism DNA Sequencing Kit and 377 DNA Sequencer (Perkin Elmer Applied Biosystems) according to manufacturer's instructions.

Reverse Transcription of RNA.

RNA may be converted to cDNA using Superscript II reverse transcriptase (GibcoBRL) according to the manufacturer's instructions, in combination with either an oligo dT primer or another specific primer complementary to the RNA sequence of interest.

Polymerase Chain Reaction amplification of DNA.

The polymerase chain reaction (PCR) may be used to amplify fragments of DNA using 50 μl of a reaction mix which contains 10 mM Tris, pH8.3, 20 mM KCl, 0.2 mM dNTPs, 200 nM primers, 50–250 ng template DNA, 2.5 units Amplitaq DNA polymerase and 1–3 mM $MgCl_2$ (the optimal conditions for each amplification are determined empirically). Conditions vary for each template target, but a typical amplification might be to place the reaction mix in a thermal cycler (MJ Research Inc.), denature for 2 minutes and then subject the reaction to 34 cycles of 94° C. for 1 minute, 58° C. for 1 minute and 72° C. for 1–5 minutes, depending on the length of the expected product.

Cloning of PCR Products.

Products generated by PCR may be cloned using a TOPO TA Cloning kit (Invitrogen) according to the manufacturer's instructions.

Nuclease Protection Assay.

Riboprobe transcripts incorporating $^{32}P$ may be generated by transcribing approximately 250 ng of DNA fragment in Transcription Optimised buffer (Promega), 500 mM ATP, GTP and CTP, 20 units Rnasin RNA inhibitor (Promega), 20 mM UTP, 100 μCi $\alpha$-$^{32}$PUTP (Amersham) and 20 units of the appropriate RNA polymerase (Promega) at 37° C. for 90 minutes. After treatment of the reaction with 2 units of DNase I (Promega) at 37° C. for 20 minutes, the reaction is denatured and purified by polyacrylamide electrophoresis, followed by excision of the labelled RNA and elution in 350 μl of Elution buffer (Ambion) for 2 hours at 37° C. Nuclease protection may be performed essentially as described by Lee and Costlow (1987) using $^{32}$P-labelled riboprobe with 1–20 μg total RNA and the RPAII Ribonuclease Protection Kit (Ambion) according to the manufacturer's instructions.

In Situ Hybridisation.

Sense and anti-sense riboprobe transcriptsmay be generated using an SP6/T7 transcription kit (Boehringer) with $^{35}$S-UTP (NEN Research Products) according to the manufacturer's instructions. In situ hybridisations may be performed as described in Bennett et al. (1995). Autoradiographs are analysed densitometrically, from a light box using a video camera linked to a Power Macintosh 7600/132 running the programme NIH Image version 1.61.

Immunocytochemistry

Human growth hormone (hGH) may be localised in pituitary and brain sections using a modified avidin-biotin complex immunocytochemistry technique (Bourne et al., 1984). Tissue is collected and fixed in 4% paraformaldehyde for 24 hours. Tissues may be stored at 4° C. in 70% ethanol before embedding in paraffin wax and sectioning. Tissue sections (6 μm) are dewaxed in Histoclear (National diagnostics) and rehydrated by sequential 20 sec washes of 100%, 70% and 30% ethanol followed by a 1 min wash in distilled $H_2O$. Endogenous peroxidase activity is inhibited by a 30 min incubation in 3% (v/v) hydrogen peroxidase in methanol. Sections are then washed in distilled $H_2O$ for 1 min before being treated with 0.1% (w/v) trypsin (Sigma) for 15 min at 37° C. followed by 0.5% (v/v) Triton X-100 (Sigma) for 15 mins. After two 5 min washes of distilled $H_2O$ and 0.05M Tris buffered saline (pH 7.6), 0.15M NaCl (TBS) the sections are incubated with 20% (v/v) normal rabbit serum (DAKO) with 5% (w/v) BSA for 30 mins in order to reduce non-specific background staining. The sections are then incubated overnight in a humidity chamber at 4° C. with an antibody specific for hGH, such as sheep anti-hGH primary antibody (1:30,000) (Scottish Antibody Production Unit).

Following two washes in TBS, sections are incubated with biotinylated rabbit anti-goat serum (DAKO, 1:200) for 30 mins. The sections are again washed in TBS and incubated for 30 mins with avidin complexed to biotinylated horse radish peroxidase (DAKO). Human GH immunoreactivity is then visualised by development using 3,3-Diaminobenzidine tetrachloride/hydrogen peroxide (DAB) (4 mg/10 ml in 0.05M Tris buffer pH 7.6) containing 3% (v/v) $H_2O_2$. This reaction is quenched in distilled $H_2O$ prior to counterstaining with Gill's haematoxylin (BDH) and coverslipped for microscopic examination.

Radioimmunoassays

Tissue samples are homogenised in varying volumes of phosphate buffered saline with either glass homogenisers (for volumes up to 1 ml) or a Kinematica Polytron PT 3000 homogeniser (for larger volumes). The same polyclonal sheep anti-hGH antibody (Scottish Antibody Production Unit) may be used to measure hGH in tissue extracts by RIA as described in Fairhall et al. (1992) using recombinant hGH as standard. AVP may be measured by RIA as described in Horn, Robinson & Fink (1985). Rat GH may be measured as in Charton et al., (1988). Bovine neurophysin may be measured by RIA using a specific antiserum that does not recognise rat neurophysins (Gordon Weeks, 1987). Rat leptin and rat insulin may be measured by specific RIAs using kits from Linco Research Inc, following the manufacturer's instructions. Corticosterone may be measured by a double antibody RIA kit obtained from ICN Biomedicals. Cholesterol and triglycerides in blood samples may be measured using kits obtained from Sigma Diagnostics ('Cholesterol 20' and 'Triglycerides, UV'). Plasma glucose values may be measured using a Beckman glucose analyser.

EXAMPLE 1

Isolation of Cosmid DNA, Construction of Transgene Cosmids and Generation of Transgenic Rats Isolation of Cosmid DNA Since the DNA sequences of the rat AVP and OT genes and their orientation and structural relationship to each other in the rat genome are known (Ivell & Richter, 1984a; Mohr et al. 1988; Schmitz et al., 1991) the size of restriction fragments which should be detected with cDNA probes for these genes can be predicted. Colonies bearing rat DNA which contained fragments hybridising to these OT and AVP probes in the same areas in duplicate filters from the cosmid screening are aligned with the original bacterial plates. These colonies are picked and grown and DNA prepared from them, digested with Hind III, run on agarose gels, Southern blotted and hybridised to the same OT and AVP probes again. Three positive colonies are chosen for further analysis because their differing restriction fragment patterns indicated that they spanned different regions of the rat AVP/OT locus. From Southern blotting of restriction digests using probes against the first exon of each gene and the vector, they are found to span a total of 44 kb, including both genes, the 11 kb intergenic region, 8 kb of AVP 5' flanking sequence and 24 kb of OT 5' flanking sequence. These three overlapping cosmids are designated cVO1, 2 and 3. An overall schematic map of this region, indicating the location and orientation of AVP and OT genes, the location of some important restrictions sites, and areas of sequence known or subsequently determined and disclosed here, is shown in FIG. 1.

To facilitate further restriction mapping of the 5' flanking sequence of the rat OT gene, 8 kb and 14 kb Sma I fragments and an 8.5 kb Kpn I fragment are subcloned into cloning vectors and subjected to further restriction mapping. Smaller fragments of the OT and AVP genes are also subcloned into pUC 19 derived plasmid vectors and used to remove restriction enzyme sites and to insert the reporter genes into the rat OT and rat AVP loci. Oligonucleotide linkers containing sequences for unique restriction sites are also inserted in the 5' untranslated regions of the two genes to allow for future modifications of this construct.

Figure 2:
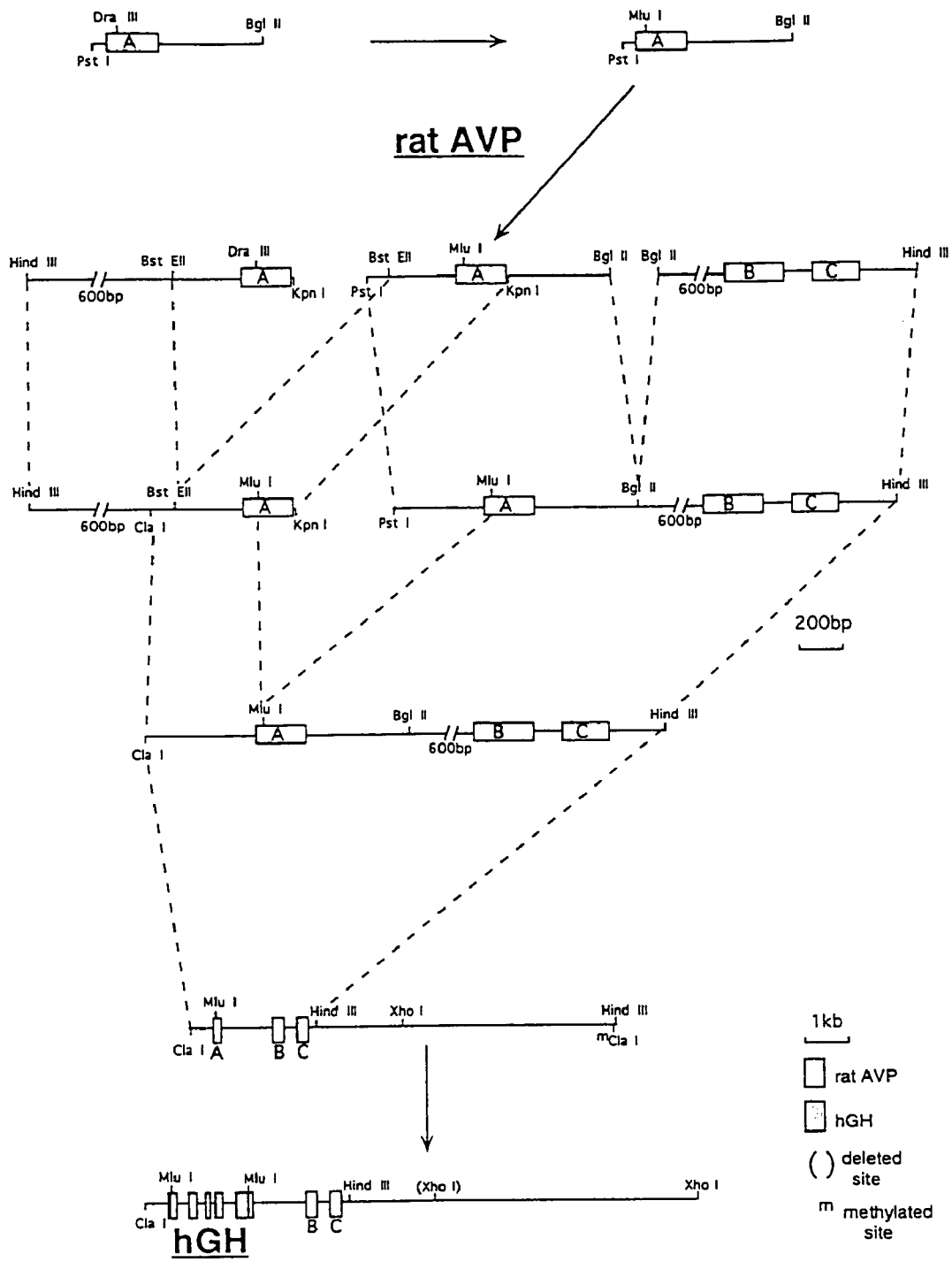
FIG. 2 is a diagrammatic representation of the subcloning steps leading to the insertion of the hGH reporter gene into the 5' untranslated region of the rat vasopressin gene. The final subclone shows the Cla 1 to Xho 1 fragment which was inserted into the construct used to make transgenic lines.

The subcloning strategy used for the AVP locus is outlined in FIG. 2 Essentially, the aim is to insert a genomic hGH reporter fragment in a unique cloning site introduced into the 5' untranslated region of rat AVP gene. Swanson et al. (1985) had previously shown that hGH reporter transcripts, when fortuitously expressed, may be expressed and translated efficiently in these neuronal cells types. Furthermore, hGH nucleotide sequences can be differentiated from rat GH sequences by specific nucleotide probes (Seeburg et al., 1977; Roksam & Rougeon, 1979) and the protein can be differentiated from rat GH by specific antisera (Appendix 1). An Mlu I linker is initially inserted into a smaller subclone of the rat AVP gene, replacing the Dra III site in the 5' untranslated region. A genomic fragment of the human GH structural gene (Roksam & Rougeon, 1979) is then inserted as an Mlu I-linkered fragment spanning from the 5' untranslated region of the hGH gene to a region 3' of the last exon and containing all 5 exons and 4 introns of hGH. This AVP-hGH fragment is inserted as a 12.2 kb Cla I-Xho I fragment containing 450 bp 5' and 8 kb 3' of the transgene, with deletion of other Xho I restriction sites.

Figure 3:
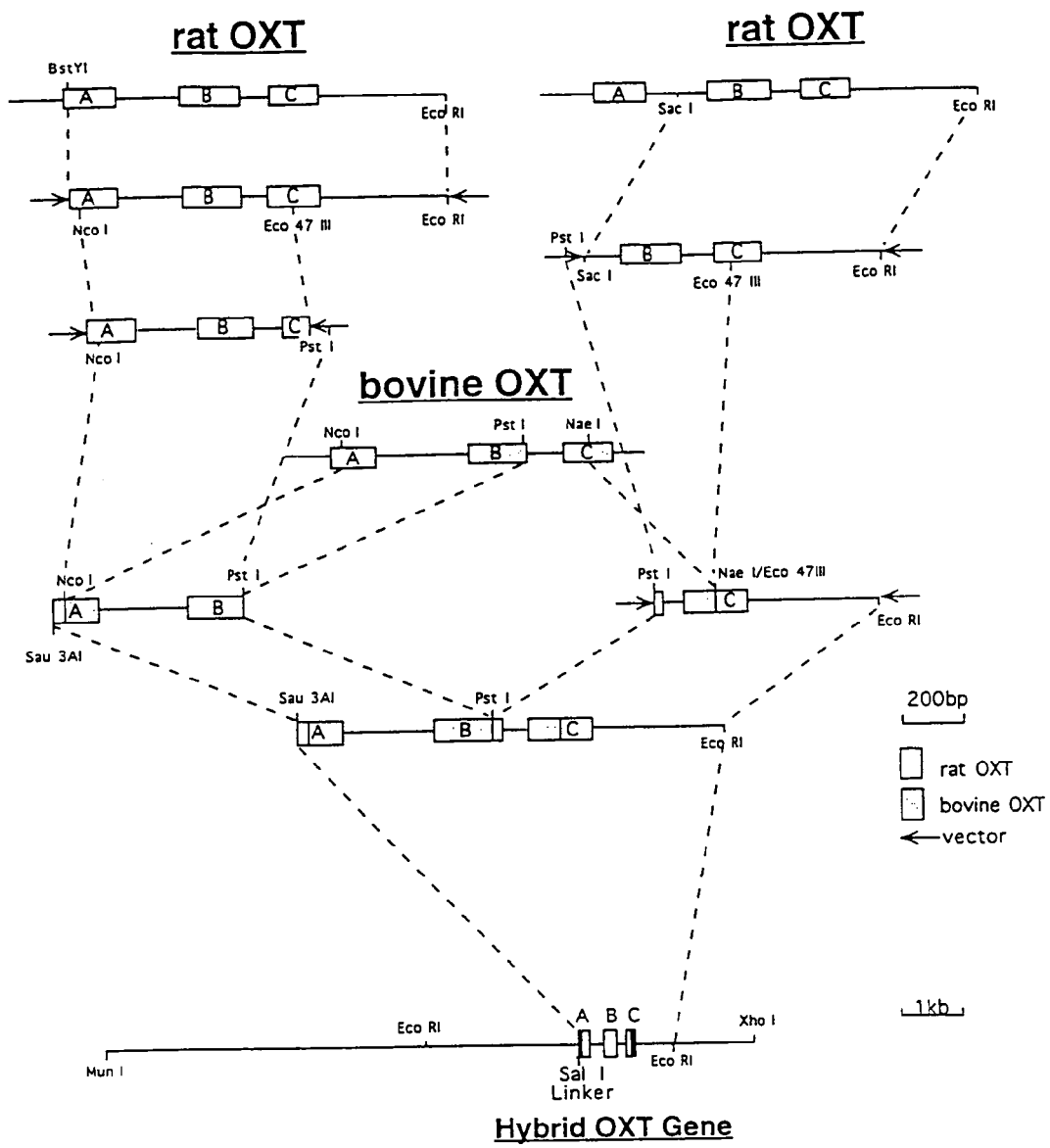
FIG. 3 is a diagrammatic representation of the subcloning steps required for the production of the rat-bovine hybrid gene which was inserted into the final construct. For simplicity, this is shown in reversed orientation compared to its orientation in the construct.

The subcloning strategy used for the OT locus is outlined in FIG. 3. In this case the aim is to replace most of the rat OT structural gene with corresponding bovine sequences (Land et al., 1983). The protein produced should function identically, but the bovine sequences would provide a 'silent' reporter since they could be differentiated from rat sequences (Mohr et al., 1988) by specific nucleotide probes, and the protein differentiated from rat neurophysin by specific antisera. Rat neurophysin has previously been used as a transgene reporter in mice (Belenky et al., 1992). Due to the constraints of suitable restriction sites it is necessary to assemble a 5' construct of the hybrid rat/bovine OT gene (containing exon A and most of exon B) and a 3' construct (containing a small fragment of exon B and exon C) separately. These constructs are joined to produce the hybrid gene with the 5' and 3' flanking sequences being added in subsequent steps. A Sal I linker is also inserted immediately 5' to the translational start site of the bovine OT to provide a unique cloning site within the AVP/OT locus for future modification of the construct. The hybrid gene is inserted into the final construct as a 10.5 kb Mun I-Xho I fragment containing 7.8 kb of 5' and 1.7 kb of 3' flanking sequence, after deleting other restriction sites within the cosmid.

Assembly of the Final Construct.

The pWE15 vector is modified to remove the unrequired SV2 neomycin gene. This reduced the vector size from 8.5 kb to 4.2 kb and therefore increased the size of the insert that could be subcloned into the cosmids, which can efficiently package up to 52 kb (Wahl et al. 1987). Cla I, Mun I, Sal I and Mlu I restriction sites are also removed from the vector to permit subsequent cloning steps. The pWE15 cosmid vector has Not I sites flanking the insert.

Restriction mapping of cVO1 revealed a Not I restriction site 13 kb upstream from the rat OT gene (FIG. 1) which would also be digested if Not I is used to remove the insert. Therefore, a 4.6 kb Aat II-Sca I fragment containing this site is subcloned, the Not I site deleted, and the fragments ligated and replaced into the construct. Digestion of the ligation product with Not I confirmed that this site had been destroyed.

The modified OT and AVP gene fragments are inserted into cVO3, followed by addition of the 5' region present in cVO1 but not in cVO3 using an Aat II fragment. This adds all except 1.1 kb of the extreme 5' end of cVO1 and contains a Not I linker at the extreme 5' end.

The final construct, termed cVO14, spans 44 kb and includes 8 kb 5' of rat AVP, 24 kb 5' of rat OT and 11 kb of intergenic sequence. The construct has reporter gene hGH sequences inserted into the 5' untranslated region of the rat AVP gene and parts of the bovine OT gene sequences substituted for equivalent rat OT gene sequences. The final cVO14 construct is illustrated diagrammatically in FIG. 4.

Generation of Transgenic Rats Bearing the cVO14 Construct.

The 44 kb Not I insert is released from cVO14 by Not I digestion, purified on a salt gradient and microinjected into fertilised rat oocytes. These embryos are transferred into pseudopregnant mothers and the offspring are analysed for the presence of the transgenes. Genomic DNA prepared from tail biopsies of these pups is digested with Bgl II, Southern blotted and hybridised with a radiolabelled genomic hGH probe that should identify 2 predicted fragments of 0.9 and 2.1 kB from transgene DNA. This probe does not detect endogenous rat GH sequences. Of 102 pups the hGH transgene is present in the DNA of only 3 pups, termed JP 17, JP 19 and JP 59. JP 19 dies at 11 days of age, and is not analysed further.

Other samples of DNA from the two remaining rats is digested with Pst I, Southern blotted and hybridised with a radiolabelled probe that should identify two predicted fragments of 0.9 and 1.6 kB from the hybrid rat/bovine transgene sequence, and a single 2.5 kB fragment from the endogenous OT gene. Both JP 17 and JP59 rats are also found to contain this hybrid gene, as well as the endogenous gene, whilst only the endogenous fragment is visualised in DNA from non-transgenic rats.

DNA from JP 17 and JP 59 rats is also Southern blotted and probed with radiolabelled DNA fragments corresponding to the ends of the cVO14 construct, which confirmed that whole copies of the microinjected fragment are present in both rats. The copy number of the transgenes is estimated by Southern blotting of Hind III fragments and hybridisation with a probe for the rat AVP gene sequences, which recognised a 3.4 kb fragment corresponding to the endogenous rat AVP gene and a 5.2 kb fragment which represents the transgene with its hGH reporter gene insertion. Assuming equal affinity to endogenous or transgene sequences, phosphorimaging these blots suggested that the JP17 rats contained at least 4 copies of cVO14 whereas JP59 rats had a single copy. The copy number and restriction pattern of the transgenes remained consistent through successive generations of breeding, suggestive of a single site of chromosomal integration.

Further analysis of DNA suggested that the insert contained concatamers of cVO14 in JP17 but not in JP59, and that one concatamer pair contained a truncation which removes a fragment of approximately 1 kb between 8 kb and 7 kb 5' of rat AVP. Restriction mapping and sequence analysis of the cosmid ends enabled us to design PCR primers (PL216 (SEQ. ID. No. 10 and PL210 (SEQ. ID. No. 9)) that uniquely identify DNA from JP17 rats bearing this insert, and distinguishes them both from non-transgenic littermates, and from JP59 rats bearing a single copy of this insert.

Establishing Colonies of Transgenic Rats.

The founder JP 17 rat is a male. He sires only single litter of rats at 6 months of age although constantly caged with fertile females. This litter contains both male and female rats bearing the transgene, indicating that the integration has occurred onto an autosomal chromosome. No further litters are sired by male progeny. Litters bred from transgenic JP17 female progeny show an approximate 1:1 ratio of transgenic to non-transgenic rats (46 transgenic versus 54 non-transgenic in the first 100 pups) suggesting that the transgene does not have a detrimental effect on embryonic viability.

The founder of the JP 59 line of rats is female and bred normally (the ratio of transgenic to non-transgenic pups is approximately 1:1 (47 transgenic verses 53 non-transgenic in the first 100 pups). This single copy integrant is also present on an autosomal chromosome since male JP59 rats of this line sire transgenic progeny of both sexes.

EXAMPLE 2

Analysis of Expression of Expected Transgene Products

Human Growth Hormone

The expression of hGH from cVO14 is investigated in both JP59 and JP17 rats. Immunocytochemistry shows expression of hGH protein in hypothalamic magnocellular paraventricular (PVN) and supraoptic nuclei (SON). Human GH immunoreactivity is also transported via axons passing through the internal zone of the median eminence and present in the axon terminals in the posterior pituitary.

In situ hybridisation confirms strong expression of hGH in the PVN and SON of transgenic rats of both JP59 and JP17 lines. hGH transcripts are also detected in other sites of AVP expression in the CNS in JP 17 transgenic rats, such as the medial amygdaloid nucleus and the habenula (Buijs, 1987; Caffe et al., 1987; Urban et al., 1990). Double in situ hybridisation analysis or immunocytochemical analysis confirms that hGH expression is localised in AVP neurones, and not in OT neurones. In independent studies, RT-PCR analysis detects hGH transcripts in hypothalami and pituitaries from both lines, and also detected transcripts in the pancreas and also faintly, in adrenals of JP 17 rats, but not in other tissues tested. These findings are in accordance with previous reports of extrapituitary expression of the endogenous AVP gene in these tissues.

Radioimmunoassay for hGH confirms the presence of significant quantities of hGH in posterior pituitary extracts from both JP59 and JP17 animals, with larger amounts in JP17 line consistent with their higher copy number. Small amounts of hGH immunoreactivity are also found in the pancreas ($0.016 \pm 0.0075$ ng/mg of tissue, n=3) of 20 week old JP 17 male rats, though this represents <0.1% of the amounts of hGH found in the posterior pituitary extracts of the same rats ($168$ ng$\pm 16$ ng/mg, n=5). Thymus, heart, kidney, fat, liver, ovary, uterus, testis, lung, cortex, cerebellum, spleen and adrenals all had undetectable levels of this protein (<0.0004 ng of hGH/mg of tissue).

If the hGH transgene is correctly expressed, then stimuli for increased AVP synthesis and release should increase hypothalamic expression of the hGH transgene and decrease pituitary stores of hGH. Chronic osmotic stimulation has been shown to regulate the expression of the AVP gene (Lightman et al., 1987; Murphy et al., 1990) and cause a release of AVP from the posterior pituitary (Fitzsimmons et al., 1994). The stimulus of salt-loading has previously been used to detect whether the DNA regulatory regions responsible for physiological regulation of the rat AVP gene are present within microinjected constructs (Zeng et al., 1994b; Waller et al., 1996). Groups of non-transgenic or transgenic JP59 or JP17 male rats given 2% NaCl w/v in their drinking water for 72 hours both show a marked increase in hGH expression in PVN and SON. Furthermore, posterior pituitary hGH content fall significantly in such salt-loaded animals in parallel with the fall in AVP content. Samples taken from JP17 rats confirm that hGH is secreted, and can be detected in plasma by RIA ($1.3 \pm 0.09$ ng/ml).

The effects of transgenic expression of hGH to reduce rat GH by feedback have been documented earlier in other transgenic rats (Flavell et al., 1996) Therefore, rat GH content of the pituitaries of JP 17 rats and non-transgenic littermates are measured by RIA. Rat GH is significantly reduced in both the male and female JP 17 transgenics in comparison to the non-transgenic controls at 23, 77 and 140 days of age. At 140 days, the mean pituitary rat GH content of male JP 17 rats is 34.2% of that of the age-matched non-transgenics. The pituitary rat GH content is less affected in the female JP 17 rats (57.4% of the mean rat GH content of the non-transgenics, p<0.02).

The size of the anterior pituitaries also suggests that there is a reduction in their cell number as JP 17 male rats at 140 days have significantly smaller anterior pituitaries than non-transgenic controls ($4.6 \pm 0.1$ mg for JP 17 males versus 8.2±0.5 mg for wild-type rats, p<0.002, n=6). The pituitaries of JP 59 males and females do not show a reduction in rat GH content or size (p>0.55).

Bovine Neurophysin

No bovine OT-NP protein can be detected in posterior pituitary extracts (<10 pg per pituitary) from JP17 rats, using a specific RIA that distinguishes bovine neurophysin from rat neurophysins (Gordon-Weeks, 1987). An RT-PCR assay for bovine OT-NP transcripts is applied to hypothalamic extracts of adult males or of lactating female rats culled within 24 hours of littering, from both lines. The latter animals are chosen since they should show higher levels of endogenous OT expression (Van Tol et al., 1988). PCR is performed on cDNA generated by reverse transcribing RNA from various tissues of both JP 17 and JP 59 lines (hypothalamus, pituitary, pancreas, ovary, heart, lung, muscle, thymus, cerebellum, uterus, testis, spleen, kidney, adrenals, liver, cortex). Additional reactions with primers for β-actin and hGH are also included. The reactions of the rat/bovine OT primers with the cVO14 construct and in vitro transcribed rat/bovine OT RNA both yielded the correct size fragment (767 bp), but no transcripts from the rat/bovine OT transgene are detected in any tissue. We conclude that the rat/bovine OT portion of the cVO14 construct is not detectably expressed in JP 17 or JP 59 transgenic animals.

Figure 5:
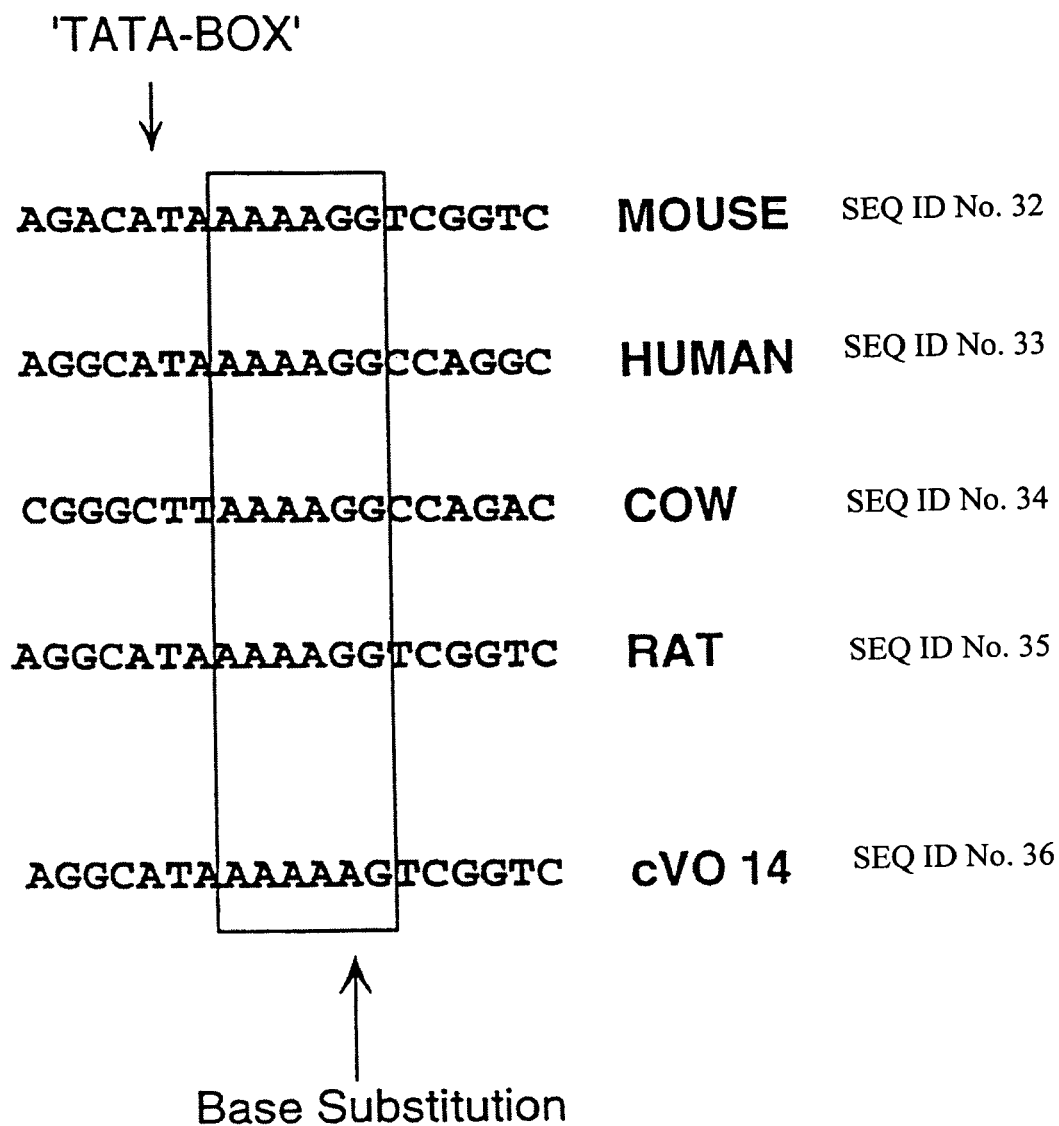
FIG. 5 shows a point mutation in the cVO14 construct in a conserved region 5' to the OT gene. A conserved G residue is substituted with an A residue in the construct. The mouse sequence is SEQ ID NO: 32, the human sequence is SEQ ID NO: 33, the cow sequence is SEQ ID NO: 34, the rat sequence is SEQ ID NO: 35, and the cVO14 sequence is SEQ ID NO: 36.
Figure 7:
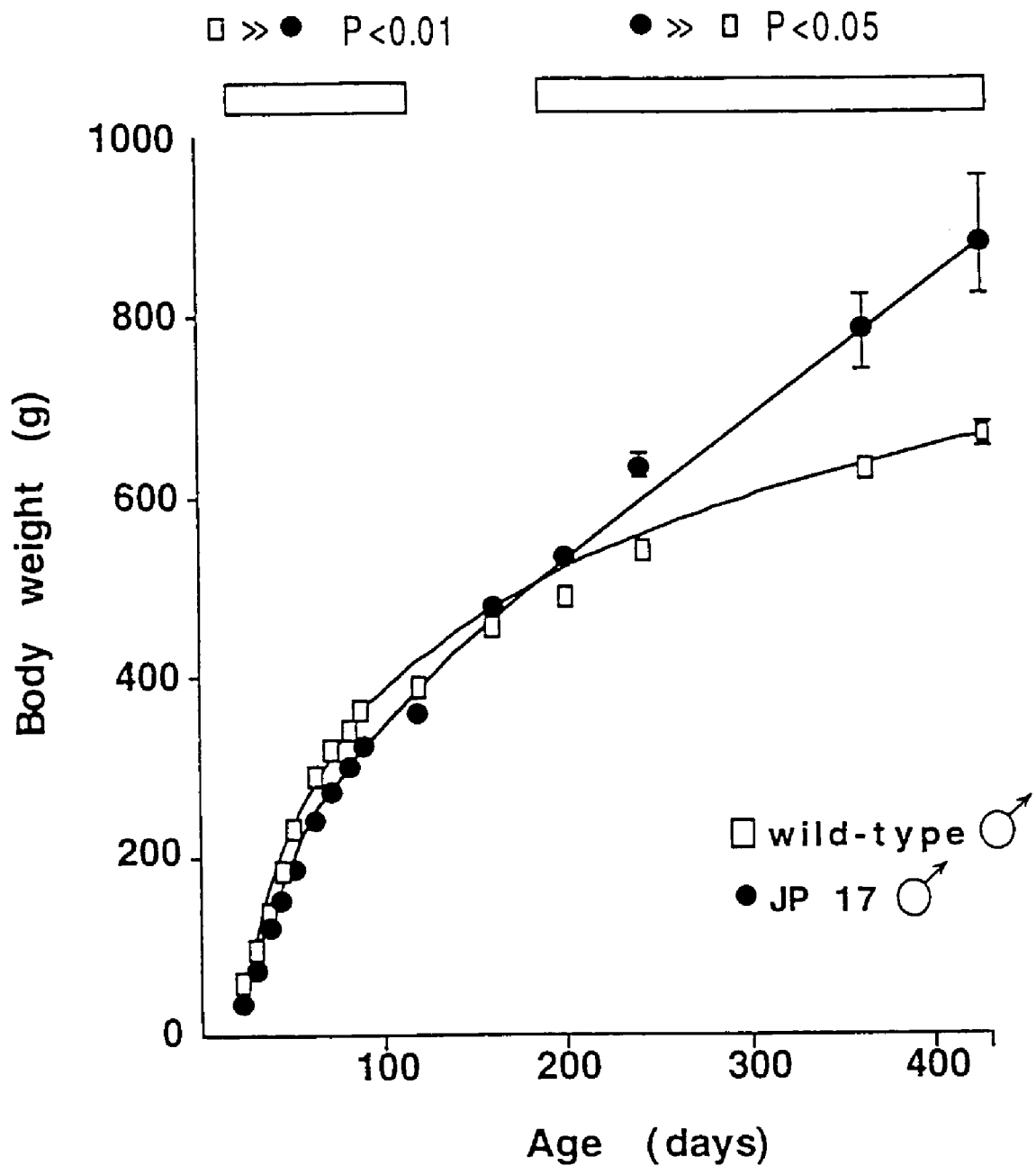
FIG. 7 is a comparison of the body weights of transgenic and non ansgenic rats.

The lack of expression of the rat/bovine OT transgene may indicate that additional sequences lacking from cVO14 are required to achieve appropriate OT expression in addition to expression from the AVP locus. Other possibilities are that alterations introduced into the OT locus prevent expression. This could be in the coding regions of the hybrid rat/bovine OT cassette. Another possibility is the introduction of the Sal I linker 5' of the OT gene. A further possibility is the presence of a base change in the region immediately 3' of the TATA-box which is discovered upon sequencing this region of cVO14 (FIG. 5).

EXAMPLE 3

Discovery and Analysis of 5'OT-EST and 5'OT-EST-XDEL cVO14 is noted to contain a CpG island 13 kB upstream of OT. Sequencing of 3.3 kB of this region of the cosmid reveals a potential novel gene. Comparison with EST sequences in the public databases revealed partial matches to sequences from rat, human and mouse origin. The GenBank accession numbers for such ESTs include: H31114; H31115; AA955566; AA850004; AA104183; AA080247; AA245389; AA242211; AA421310; AA505752; AA421393. Such searches also reveal a partial match to a human genomic sequence GenBank Accession number AF036329. From comparisons with these sequences and the rat genomic DNA sequence disclosed herein, it is predicted that the novel rat gene in cVO14 contains four open reading frames, termed w, x, y, z. This gene is termed 5'OT-EST. The genomic DNA sequence and predicted exon structure is disclosed in SEQ. ID. No. 16. The gene predicts an open reading frame (SEQ. ID. No. 1) and a protein of 200 amino acids, termed 5'OT-EST, whose structure is disclosed in SEQ. ID. No. 2. Comparisons with EST sequences from human and mouse sources and alignment with full length sequences from rat DNA enable the prediction of homologous cDNA and protein sequences in these species and these are disclosed in SEQ. ID. No. 3 and 4 and SEQ. ID. No. 5 and 6 respectively. The protein sequences predicted from these predicted cDNAs are highly homologous, as shown in FIG. 6.

A Not I restriction site is identified approximately 13 kB upstream of OT in cVO3. As described in Appendix 2, this site is deliberately destroyed during the construction and assembly of cVO14 in the pWE15 cosmid vector, as the construct required Not I sites only at the ends of the insert. However, sequence analysis of cVO14 reveals that the Not-1 site lies in 5'OT-EST, more precisely, in exon w of 5'OT-EST. Furthermore, this sequence analysis reveals that in addition to destroying the Not I site, the procedure used (digestion, filling in and religation) also resulted in an additional unpredicted deletion of 412 bp. This deletion includes all of the sequences recognised as exon x as defined herein. The mutated form of this gene, lacking sequences including those for exon x, is therefore termed herein 5'OT-EST-xdel for the purposes of this application. Its sequence, and the structures of the predicted exons from this form of the gene are disclosed in SEQ. ID. Nos. 7 and 8. The presence of 5'OT-EST-xdel in the genome of JP 17 and JP59 rats is confirmed by the generation of the predicted shorter product upon amplification of genomic DNA from these animals by PCR with primers PL266 (5'TCATGT-TGCGGGCTTTGAAC) and PL271 (5'TCTTTCAGTTG-CACCCAAGC) which flank the deletion (see SEQ. ID. Nos. 11 and 12 respectively).

The form of 5'OT-EST that is incorporated in both JP17 and JP59 in 4 or 1 copies, respectively, is mutated from the wild type sequence. 5'OT-EST-xdel would be predicted to give rise to an altered mRNA, which if translated would produce a truncated protein product with an additional novel amino acid sequence. The predicted sequence of this novel product, termed herein 5'OT-EST-xdel is disclosed in SEQ. ID. No. 8. Comparison with the aligned predicted protein sequences of 5'OT-EST in normal rats and in other species predicts that the protein translated from this RNA would contain an altered exon w, with a novel C-terminal peptide sequence (shown in lower case beginning at the arrow in FIG. 6) predicted to arise by translation of DNA sequences normally present as part of an intron in 5'OT-EST. Searches in the protein databases in the public domain do not find any significant matches of this mutated protein sequence to known sequences.

To demonstrate that both the endogenous and truncated forms of 5'OT-EST are transcribed in JP59 and JP17 rats, PCR primers are designed which can distinguish between these gene products. The sequence of these primers is given in SEQ. ID. No. 11, 12 and 13. RT-PCR using these primers confirms the presence of transcripts from the endogenous form of 5'OT-EST in testicular RNA extracts from JP 17, JP59 and wild-type rats, but the presence of a transcript with the 412 bp deletion only in such tissue extracts from JP17 and JP59 rats. Sequencing of amplification products generated by PCR with primers PL266 (SEQ. ID. No. 11) and PL273 (SEQ. ID. No. 13) from wild type and JP17 rats confirms this region of the sequence of the endogenous rat transcript as well as the truncated 5'OT-EST-xdel sequence disclosed in SEQ. ID. No. 8. Extracts of a rat adrenal medullary cell line (PC12 cells) also contain an RNA product of 5'OT-EST of the expected size.

Identification and sequencing of 5'OT-EST and 5'OT-EST-xdel enables the design of probes to carry out in situ hybridisation and RNAse protection analysis for the products of these genes on normal and JP17 rat tissue extracts. In situ hybridisation with probes complementary to exons w or z (more specifically, corresponding to bases 1020–1167 and 2229–2451 of FIG. 4.1 respectively) on hypothalamic sections from wild-type or transgenic animals, revealed a highly specific expression in magnocellular SON and PVN. No other specific expression in different brain regions is observed at this level of detection. This is an unexpected finding, which is repeatedly confirmed. 5'OT-EST is a novel member of the AVP/OT locus and is expressed in the same hypothalamic magnocellular neurones. Similar patterns of expression are seen with both probes and no differences in tissue distribution of hybridisation signal are seen between wild-type or JP17 tissues. Further in situ hybridisation analysis on a wide variety of tissues reveals strong expression in the testis consistent in distribution with tubular or Sertoli cell expression. Sparse expression is also seen in other tissues, including lung, spleen, intestinal smooth muscle and adrenal gland.

From the sequence information, it is further possible to design probes for in situ hybridisation analysis that distinguish completely between the forms of mRNA produced from 5'OT-EST and 5'OT-EST-xdel. More specifically, oligonucleotide probes directed against transcripts containing exon x would be predicted to detect 5'OT-EST but not 5'OT-EST-xdel transcripts, whilst probes directed against the intron sequence in 5'OT-EST that immediately follows the truncation in 5'OT-EST-xdel detect transcripts containing this sequence, that code for the truncated product in extracts from rats expressing 5'OT-EST-xdel transcripts (such as JP17 and JP59 rats) but not from non-transgenic rats. Examples of such probes are given in SEQ. ID. Nos. 14 and 15.

An oligonucleotide probe of the sequence depicted in SEQ. ID. No. 15 (specific for the truncated sequence) is used for in situ hybridization and confirms transgene expression specifically in PVN and SON in JP17 rats, whereas no signal is observed in PVN or SON sections from non-transgenic rats, hybridized at the same time with this probe.

Nuclease protection analysis may also be performed using a riboprobe to exon w described above. From the sequence we disclose herein, this probe would be predicted to protect 147 bp and 94 bp bands from transcripts from 5'OT-EST and 5'OT-EST-xdel respectively. Using such a probe to analyse testicular RNA extracts confirmed that the full length transcript is present in both transgenic and non-transgenic animals and that the truncated product is present in JP17 and JP59 extracts in a level consistent with the copy number of the cVO14 insertion, that the truncated transcript is indeed absent from non-transgenic testis extracts. The full length product is present in control extracts of PC12 cells.

The gene termed 5'OT-EST-xdel present in cVO14 in both JP59 and JP17 rats is transcribed in several tissues in JP17 rats, specifically in hypothalamic cells and in testicular cells, and that the sequence of the truncated transcripts if translated, would give rise to a protein product that is severely truncated with respect to the normal gene product and would an contain additional novel peptide sequence.

EXAMPLE 4

Phenotypic Analysis of JP17 Transgenic (Slob) Rats

Growth Measurements

JP 17 transgenic rats of both sexes and non-transgenic littermates are weighed at regular intervals. Male JP 17 rats show a slight but significant reduction in their body weight up to 120 days of age (p<0.01). This juvenile growth retardation is not seen in females of this line or the rats of either sex of the JP 59 line whose body weights are not significantly different to those of the non-transgenic groups (p>0.7). This effect disappears with time. At 140 days, the weight difference between JP 17 and non-transgenic male rats is no longer significant. Some organs of 140 day old rats are dissected and weighed. Heart weights do not differ significantly (p<0.14) but the weights of the kidneys (0.99±0.03 g in JP 17 rats versus 1.24±0.05 g in non-transgenic rats, p<0.001), liver (11.11±0.29 g in JP 17 rats versus 14.40±0.32 g in non-transgenic rats, p<0.001) and spleen (0.66±0.02 g in JP 17 rats versus 0.84±0.03 g in non-transgenic rats, p<0.001) differs in weight (n=6 in all groups). Disproportionate growth is well known in transgenic animals expressing hGH (e.g. Shea et al., 1987).

Body Weight Measurements in Ageing JP 17 Rats.

Figure 8:
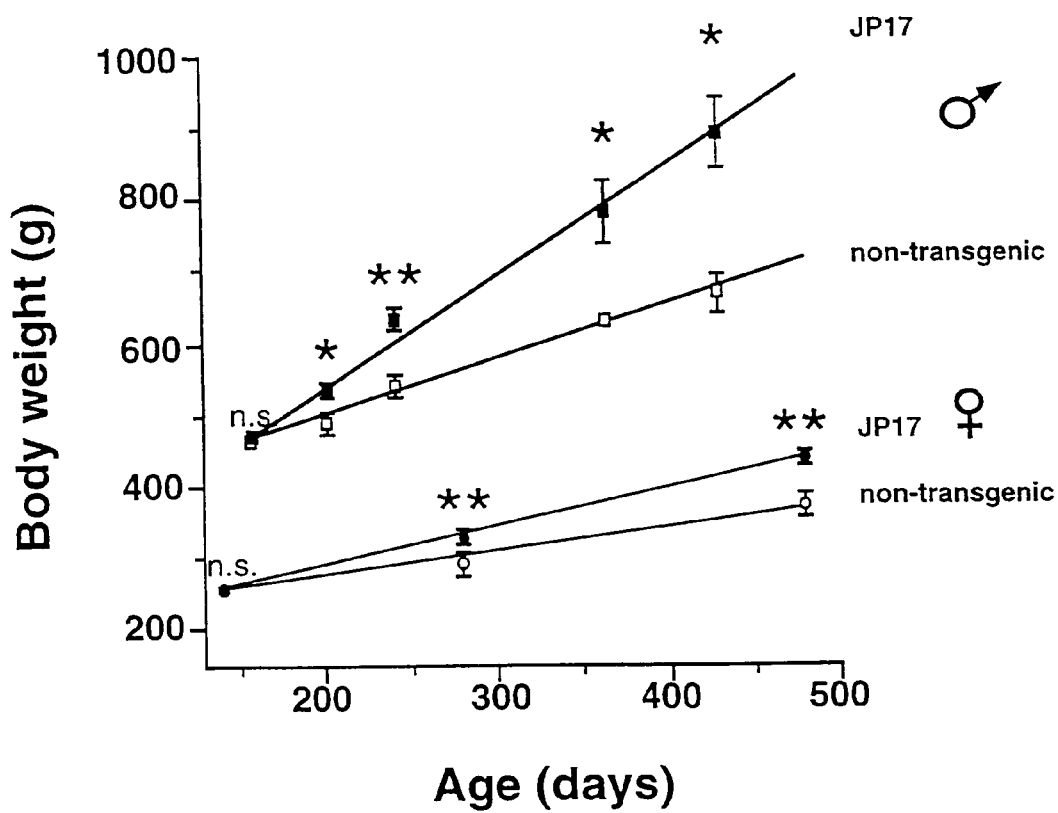
FIG. 8 is a comparison of the body weights of transgenic and non-transgenic male and femnale rats.

After about 140 days, the group of JP 17 transgenic male rats gain weight more rapidly than their non-transgenic littermates ($\Delta$_weight between 200 and 420 days 356.5±57.419 g for JP 17 males versus 182.50±7.554 for non-transgenic males, p<0.03, n=5, FIG. 5.1). Female JP 17 transgenic rats show only a slight increase in weight gain when compared to non-transgenic littermates (A weight between 280 and 480 days 111.8±8.2 g for JP 17 females versus 88±5.1 g for non-transgenic females, p<0.04, n=6). This is illustrated in FIG. 8, which clearly shows the sexually dimorphic weight gains in these animals. No significant increased weight gain is observed in either sex of transgenic JP 59 rats compared with non-transgenic JP59 rats. At one year, the weights of the kidneys and liver of JP 17 male rats have reached a value that is not significantly different than that of the non-transgenic rats (n=6 in both groups) (p<0.08 for kidneys and livers), but the spleens remain lighter (1.03±0.04 g versus 1.225±0.05 g in wild-type rats, p<0.01). These organs in transgenic JP 59 rats show no variation from their non-transgenic littermate controls (p>0.43).

Body Length, Width and Fat-Pad Measurements.

Figure 9:
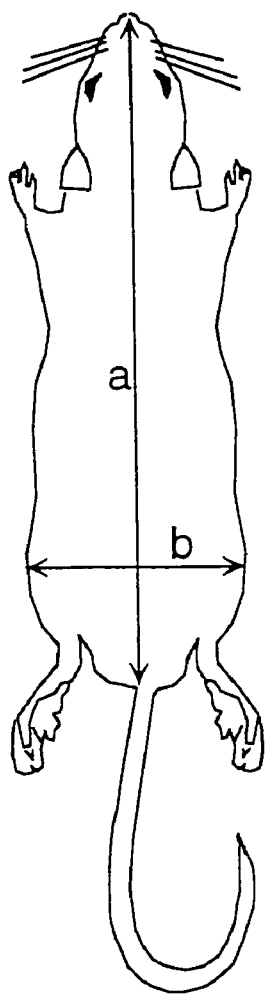
FIG. 9 is a comparison of the measurements (in mm) of the pelvis (b) and of the body length (a) of 20 and 52 week male transgenic and non-transgenic rats (mean+/−sem, ***=p<0.001, n=6–7 per group).
Figure 10:
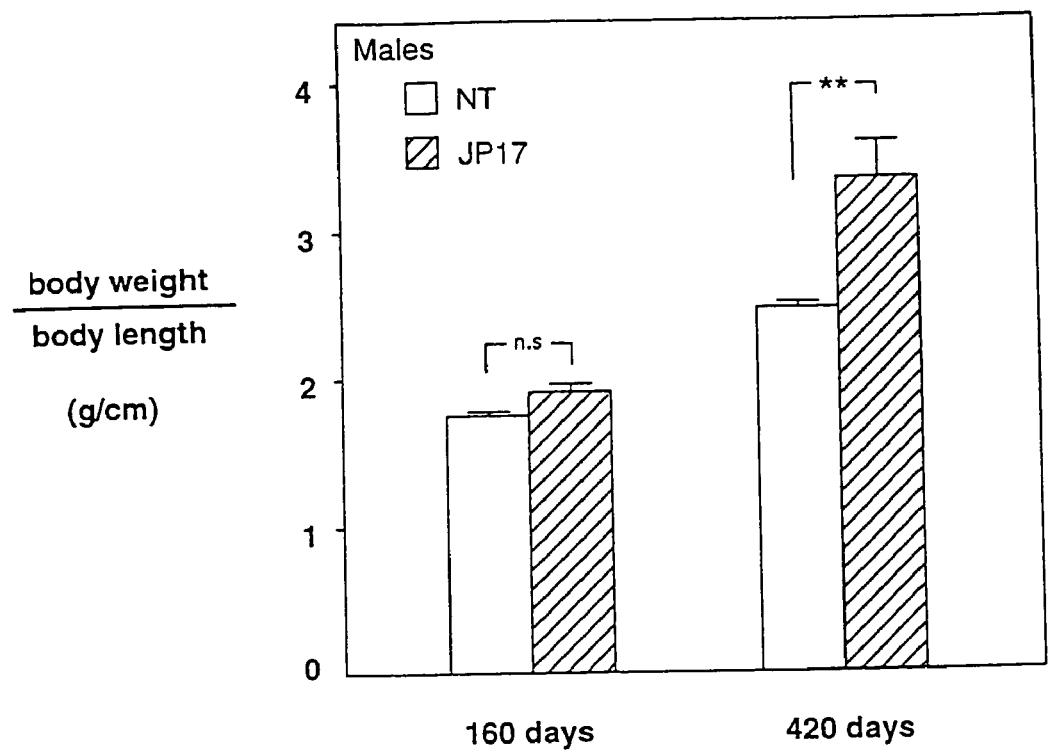
FIG. 10 illustrates the increased body weight/body length ratio of transgenic rats compared with non-transgenic rats.

Measurements of the body lengths (nose-anus) and the width across the pelvic area of anaesthetised male JP17 and non-transgenic rats are taken (FIG. 9). At 20 weeks of age male JP 17 transgenic rats are shorter than their littermate non-transgenic controls with an increased width across the pelvic area. At 52 weeks, the difference in nose-anus length is no longer significant but the girth of the transgenic JP17 rats has increased greatly whereas the non-transgenic rats only exhibit a moderate increase in girth. This late-onset increase in the body weight/length ratio is shown in FIG. 10.

Figure 11:
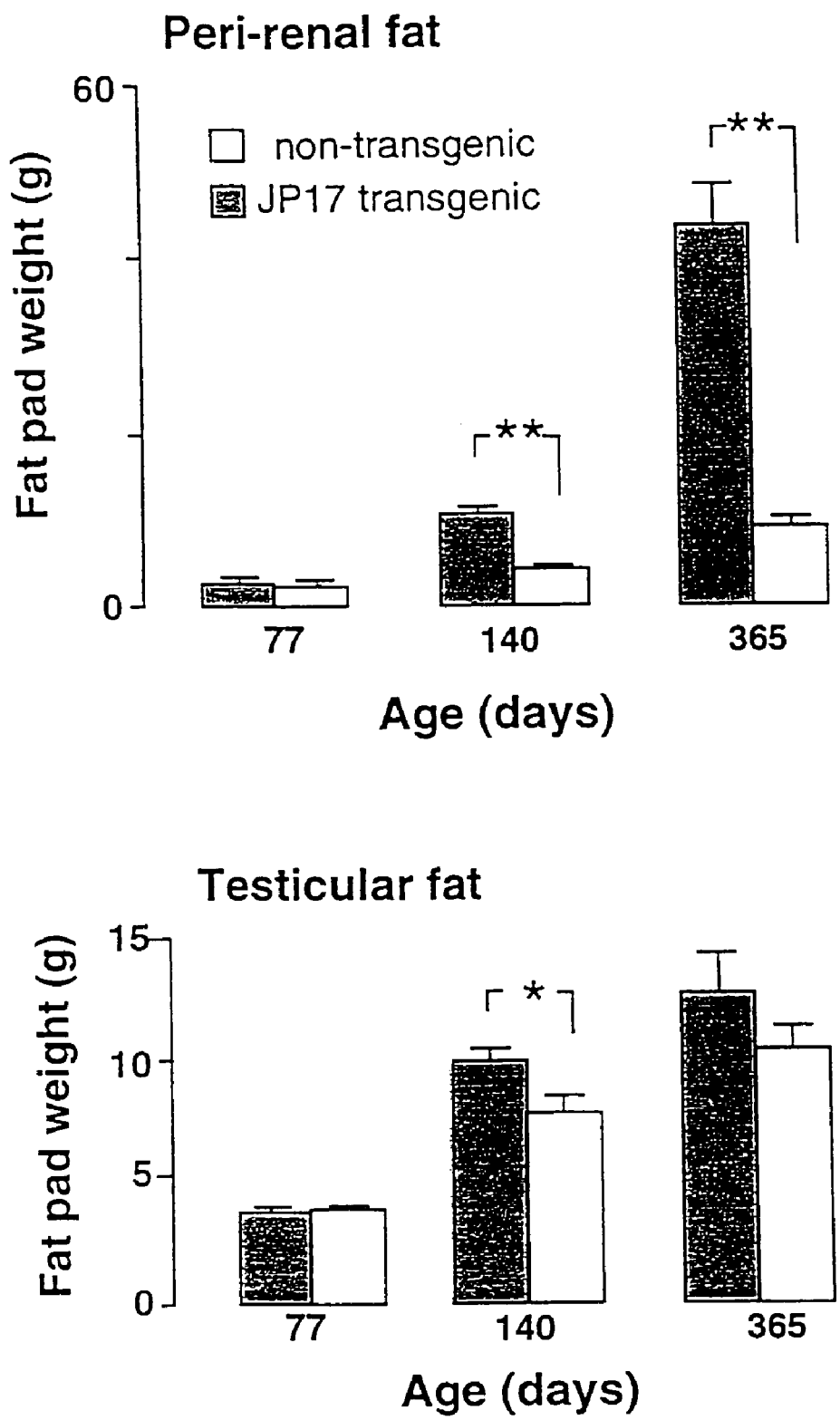
FIG. 11 shows the weights of the peri-renal and testicular fat pads in JP17 male transgenic and non-transgenic animals at different ages. (*=p<0.05; **=p<0.01, n=6–7 per group).

A comparison of the body proportions of a live SLOB rats and non-transgenic littermates shows a marked increase in abdominal fat. This is also obvious when individual peri-renal fat pads are compared. To evaluate this abdominal distribution of extra fat in SLOB rats, peri-renal and testicular fat pads are dissected and weighed from matched groups of male JP 17 and non-transgenic littermates of 77, 140 and 365 days of age, and the results are shown in FIG. 11. The peri-renal fat pads of the transgenic rats are markedly increased in weight at both 140 days and 365 days when their mean weight is almost five times that of the non-transgenic animals. The testicular fat, however, did not show a comparable increase. Although testicular fat pad weights are marginally larger than those of the non-transgenic rats at 140 days (p<0.05), no further significant increase occurs during the period of a large accretion in peri-renal fat, and there is no difference in testicular fat pad weights at 365 days between SLOB rats and their non-transgenic littermates, despite their much larger body weight, and evident gross visceral obesity.

In other matched groups of 1 year old SLOB rats and non-transgenic littermates of both sexes, plasma cholesterol, triglycerides, glucose, insulin, leptin and corticosterone are measured in blood samples taken when the animals are killed, and the results are summarised in FIG. 12. Plasma triglycerides are modestly but significantly elevated in SLOB males compared to non-transgenic males. There are no differences in plasma triglycerides in females. Cholesterol levels are no different between the groups. Plasma glucose and insulin values are also in the normal range and did not differ between the groups, suggesting that the obesity is not secondary to diabetes or insulin resistance. Plasma corticosterone is also in the normal range in all groups of rats. Notably however, the plasma leptin levels are elevated significantly in both male and female SLOB rats compared with their non-transgenic littermates, and are almost two-fold higher in SLOB males than in SLOB females. Leptin receptor transcript isoforms are also expressed in normal amounts in the hypothalamus, piriform cortex and choroid plexus. These increases would be expected given their increased body fat, but prompted a study of their food intake.

A further group of 5, 11-month old SLOB rats and 5 non-transgenic rats are housed singly in metabolic cages for 14 days, and after a period of acclimatisation to single housing, food intake is measured over the last four days of the experiment. There is no significant difference in food consumption between the two groups (SLOB rats 23.4±1.1 μg/day vs. 23.5±1.8 g/day in the non-transgenic males, Mean±S.D.).

Although the SLOB phenotype, as demonstrated by the forgoing, has a striking late-onset feature, the phenotype is latent at a younger age and can be induced by increasing the levels of fat in the diet. This is demonstrated by observing the phenotypic differences resulting from feeding two groups of 100 day old transgenic and normal littermates either regular rat chow, which has a fat content of 4%, or a high fat diet having a fat content of 30% over a 27 day period.

Figure 13:
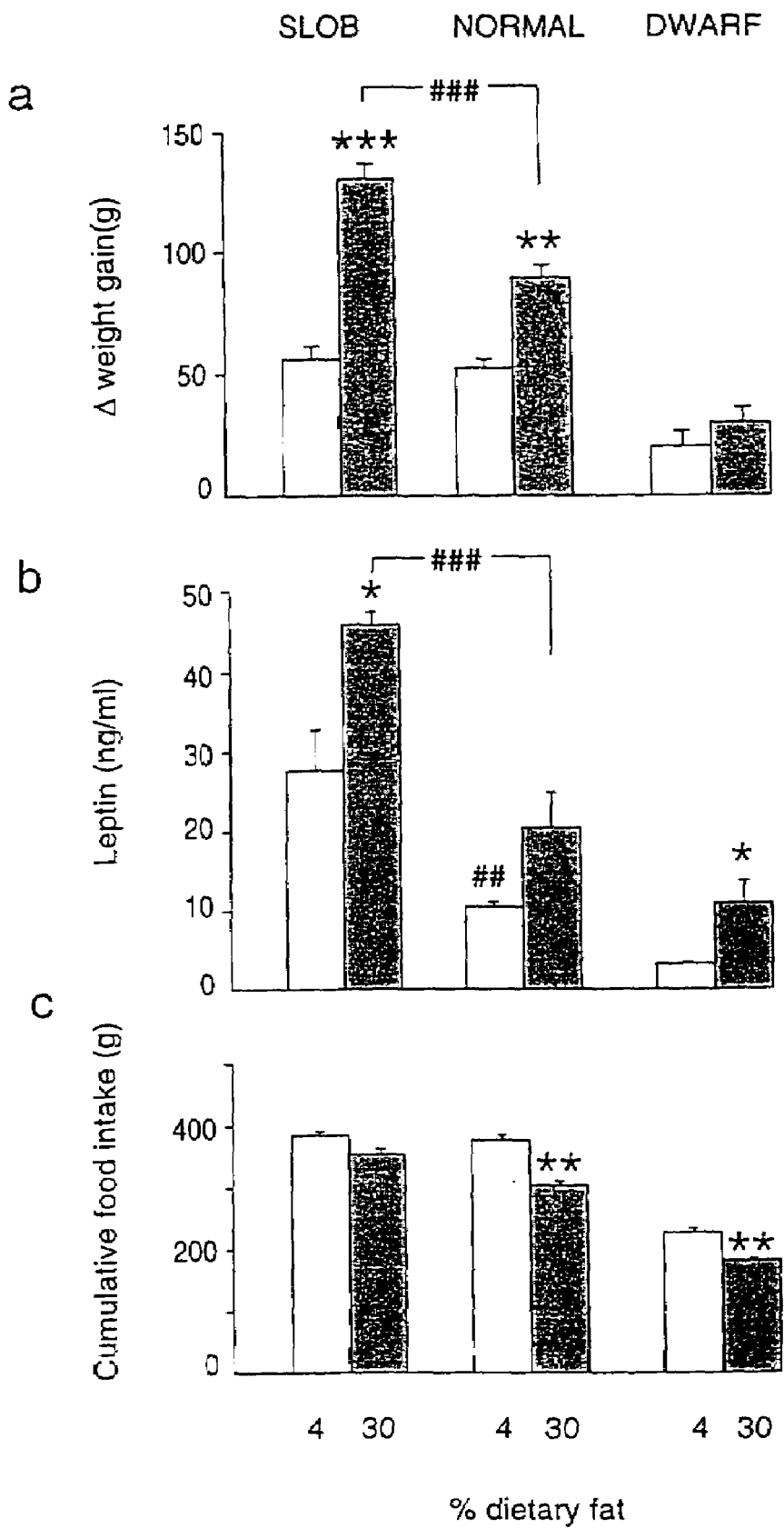
FIG. 13 shows the changes in body weight, leptin levels and food intake associated with young (100 day old) rats fed on normal fat (4%) or high fat (30%) diets. Results are shown for SLOB, non-transgenic and dwarf rats, fed either 4% fat diet (clear bars) or a 30% fat diet (stippled bars) over a 27-day period (*=p<0.05; =p<0.01; *=p<0.001, high vs. low fat diet: ##=p<0.01; ###=p<0.001, SLOB vs. nontrnasgenic rats).

The rats fed a normal diet show no significant difference in weight gain between transgenic and non-transgenic littermates. However, in the case of the rats fed on a 30% fat diet, the transgenic animals gain twice the weight of their non-transgenic littermates (see FIG. 13). Controls in dwarf rats show that the obese phenotype is not due to growth hormone deficiency.

Plasma leptin levels are measured at sacrifice. These are found to be higher in transgenic animals, and rise in both transgenic and non-transgenic rats fed on a 30% fat diet. Moreover, the increase in dietary fat is associated with a significantly reduced food intake in normal rats, but not in SLOB rats, despite their higher leptin levels.

Induction of Obesity in Ovariectomised Female Rats.

Figure 14:
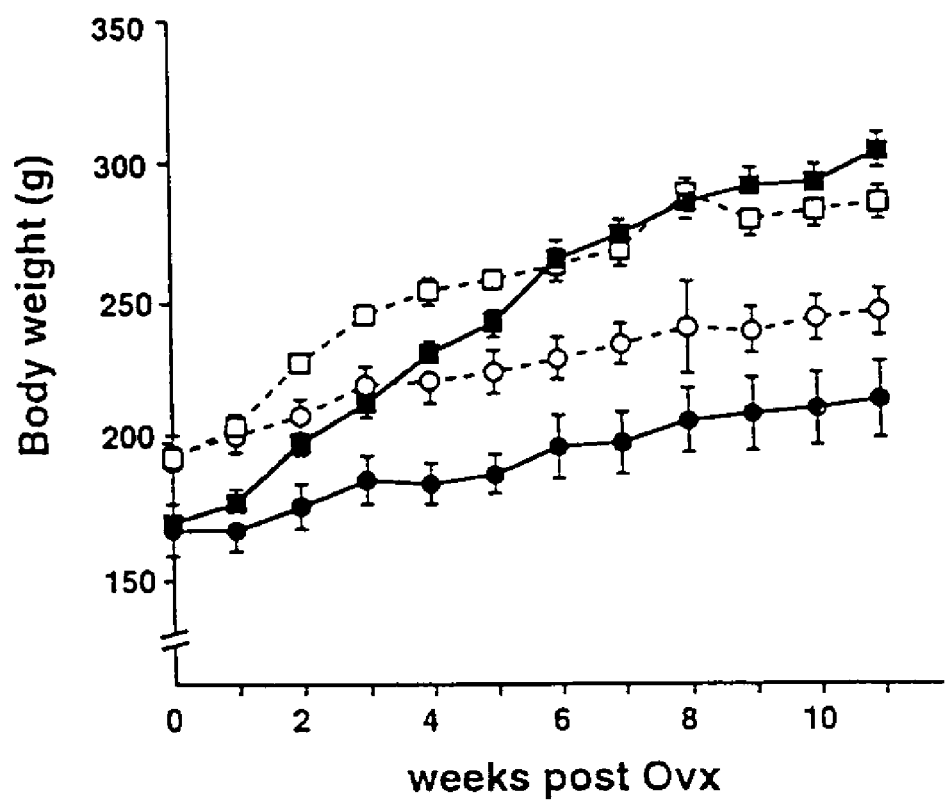
FIG. 14 shows the changes in body weight associated with ovariectomy in transgenic rats and non-transgenic littermates. ⊢-ovariectomised SLOB rat; _-ovariectomised wild-type rat; ●-sham ovariectomised SLOB rat; o-sham ovariectomised wild-type rat.

Four groups of female rats are studied (see FIG. 14). Sham-operated transgenic female SLOB rats are lighter than non-transgenic sham-operated female littermates at 100 days, but gain the same amount of weight in the following 11 week period (Δwt 45.5±5.3 g, vs Δwt 48.4±3.8 g). In rats ovariectomised under anaesthesia, both groups show an increase in weight gain; this increase is much higher in SLOB rats than in non-transgenic littermates (Δwt 128±7.7 g vs 89±4.3 g, P<0.001). Some animals from each group are killed 18 weeks post ovariectomy and their supra-renal fat pads dissected and weighed. The fat pad weight is much larger after ovariectomy in SLOB rats (4.67±0.61 vs 1.37±0.39 g in ovariectomised versus sham-ovariectomised SLOB females, P<0.01), than in nontransgenic rats (2.33±0.94 g vs 1.0±0.01 g in ovariectomised vs sham-ovariectomised nontransgenic littermates).

Fertility of the JP 17 Male Rats.

Twelve JP 17 and twelve non-transgenic young adult males are each housed with two 12-week old normal females, for several consecutive days. The female rats are examined every morning for evidence of copulation, either in the form of a vaginal plug or sperm in vaginal smears, and are observed for a sufficient amount of time to allow any litters conceived during this time to be born. No litters are sired in this time by JP 17 males, whereas 11 of the 12 females housed with wild-type males produced litters.

The immediate cause of infertility in male SLOB rats is unknown. The size and gross anatomy of their testes and seminal vesicles is normal, suggesting unaffected levels of gonadotrophins or androgens. Testicular size, sperm morphology, motility and testosterone levels all appear normal in SLOB rats. Treatment of a SLOB male rat with exogenous androgens did not improve fertility. One cause could be hGH, since infertility is a common problem in GH transgenic animals (Yun et al., 1987, Bartke et al., 1988, Flavell et al., 1996) and male transgenic animals expressing hGH have been reported to have a reduced frequency in the impregnation of females (Bartke et al., 1992). However female SLOB rats also express equivalent amounts of hGH and are not infertile. Furthermore, we found no evidence for hGH expression or of hGH protein in testes from SLOB rats.

In contrast, the expression of 5'OT-EST in normal rats and the high level of a truncated RNA product from 5'OT-EST-xdel in hypothalamus and in particular, the testis from SLOB male rats, and the lack of expression of either product in ovaries in SLOB females, leads us to conclude that the novel infertility and obesity phenotype more probably results from the presence of multiple copies of 5'OT-EST-xdel in SLOB rats. A disruption of testicular function by 5'OT-EST-xdel and consequent infertility is part of, may partly contribute to, or exacerbate the degree of the male-preponderance of, the obesity phenotype of SLOB rats. A testicular disruption is not absolutely required however, since a mild visceral obesity can also be discerned in SLOB females.

Longevity of SLOB Male Rats.

The longevity of JP 17 also appears to differ to that of normal rats. Six male JP 17 rats and six wild-type rats are housed under constant conditions. After two years, all six JP 17 rats have died, five at between 10 and 14 months of age and the sixth at 21 months of age, whereas only a single wild-type rat has died at 13 months. The longevity of JP 17 females or JP 59 males or females has not been similarly investigated.

Comparison of Phenotype with Other Rat Obesity Models

When comparing the phenotype in SLOB rats with other findings reported in the literature, the closest parallels are lines of transgenic rats expressing hGH driven by a mouse whey acidic protein promoter, (Ninomiya et al., 1994; Ikedae et al., 1994, 1995, 1997). Ikeda et al. (1995) described two lines of rats expressing high or low hGH levels in serum. Gigantism is observed in the high hGH-expressing line, but visceral obesity is also observed in the low-expressing line, associated with endogenous GH suppression. No sexual dimorphism is reported, and the obesity is associated with carbohydrate metabolic disorders, hypertriglyceridaemia and insulin resistance. Ikeda et al. 1995 specifically concluded that the effect is due to differences in serum hGH levels affecting carbohydrate metabolism. A later study in these rats (Ikeda et al. 1997) reported female infertility and enlarged ovaries which further distinguishes this phenotype from that seen in SLOB rats.

In common with the rats reported by Ikeda et al. (1994), SLOB rats also show reduced rat GH production and secretion. GH deficiency is associated with increased visceral fat in humans, but this can be alleviated by hGH treatment. However, isolated rat GH deficiency is an unlikely cause of obesity in SLOB rats as other lines of severely GH deficient dwarf rats (Charlton et al., 1988) do not develop obesity when housed under identical conditions to SLOB rats. Obesity can be induced in such dwarf rats (as in normal rats), when placed on high fat diets for prolonged periods though females are more susceptible than males (Clark et al., 1996). A similar pituitary GH suppression is also evident in female SLOB rats but they do not develop the same massive abdominal obesity as males. Pituitary rat GH suppression is also seen in the non-obese JP59 rats of both sexes and in Tgr rats (Flavell et al., 1996) which do not develop obesity.

The defects in other genetic models of obesity in the rat have recently clarified; examples of these include the Zucker fa/fa rat, the Koletsky (f) obese rat, the JLA/cp corpulent rat, and the OLETF rat, and their related sub strains (Iida et al., 1996; Wu-peng et al., 1997; Takaya et al., 1996; Lee et al., 1997; Kahle et al., 1997; None of these show the male specificity, late onset or pattern of distribution of obesity seen in SLOB rats and they exhibit significant hyperglycaemia and insulin resistance, which again distinguishes them from SLOB rats. Male specificity, infertility, extremely late onset of obesity, a highly selective visceral accumulation of fat, but relatively normal metabolic profile, without insulin resistance, hyperphagia or hyperglycaemia distinguishes the dominant phenotype in the SLOB rats from all other known models of obesity in the rat, including those with low endogenous rat GH expression or hGH expression from other transgenes.

REFERENCES

Al-Shawi R Kinnaird, J., Burke, J., Bishop, J. O. 1990 Expression of a foreign gene in a line of trangenic mice is modulated by a chromosomal position effect. Molecular and Cellular Biology 10: 1192–1198.

Altschul et al. (1994) Nature Genetics 6:119–129.

Ang H-L., Ivell, R., Walther, N., Nicholson, H., Ungefroren, H., Millar, M., Carter, D., Murphy, D. 1994 Over-expression of oxytocin in the testes of a transgenic mouse model. Journal of Endocrinology 140: 53–62.

Ang H-L, Ungefroren, H., De Bree, F., Foo, N. C., Carter, D., Burbach, J. P., Ivell, R., Murphy, D., 1991 Testicular oxytocin gene expression in seminiferous tubules of cattle and transgenic mice. Endocrinology 128: 2110–2117.

Banerjee S A, Roffler-Tarlov, S., Szabo, M., Frohman, L., Chikaraishi, D. M. 1994 DNA regulatory sequences of the rat tyrosine hydroxylase gene direct correct catecholaminergic cell-type specificity of a human growth hormone reporter in the CNS of transgenic mice causing a dwarf phenotype, Molecular Brain Research 24: 89–106.

Bartke, A., Steger, R. W., Hodges, S. L., Parkening, T. A., Collins, T. J., Yun, J. S., Wagner, T. E. 1988 Infertility in transgenic female mice and human growth hormone expression: evidence for luteal failure. Journal of Experimental Zoology 248: 121–124.

Bartke A., Naar, E. M., Johnson, L., May, M. R., Cecim, M., Yun, J. S., Wagner, T. E. 1992 Effects of expression of human or bovine growth hormone genes on sperm production and male reproductive performance in four lines of transgenic mice. Journals of Reproduction and Fertility 95: 109–118.

Bartke A., Cecim, M., Tang, K., Steger, R. W., Chandrashekar, V., Turyn, D. 1995 Neuroendocrine and reproductive consequences of overexpression of growth hormone in transgenic mice. Proceedings of the Society for Experimental Biology and Medicine 206: 345-359.

Belenky M., Castel, M., Young III, W. S., Gainer, H., Cohen, S. 1992 Ultrastructural immunolocalization of rat oxytocin-neurophysin in transgenic mice expressing the rat oxytocin gene. Brain Research 583: 279–286.

Bennett P A, Levy, A., Sophokleous, S., Robinson, I. C. A. F., Lightman, S. L. 1995 Hypothalamic GH receptor gene expression in the rat: effects of altered GH status. Journal Endocrinology 147: 225–234.

Birnboim H C, Doly, J. 1979 A rapid alkaline extraction procedure for screening recombinant plasmid DNA. Nucleic Acid Research 7: 1513–1523.

Bonifer C Vidal, M., Grosveld, F., Sippel, A. E. 1990 Tissue-specific and position independent expression of the complete gene domain for chicken lysozyme in transgenic mice. The European Molecular Biology Organisation Journal 9: 2843–2848.

Boss, O.; Samec, S.; Paoloni-Giacobino, A.; Rossier, C.; Dulloo, A.; Seydoux, J.; Muzzin, P.; Giacobino, J.-P.: Uncoupling protein-3: a new member of the mitochondrial carrier family with tissue-specific expression. FEBS Lett. 408: 39–42, 1997.

Bourne J A 1984 Handbook of Immunoperoxidase Staining Methods, DAKO corporation, Santa Barbara, USA.

Bray G A York, D. A. 1979 Hypothalamic and genetic obesity in experimental animals: an autonomic and endocrine hypothesis. Physiological Reviews 59: 719–809.

Brem G Wanke, R., Wolf, E., Buchmuller, T., Muller, M., Brenig, B., Hermanns, W. 1989 multiple consequences of human growth hormone expression in transgenic mice. Molecular and Biological Medicine 6: 531–547.

Bucchini D Ripoche, M.-A., Stinnakre, M.-G., P. Desbois., Lores, P., Monthioux, E., Absil, J., Lepesant, J.-A., Pictet, R., Jami, J. 1986 Pancreatic expression of the human insulin gene in transgenic mice. Proceedings of the National Academy of Science USA 83: 2511–2515.

Buijs $\mu$M 1987 Vasopressin localization and putative functions in the brain. In: Vasopressin priniciples and properties; D. M. Gash and G. J. Boer (eds). 91–115.

Caffe A R van Leeuwen, F. W., Luiten, P. G. M. 1987 Vasopressin cells in the medial amygdala of the rat project to the lateral septum and ventral hippocampus. The Journal of Comparative Neurology. 261: 237–252.

Cecim M Fadden, C., Kerr, J., Steger, R. W., Bartke, A. 1995 Infertility in transgenic mice overexpressing the bovine growth hormone gene: disruption of the neuroendocrine control of prolactin secretion during pregnancy. Biology of Reproduction 52: 1187–1192.

Chandrashekar V Bartke, A., Wagner, T. E. 1991 Interactions of human growth hormone and prolactin on pituitary and Leydig cell function in adult transgenic mice expressing the human growth hormone gene. Biology of Reproduction 44: 135–140.

Charlton H M Clark, R. G., Robinson, I. C. A. F., Porter Goff, A. E., Cox, B. S., Bugnon, C., Bloch, B. A. 1988 Growth hormone-deficient dwarfism in the rat: a new mutation. Journal of Endocrinology 119: 51–58.

Chen, H., O. Charlat, L. A. Tartaglia, E. A. Woolf, X. Weng, S. J. Ellis, N. D. Lakey, J. Culpepper, K. J. Moore, R. E.

Breitbart, G. M. Duyk, R. I. Tepper, and J. P. Morgenstern. 1996. Evidence that the diabetes gene encodes the leptin receptor: identification of a mutation in the leptin receptor gene in db/db mice. Cell. 84:491–495.

Chomczynski P Sacchi, N. 1987 Single-step method of RNA isolation by acid guanidinium thiocyanate-phenol-chloroform extraction. Analytical Biochemistry 162: 156–9.

Clark, R. G., Mortensen, D. L., Carlsson, L. M., Carlsson, B., Carmignac, D., and Robinson, I. C. A F. (1996). The obese growth hormone (GH)-deficient dwarf rat: body fat responses to patterned delivery of GH and insulin-like growth factor-I. Endocrinology 137, 1904–12.

Coleman DL Eicher, E. M. 1990 Fat (fat) and tubby (tub): Two autosomal recessive mutations causing obesity syndromes in the mouse. Journal of Hereditary 81: 424–427.

Comuzzie, A. G. & Allison, D. B. (1998). The search for human obesity genes. Science, 280:1374–1377.

Cool, D. R.; Normant, E.; Shen, F.; Chen, H.-C.; Pannell, L.; Zhang, Y.; Loh, Y. P. 1997: Carboxypeptidase E is a regulated secretory pathway sorting receptor: genetic obliteration leads to endocrine disorders in Cpe(fat) mice. Cell 88: 73–83, De Lecea, L.; Kilduff, T. S.; Peyron, C.; Gao, X.-B.; Foye, P. E.; Danielson, P. E.; Fukuhara, C.; Battenberg, E. L. F.; Gautvik, V. T.; Bartlett, F. S., II; Frankel, W. N.; van den Pol, A. N.; Bloom, F. E.; Gautvik, K. M.; Sutcliffe, J. G. 1998 The hypocretins: hypothalamus-specific peptides with neuroexcitatory activity. Proc. Nat. Acad. Sci. 95: 322–327.

Dillon N Grosveld, F. 1993 Gene transcription—a practical approach. IRL Press at Oxford University Press. B. D. Hames and S. J. Higgins (eds): 153–187. Fairhall KM Carmignac, D. F., Robinson, I. C. A. F. 1992 Growth hormone (GH) binding protein and GH interactions in vivo in the guinea pig. Endocrinology 131: 1963–1969.

Fan, W., Boston, B. A., Kesterson, R. A., Hruby, V. J., and Cone, R. D. (1997). Role of melanocortinergic neurons in feeding and the agouti obesity syndrome. Nature 385, 165–8.

Fitzsimmons M D Roberts, M. M., Robinson, A. G. 1994 Control of the posterior pituitary vasopressin content: Implications for the regulation of the vasopressin gene. Endocrinology 134: 1874–1878.

Flavell D M., Wells, T., Wells, S. E., Carmignac, D. F., Thomas, G. B., Robinson, I. C. A. F. 1996 Dominant dwarfism in transgenic rats by targeting human growth hormone (GH) expression to hypothalamic GH-releasing factor neurons. The European Molecular Biology Organisation Journal 15: 3871–3879.

Foo N C., Funkhouse, J. M., Carter, D., Murphy, D., 1994 A testis specific promoter in the rat vasopressin gene. Journal of Biological Chemistry 269: 659–667.

Fujiwara Y., Miwa, M., Takahashi, R., Hirabayashi, M., Suzuki, T., Ueda, M. 1997 Position-independent and high-level expression of human alpha-lactalbumin in the milk of transgenic rats carrying a 210-kb YAC DNA construct. Molecular Reproduction and development. 47: 157-163.

Gainer H. & Wray, S. 1994 Cellular and molecular biology of oxytocin and vasopressin. In: The Physiology of Reproduction, E. Knobil and J. D. Neill (eds): 1099–112.

Good D J., Porter, F. D., Mahon, K. A., Parlow, A. F., Weatphal, H., Kirsch, I. R. 1997 Hypogonadism and obesity in mice with a targeted deletion of the NhIh2 gene. Nature Genetics 15: 397–401.

Gordon-Weeks, R 1987 PhD thesis. University of London.

Graham, M.; Shutter, J. R.; Sarmiento, U.; Sarosi, I.; Stark, K. L. 1997.: Overexpression of Agrt leads to obesity in transgenic mice. Nature Genet. 17: 273–274, Grant S G., Jessee, J., Bloom, F. R., Hanahan, D. 1990 Differential plasmid rescue from transgenic mouse DNAs into *Escherichia coli* methylation-restriction mutants. Proceedings of the National Academy of Science 87: 4645–4649.

Grant F D., Reventos, J., Gordon, J. W., Kawabata, S., Miller, M., Majzoub, J. A. 1993a Expression of the rat arginine vasopressin gene in transgenic mice. Molecular Endocrinology 7: 659–667.

Grant F D., Reventos, J., Gordon, J. W., Kawabata, S., Miller, M., Majzoub, J. A. 1993b Tissue-specific expression and osmotic regulation of a rat vasopressin gene in transgenic mice. Annals of the New York Academy of Sciences 689: 530–533.

Gray RP & Yudkin, J. S. 1997 Cardiovascular disease in diabetes mellitus. In: Textbook of diabetes, J. Pickup and G. Williams (eds): pp57.1–57.22.

Grosveld F., van Assendelft, G. B., Greaves, D. R., Kollias, G. 1987 Position-independent, high-level expression of human β-globin gene in transgenic mice. Cell 51: 975–985.

Habener J F., Cwikel, B. J, Hermann, H, Hammer, R. E, Palmiter, R. D, Brinster, R. L, 1989 Metallothionein-vasopressin fusion gene expression in transgenic mice. The Journal of Biological chemistry 264: 18844–18852.

Hammer R E., Pursel, V. G., Rexroad, C. E., Wall, R. J., Bolt, D. J., Ebert, K. M., Palmiter, R. D., Brinster, R. L. 1985 Production of transgenic rabbits, sheep and pigs by microinjection. Nature 315: 680–683.

Hanahan D. 1983 Studies on transformation of *Escherichia coli* with plasmids. Journal of Molecular Biology 166: 557–569.

Ho M-Y., Carter, D. A., Ang, H-L., Murphy, D. 1995 Bovine oxytocin transgenes in mice. Journal of Biological Chemistry. 270: 27199–27205.

Hogan B., Constantini, F., Lacy, E. 1986 Manipulating the mouse embryo. Cold Spring Harbor Laboratory Press, Cold Spring Harbor, N.Y.

Hollingshead P G., Martin, L., Pitts, S. L., Stewart, T. A. 1989 A dominant phenocopy of hypopituitarism in transgenic mice resulting from central nervous system synthesis of human growth hormone. Endocrinology 125: 1556–1564.

Horn A M., Robinson, I. C. A. F., Fink, G. 1985 Oxytocin and vasopressin in rat hypophysial portal blood: experimental studies in normal and Brattleboro rats. Journal of Endocrinology 104: 211–224.

Huber M C., Bosch, F. X., Sippel, A. E., Bonifer, C. 1994 Chromosomal position effect in chicken lysozyme gene transgenic mice are correlated with supression of DNase I hypersensitive site formation. Nucleic Acid Research 22: 4195–4201.

Huszar, D., Lynch, C. A., Fairchild, H. V., Dunmore, J. H., Fang, Q., Berkemeier, L. R., Gu, W., Kesterson, R. A., Boston, B. A., Cone, R. D., Smith, F. J., Campfield, L. A., Burn, P., and Lee, F. (1997). Targeted disruption of the melanocortin-4 receptor results in obesity in mice. Cell 88, 131–41.

Iida M., Murakami, T., Ishida, K., Mizuno, A., Kuwajima, M., Shima, K. 1996 Substitution at codon 269 (glutamine-proline) of the leptin receptor (OF—R) cDNA is the only mutation found in the Zucker Fatty (fa/fa) rat. Biochemical and Biophysical Research Communications 224: 597-604.

Ikeda, A. Chang, K., Matsuyama, M., Nishihara, M. & Takahashi, M. 1995 Disorders in carbohydrate metabolism in two lines of transgenic rats expressing different levels of human growth hormone. Proceedings of US Endocrine Society Washington P2–241.

Ikeda, A., Matsumoto, Y., Chang, K. T., Nakano, T., Matsuyama, S., Yamanouchi, K., Ohta, A., Nishihara, M., Tojo, H., Sasaki, F. & Takahashi, M (1997). Different female reproductive phenotypes determined by human growth hormone (hGH) levels in hGH-trasngenic rats. Biol Reprod. 56: 847–851.

Ikeda, A., Matsuyama, S. Nishihara, M., Tojo, H. & Takahashi, M. 1994. Changes in endogenous growth hormone secretion and onset of puberty in transgenic rats expressing human growth hormone gene. Endocr J. 41: 523–529.

Ivell R & Richter, D. 1984 Structure and comparison of the oxytocin and vasopressin genes from rat. Proceedings of the National Academy of Science, USA. 81: 2006–2010.

Jamal, Z., Martin, A., Gomez, M. A., Hales, P., Chang, E., Russell, J. C., and Brindley, D. N. (1997). Phosphatidate phosphohydrolases in liver, heart and adipose tissue of the JCR:LA corpulent rat and the lean genotypes: implications for glycerolipid synthesis and signal transduction. Int J Obes Relat Metab Disord 16, 789–99.

Jones B K., Monks, B. R., Liebhaber, S. A., Cooke, N. E. 1995 The human growth hormone gene is regulated by multicomponent locus control region. Molecular and Cellular Biology 15: 7010-7021.

Kahle, E. B., Butz, K. G., Chua, S. C., Kershaw, E. E., Leibel, R. L., Fenger, T. W., Hansen, C. T., and Michaelis, 0. E. (1997). The rat corpulent (cp) mutation maps to the same interval on (Pgm1-Glut1) rat chromosome 5 as the fatty (fa) mutation. Obes Res 5, 142–5.

Kiyama H & Emson, P. C. 1990 Evidence for the co-expression of oxytocin and vasopressin messenger ribonucleic acids in magnocellular neurosecretory cells: simultaneous demonstration of two neurohypophysin messenger ribonucleic acids by hybridization histochemistry. Journal of Neuroendocrinology 2: 257–259.

Klebig, M. L., Wilkinson, J. E., Geisler, J. G., and Woychik, R. P. (1995). Ectopic expression of the agouti gene in transgenic mice causes obesity, features of type II diabetes, and yellow fur. Proc Natl Acad Sci USA 92, 4728–32.

Kleyn, P. W., Fan, W., Kovats, S. G., Lee, J. J., Pulido, J. C., Wu, Y., Berkemeier, L. R., Misumi, D. J., Holmgren, L., Charlat, O., Woolf, E. A., Tayber, O., Brody, T., Shu, P., Hawkins, F., Kennedy, B., Baldini, L., Ebeling, C., Alperin, G. D., Deeds, J., Lakey, N. D., Culpepper, J., Chen, H., Glucksmann, K. M., Moore, K. J., et al (1996). Identification and characterization of the mouse obesity gene tubby: a member of a novel gene family. Cell 85, 281–90.

Kristensen, P.; Judge, M. E.; Thim, L.; Ribel, U.; Christjansen, K. N.; Wulff, B. S.; Clausen, J. T.; Jensen, P. B.; Madsen, 0. D.; Vrang, N.; Larsen, P. J.; Hastrup, S. (1998). Hypothalamic CART is a new anorectic peptide regulated by leptin. Nature 393: 72–76.

Lacy E., Roberts, S., Evans, E. P., Burtenshaw, M. D., Costantini, F. D. 1983 A foreign 13-globin gene in transgenic mice: Integration at abnormal chromosomal positions and expression in inappropriate tissues. Cell 34: 343–358.

Land H, Graz, M, Ruppert, S, Schmale, H, Rehbein, M, Richter, D, Schutz, G, 1983 Deduced amino acid sequence from the bovine oxytocin-neurophysin precursor cDNA. Nature 302: 342-344.

Lee & Costlow 1987. Methods in Enzymology 152:633–648.

Lee, G., Li, C., Montez, J., Halaas, J., Darvishzadeh, J., and Friedman, J. M. (1997). Leptin receptor mutations in 129 db3J/db3J mice and NIH facp/facp rats. Mamm Genome 8, 445–7.

Lightman SL & Young III, W. S. 1987 Vasopressin, oxytocin, dynorphin, enkephalin and corticotrophin-releasing factor mRNA stimulation in the rat. Journal of Physiology 394: 23–39.

Mansour et al., (1989) Nature 336, 348–352.

Mathe, D. (1995). Dyslipidemia and diabetes: animal models. Diabetes Metab 21, 106–11.

McGrane MM, de Vente, J., Yun, J., Bloom, J., Park, E., Wynshaw-Boris, A., Wagner, T., Rottman, F. M., Hanson, R. W. 1988 Tissue-specific expression and dietary regulation of a chimeric phosphoenolpyruvate carboxykinase/bovine growth hormone gene in transgenic mice. Journal of Biological Chemistry 263: 11443–11451.

McNamee, C. J., Kappagoda, C. T., Kunjara, R., and Russell, J. C. (1994). Defective endothelium-dependent relaxation in the JCR:LA-corpulent rat. Circ Res 74, 1126–32.

Michaelis, O. Velasquez, M. T., Abraham, A. A., Servetnick, D. A., Scholfield, D. J., and Hansen, C. T. (1995). Development and characteristics of a new strain of obese hyperinsulinemic and hyperlipidemic Dahl salt-sensitive rat. The Dahl salt-sensitive/N1H-corpulent rat. Am J Hypertension.

Miller M W., Duhl, D. M., Vrieling, H., Cordes, S. P., Ollmann, M. M., Winkes, B. M., Barsh, G. S. 1993 Cloning of the mouse agouti gene predicts a secreted protein ubiquitously expressed in mice carrying the lethal yellow mutations. Genes and Development 7: 454–467.

Millet, L.; Vidal, H.; Andreelli, F.; Larrouy, D.; R10u, J.-P.; Ricquier, D.; Laville, M.; Langin, D. 1997 Increased uncoupling protein-2 and –3 mRNA expression during fasting in obese and lean humans. J. Clin. Invest. 100: 2665–2670.

Mohr E., Schmitz, E., Richter, D. 1988 A single rat genomic DNA fragment encodes both the oxytocin and vasopressin genes separated by 11 kilobases and orientated in opposite transcriptional directions. Biochimie 70: 649–654.

Moon, B. C., and Friedman, J. M. (1997). The molecular basis of the obese mutation in ob2J mice. Genomics 42, 152–6.

Morello D., Moore, G., Salmon, A. M., Yaniv, M., Babinet, C. 1986 Studies on the expression of an H-2K/human growth hormone fusion gene in giant transgenic mice. The European Molecular Biology Organisation Journal 5: 1877–1883.

Mullins J J., Peters, J, Ganten, D, 1990 Fulminant hypertension in transgenic rats harbouring the mouse Ren-2 gene. Nature 344: 541–544.

Murphy D. & Carter, D, 1990 Vasopressin gene expression in the Rodent hypothalamus: Transcriptional and post-transcriptional responses to physiological stimulation. Molecular Endocrinology 1054: 1051–1059.

Murphy D & Ho, M-Y. 1995 Oxytocin transgenic mice. Advances in Experimental Medicine and Biology 395: 67–78.

Naggert, J. K.; Fricker, L. D.; Varlamov, O.; Nishina, P. M.; Rouille, Y.; Steiner, D. F.; Carroll, R. J.; Paigen, B. J.; Leiter, E. H. 1995. Hyperproinsulinaemia in obese fat/fat mice associated with a carboxypeptidase E mutation which reduces enzyme activity. Nature Genet. 10: 135–142.

Ninomiya, T., Hirabayashi, M., Sagara, J. & Yuki, A. 1994 Functions of milk protein gene 5' flanking regions on human growth hormone gene. Mol Reprod Dev 37: 276–283.

North, M. A., Naggert, J. K., Yan, Y., Noben, T. K., and Nishina, P. M. (1997). Molecular characterization of TUB, TULP 1, and TULP2, members of the novel tubby gene family and their possible relation to ocular diseases. Proc Natl Acad Sci USA 94, 3128–33.

Ohki-Hamazaki, H., Watase, K., Yamamoto, K., Ogura, H., Yamano, M., Yamada, K., Maeno, H., Imaki, J., Kikuyama, S., Wada, E., and Wada, K. (1997). Mice lacking bombesin receptor subtype-3 develop metabolic defects and obesity. Nature 390, 165–169.

Ollmann, M. M.; Wilson, B. D.; Yang, Y.-K.; Kerns, J. A.; Chen, Y.; Gantz, I.; Barsh, G. S. 1995 Antagonism of central melanocortin receptors in vitro and in vivo by agouti-related protein. Science 278: 135–138, 1997.

Ornitz D M., Palmiter, R. D., Hammer, R. E., Brinster, R. L., Swift, G. H., MacDonald, R. J 1985 Specific expression of an elastase-human growth hormone fusion gene in pancreatic acinar cells of transgenic mice. Nature 313: 600–602.

Palmiter R D., Brinster, R. L., Hammer, R. E., Trumbauer, M. E., Rosenfeld, M. G., Bimberg, N. C., Evans, R. M. 1982 Dramatic growth of mice that develop from eggs microinjected with metallothionein-growth hormone fusion genes. Nature 300: 611–615.

Palmiter R D., Norstedt, G., Gelinas, R. E., Hammer, R. E., Brinster, R. L. 1983 Metallothionein-human GH fusion genes stimulate growth of mice. Science 222: 809–814.

Pursel V G., Pinkert, C. A., Miller, K. F., Bolt, D. J., Campbell, R. G., Palmiter, R. D., Brinster, R. L., Hammer, R. E. 1989 Genetic engineering of livestock. Science 244: 1281–1287.

Qu, D.; Ludwig, D. S.; Gammeltoft, S.; Piper, M.; Pelleymounter, M. A.; Cullen, M. J.; Mathes, W. F.; Przypek, J.; Kanarek, R.; Maratos-Flier, E. (1996). A role for melanin-concentrating hormone in the central regulation of feeding behaviour. Nature 380: 243–247.

Quaife C J., Mathews, L. S., Pinkert, C. A., Hammer, R. E., Brinster, R. L., Palmiter, R. D. 1989 Histopathology associated with elevated levels of growth hormone and insulin-like growth factor I in transgenic mice. Endocrinology 124: 40–48.

Reaven, G R. 1988 Role of insulin resistance in human disease. Diabetes 37: 1595–1607.

Richard, D., Rivest, R., Naimi, N., Timofeeva, E., and Rivest, S. (1996). Expression of corticotropin-releasing factor and its receptors in the brain of lean and obese Zucker rats. Endocrinology 137, 4786–95.

Roskam W G., Rougeon, F. 1979 Molecular cloning and nucleotide sequence of the human growth hormone structural gene. Nucleic Acid Research 10: 305–320.

Russell, J. C., Amy, R. M., Graham, S., Wenzel, L. M., and Dolphin, P. J. (1993). Effect of castration on hyperlipidemic, insulin resistant JCR: LA-corpulent rats. Atherosclerosis 100, 113-22.

Russo A F., Crenshaw, E. B, Lira, S. A, Simmons, D. M, Swanson, L. W, Rosenfeld, M. G 1988 Neuronal expression of chimeric genes in transgenic mice. Neuron 1: 311–320.

Sakurai, T.; Amemiya, A.; Ishii, M.; Matsuzaki, I.; Chemelli, R. M.; Tanaka, H.; Williams, S. C.; Richardson, J. A.; Kozlowski, G. P.; Wilson, S.; Arch, J. R. S.; Buckingham, R. E.; Haynes, A. C.; Carr, S. A.; Annan, R. S.; McNulty, D. E.; Liu, W.-S.; Terrett, J. A.; Elshourbagy, N. A.; Bergsma, D. J.; Yanagisawa, M. 1998. Orexins and orexin receptors: a family of hypothalamic neuropeptides and G protein-coupled receptors that regulate feeding behavior. Cell 92: 573–585.

Sambrook J., Fritsch E. F., Maniatis, T. 1989 Molecular Cloning. A Laboratory Manual: second edition.

Sanger F., Nicklen, S., Coulson, A. R. 1977 DNA sequencing with chain-terminating inhibitors. Proceedings of the National Society of Science. USA 74: 5463–5467.

Sausville E, Carney D, Battey J 1985 The human vasopressin gene is linked to the oxytocin gene and is selectively expressed in a cultured lung cancer cell line. J Biol Chem 260: 10236–10241.

Schmitz E., Mohr, E, Richter, D, 1991 Rat vasopressin and oxytocin genes are linked by a long interspersed repeated DNA element (LINE): Sequence and Transcriptional analysis of LINE. DNA and Cell Biology 10: 81–91.

Seeburg P H., Shine, J., Martial, J. A., Baxter, J. D., Goodman, H. M. 1977 Nucleotide sequence and amplification in bacteria of structural gene for rat growth hormone. Nature 270: 486–494.

Shanahan C M., Rigby, N. W., Murray, J. D., Marshall, J. T., Townrow, C. A., Nancarrow, C. D., Ward, K. A. 1989 Regulation of expression of a sheep metallothionein la-Sheep growth hormone fusion gene in transgenic mice. Molecular and Cellular Biology 9: 5473–5479.

Shea B T., Hammer, R. E., Brinster, R. L. 1987 Growth allometry of the organs in giant transgenic mice. Endocrinology 121: 1924–1930.

Shillabeer, G., Hornford, J., Forden, J. M., Wong, N. C., Russell, J. C., and Lau, D. C. (1992). Fatty acid synthase and adipsin mRNA levels in obese and lean JCR:LA-cp rats: effect of diet. J Lipid Res 33, 31–9.

Short M K., Clouthier, D. E., Schaefer, I. M., Hammer, R. E., Magnuson, M. A., Beale, E. G. 1992 Tissue-specific, developmental, hormonal and dietary regulation of rat phosphoenolpyruvate carboxykinase-human growth hormone fusion genes in transgenic mice. Molecular and Cellular Biology 12: 1007–1020.

Southern A M. 1975 Detection of specific sequences among DNA fragments separated by gel electrophoresis. Journal of Molecular Biology 98: 503–509.

Stewart T A., Clift, S., Pitts-Meek, S., Martin, L., Terrell, T. G., Liggitt, D., Oakley, H. 1992 An evaluation of the functions of the 22-kilodalton (kDa), the 20 kDa, and the N-terminal polypeptide forms of human growth hormone using transgenic mice. Endocrinology 130: 405-414.

Swanson L W., Simmons, D. M., Arriza, J., Hammer, R., Brinster, R., Rosenfeld, M. G., Evans, R. M. 1985 Novel developmental specificity in the nervous system of transgenic animals expressing growth hormone fusion genes. Nature 317: 363–366.

Szabo M., Butz, M. R., Banerjee, S. A., Chikaraishi, D. M., Frohman, L. A. 1995 Autofeedback suppression of growth hormone (GH) secretion in transgenic mice expressing a human GH reporter targeted by tyrosine hydroxylase 5'-flanking sequences to the hypothalamus. Endocrinology 136: 4044–4048.

Takaya K., Ogawa, Y., Isse, N., Okazaki, T., Satoh, Masuzaki, H., Mori, K., Tamura, N., Hosoda, K., Nakao, K. 1996 Molecular cloning of rat leptin isoform complementary DNAs-Identification of a missense mutation in Zucker fatty (fa/fa) rats. Biochemical and Biophysical Research Communications 225: 75–83.

Takeuchi, T., Suzuki, H., Sakurai, S., Nogami, H., Okuma, S., and Ishikawa, H. (1990). Molecular mechanism of growth hormone (GH) deficiency in the spontaneous dwarf rat-detection of abnormal splicing of GH messenger ribonucleic acid by the polymerase chain reaction. Endocrinology 126, 31–38.

Takiguchi S, Takata Y, Takahashi N, Kataoka K, Hirashima T, Kawano K, Miyasaka K, Funakoshi A, Kono A. 1998 A disrupted cholecystokinin A receptor gene induces diabetes in obese rats synergistically with ODB 1 gene. Am J Physiol 274:E265-E270.

Tartaglia L A., Dembski, M., Weng, X., Deng, N., Culpepper, J., Devos, R., Richards, G. J., Campfield, L. A., Clark, F. T., Deeds, J., Muir, C., Sanker, S., Moriarty, A., Moore, E. A., Monroe, C. A., Tepper, R. I. 1995 Identification and expression cloning of a leptin receptor, OB-R. Cell 83: 1263–1271.

Taylor, W. R., 1998 Dynamic databank serching with templates and multiple alignment. J. Mol. Biol. 280: 375–406.

Urban J H., Miller, M. A., Drake, C. T., Dorsa, D. M. 1990 Detection of vasopressin mRNA in cells of the medial amygdala but not the locus coeruleus by in situ hybridization. Journal of Chemical Neuroanatomy 3: 277–283.

Vandesande P. & Dierickx, D. 1975 Identification of the vasopressin producing and of the oxytocin producing neurons in the hypothalamic magnocellular neurosecretory system of the rat. Cell and Tissue Research 164: 153–162.

Van Tol H H M., Bolwerk, E. L. M., Lui, B., Burbach, J. P. 1988 Oxytocin and vasopressin gene expression in the hypothalamo-neurophyseal system of the rat during the estrous cycle, preganacy and lactation. Endocrinology 122: 945–951.

Vidal-Puig, A., Solanes, G., Grujic, D., Flier, J. S & Lowell, B. B. 1997 UCP3: an uncoupling protein homologue expressed preferentially and abundantly in skeletal muscle and brown adipose tissue. Biochem. Biophys. Res. Commun. 235: 79–82.

Wahl G M., Lewis, K. A., Ruiz, J. C., Rothenberg, B., Zhao, J., Evans, G. A. 1987 Cosmid vectors for rapid genomic walking, restriction mapping, and gene transfer. Proceeding of the National Academy of Science. USA 84: 2160–2164.

Waller S., Fairhall, K. M., Xu, J., Robinson, I. C. A. F., Murphy, D. 1996 Neurohypophyseal and fluid homeostasis in transgenic rats expressing a tagged rat vasopressin prepropeptide in hypothalamic neurons. Endocrinology 137: 5068–5077.

Whitaker, R. C., Wright, J. A., Pepe, M. S., Seidel, K. D., and Dietz, W. H. (1997). Predicting obesity in young adulthood from childhood and parental obesity. N Engl J Med 337, 869–73.

White, R B, Eisen, J A, Kasten, T L & Fernald, R D 1998 Second gene for gonadatropin-releasing hormone in humans PNAS 95, 305–309.

Wu-Peng X S, Chua S C Jr, Okada N, Liu S M, Nicolson M, Leibel R L 1997 Phenotype of the obese Koletsky (f) rat due to Tyr763 Stop mutation in the extracellular domain of the leptin receptor (Lepr): evidence for deficient plasma-to-CSF transport of leptin in both the Zucker and Koletsky obese rat. Diabetes 46:513–518.

Young III W S., Reynolds, K, Shepard, E. A, Gainer, H, Castel, M, 1990 Cell-specific expression of the rat oxytocin gene in transgenic mice. Journal of Neuroendocrinology 2: 917–925.

Young III WS 1992 Expression of oxytocin and vasopressin genes. Journal of Neuroendocrinology 4: 527–540.

Yun J S., Li, Y. S., Wight, D. C., Portanova, R., Selden, R. F. 1989 The human growth hormone transgene: expression in hemizygous and homozygous mice. Proceedings of the Society for Experimental Biology and Medicine 194: 308–313.

Zeng Q., Carter, D. D., Murphy, D. 1994b Cell specific expression of a vasopressin transgene in rats. Journal of Neuroendocrinology 6: 469–477.

Zeng Q., Foo, N-C., Funkhouser, J. M., Carter, D. A., Murphy, D. 1994a Expression of a rat vasopressin transgene in rat testes. Journal of Reproduction and Fertility 102: 471–481.

Zhang Y., Proenca, R., Maffei, M., Barone, M., Leopold, L., Friedman, J. M. 1994 Positional cloning of the mouse obese gene and its human homologue. Nature 372: 425–427.

What is claimed is:

1. A nucleic acid encoding a 5'OT-EST polypeptide comprising an amino acid sequence selected from the group consisting of the sequences set forth in any one of SEQ ID Nos. 2, 4, or 6.

2. The nucleic acid of claim 1, having a sequence selected from the group consisting of SEQ. ID. Nos. 1, 3, 5, 7, 16 or 17, wherein a polypeptide encoded by a said nucleic acid sequence modulates the obesity of an animal.

3. The nucleic acid of claim 2, comprising the sequence with SEQ ID NO: 31.

4. A nucleic acid vector comprising a nucleic acid sequence of any one of claims 1 to 3.

5. The vector of claim 4, wherein said vector is a cosmid vector.

6. The vector of claim 4 or 5 further comprising one or more sequences selected from the group consisting of sequences of the coding region of the oxytocin (OT) gene, the coding region of the vasopressin (AVP) gene, or the coding region of the human growth hormone (hGH) gene.

7. A vector of claim 5, wherein said vector has the structure of cVO14 as set forth in FIG. 4 (SEQ. ID. No. 17).

8. A cell transformed with a vector of any one of claims 4 to 7.

9. The nucleic acid of claim 1, wherein said 5'OT-EST polypeptide, in vivo, modulates the obesity of an animal which expresses said 5'OT-EST polypeptide.

10. The nucleic acid of any one of claims 1 or 9 wherein said 5'OT-EST polypeptide comprises the sequence of SEQ ID NO: 37.

11. The nucleic acid of any one of claims 1 or 9 wherein said 5'OT-EST polypeptide comprises the sequence of SEQ ID NO: 8.

12. A method for producing a 5'OT-EST polypeptide having a sequence selected from the group consisting of (a) the sequences set forth in any one of SEQ ID Nos. 2, 4, 6, wherein said encoded amino acid sequence modulates the obesity of an animal, the method comprising transforming a cell with a vector of any one of claims 4 to 7 and culturing the cell to produce the polypeptide.

13. A diagnostic reagent comprising at least one detectably labeled nucleic acid probe of 15 to 50 bases which hybridizes in a solution containing 6×SSC. 5× Denhardt's, 1% SDS (sodium dodecyl sulphate), 0.1 M $Na^+$ pyrophosphate and 0.1 mg/ml denatured salmon sperm DNA at 65° C. to a sequence selected from the group consisting of any one of SEQ ID NOs 1, 3 or 5.

14. The diagnostic reagent of claim 12 wherein said at least one detectably labeled nucleic acid probe is 10 to 50 nucleotides in length.

15. A method for the detection of mutations, polymorphisms or other changes in S'OT-EST which may predispose an individual to obesity, said method comprising hybridizing a nucleic acid sample from an individual to a detectable labeled probe that is capable of hybridizing to a sequence selected from the group consisting of (a) any one of SEQ ID NOs 1, 3 or 5, and (b) a sequence at least 90% identical over the 111 length of one of SEQ ID NOs 1, 3 or 5, and detecting a mutation, polymorphism or other change in S'OT-EST sequence relative to SEQ ID NOs 1, 3 or 5 in said individual, wherein the mutation, polymorphism or other change in 5'OT-EST may predispose the individual to obesity.

\* \* \* \* \*